United States Patent
Gu et al.

(10) Patent No.: US 11,065,362 B2
(45) Date of Patent: Jul. 20, 2021

(54) VISCOELASTIC HYDROGELS WITH FAST STRESS RELAXATION

(71) Applicant: President and Fellows of Harvard College, Cambridge, MA (US)

(72) Inventors: Luo Gu, Cambridge, MA (US); Ovijit Chaudhuri, San Mateo, CA (US); Nathaniel D. Huebsch, Colma, CA (US); David J. Mooney, Sudbury, MA (US); Max Carlton Darnell, Somerville, MA (US); Simon Young, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 14/738,294

(22) Filed: Jun. 12, 2015

(65) Prior Publication Data

US 2015/0359928 A1 Dec. 17, 2015

Related U.S. Application Data

(60) Provisional application No. 62/011,512, filed on Jun. 12, 2014.

(51) Int. Cl.
| | |
|---|---|
| *A61L 27/20* | (2006.01) |
| *A61L 27/52* | (2006.01) |
| *C12N 5/077* | (2010.01) |
| *A61L 27/56* | (2006.01) |
| *A61L 27/54* | (2006.01) |
| *A61L 27/38* | (2006.01) |

(52) U.S. Cl.
CPC ........... *A61L 27/20* (2013.01); *A61L 27/3834* (2013.01); *A61L 27/52* (2013.01); *A61L 27/54* (2013.01); *A61L 27/56* (2013.01); *C12N 5/0654* (2013.01); *A61L 2400/12* (2013.01); *A61L 2430/02* (2013.01); *C12N 2506/1346* (2013.01); *C12N 2513/00* (2013.01); *C12N 2533/74* (2013.01)

(58) Field of Classification Search
None
See application file for complete search history.

(56) References Cited

U.S. PATENT DOCUMENTS

| | | |
|---|---|---|
| 6,642,363 B1 | 11/2003 | Mooney et al. |
| 2007/0116680 A1 | 5/2007 | Stegemann et al. |

FOREIGN PATENT DOCUMENTS

| | | | |
|---|---|---|---|
| EP | 1806367 | * | 7/2007 |
| WO | WO-2010/120749 A2 | | 10/2010 |
| WO | WO 2012/048165 | * | 4/2012 |

OTHER PUBLICATIONS

Mahou et al. (Macromolecules, 43, 1371-1378, 2010) Alginate-Poly(ethylene glycol) Hybrid . . . .*
Kerim et al. (Biomacromolecules 2009. 10, 3122-3129) Chemoselective crosslinking . . . .*
Hatch et al. (Langmuir, 27(7), 4257-4264, 2011) Engineered alginate hydrogels . . . .*
Wilson et al. (Soft Matter., 8(2), 390-398, 2012) Hydrogels with well-defined . . . .*
Chaudhuri, O. et al., "Substrate stress relaxation regulates cell phenotype," presented on Feb. 4, 2014 at the ASME 2014 3rd Global Congress on NanoEngineering for Medicine and Biology (NEMB2014), held in San Francisco, CA.
Chaudhuri, O. et al., Abstract #627, "Substrate stress relaxation regulates cell spreading, proliferation, and differentiation," of the poster presented at the 2013 American Society of Cell Biology Annual Meeting held on Dec. 14-18, 2013 in New Orleans, LA.
Lee, K.Y. et al., "Alginate: properties and biomedical applications," *Prog. Polym. Sci.*, vol. 37, No. 1, 106-126, 2012.
Chaudhuri, O. et al., "Substrate stress relaxation regulates cell spreading," *Nature Communications*, vol. 6, Article No. 6365, 2015.
Chaudhuri, O. et al., "Hydrogels with tunable stress relaxation regulate stem cell fate and activity," *Nature Materials*, vol. 15, No. 3, 326-334, 2016.

* cited by examiner

*Primary Examiner* — Tigabu Kassa
(74) *Attorney, Agent, or Firm* — McCarter & English, LLP; Maria Laccotripe Zacharakis

(57) ABSTRACT

Provided are fast relaxing hydrogels that are useful for regulating cell behavior and enhancing tissue regeneration, e.g., bone regeneration.

23 Claims, 25 Drawing Sheets

Specification includes a Sequence Listing.

A

B

A

Lo, et al., *Biophys. J.*, 2000

B

Kong, et al., *Nature Mat.*, 2005

C

Spreading

Yeung, et al., *Cell Motil. & Cyt.*, 2005

D

Stem cell differentiation

Engler, et al., *Cell*, 2006

```
                           SEQUENCE LISTING

<160> NUMBER OF SEQ ID NOS: 17

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Arg Gly Asp Ser
1

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Arg Glu Asp Val
1

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Arg Gly Asp Val
1

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4
```

```
Leu Arg Gly Asp Asn
1               5

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ile Lys Val Ala Val
1               5

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Tyr Ile Gly Ser Arg
1               5

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Pro Asp Ser Gly Arg
1               5

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Arg Asn Ile Ala Glu Ile Ile Lys Asp Ala
1               5                   10

<210> SEQ ID NO 9
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Arg Gly Asp Thr
1

<210> SEQ ID NO 10
<211> LENGTH: 4
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 10

Asp Gly Glu Ala
1

<210> SEQ ID NO 11
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any hydrophobic amino acid

<400> SEQUENCE: 11

Val Thr Xaa Gly
1

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gly Gly Gly Gly Arg Gly Asp Ser Pro
1               5

<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any hydrophobic amino acid
<220> FEATURE:
<221> NAME/KEY: MOD_RES
<222> LOCATION: (2)..(3)
<223> OTHER INFORMATION: Any basic amino acid
<220> FEATURE:
<221> NAME/KEY: MOD_RES
<222> LOCATION: (4)..(4)
<223> OTHER INFORMATION: Any hydrophobic amino acid
<220> FEATURE:
<221> NAME/KEY: MOD_RES
<222> LOCATION: (5)..(5)
<223> OTHER INFORMATION: Any basic amino acid
<220> FEATURE:
<221> NAME/KEY: MOD_RES
<222> LOCATION: (6)..(6)
<223> OTHER INFORMATION: Any hydrophobic amino acid

<400> SEQUENCE: 13

Xaa Xaa Xaa Xaa Xaa Xaa
1               5

<210> SEQ ID NO 14
<211> LENGTH: 6
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 14

Pro Arg Arg Ala Arg Val
1               5

<210> SEQ ID NO 15
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Tyr Glu Lys Pro Gly Ser Pro Pro Arg Glu Val Val Pro Arg Pro Arg
1               5                   10                  15

Pro Gly Val

<210> SEQ ID NO 16
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Arg Pro Ser Leu Ala Lys Lys Gln Arg Phe Arg His Arg Asn Arg Lys
1               5                   10                  15

Gly Tyr Arg Ser Gln Arg Gly His Ser Arg Gly Arg
            20                  25

<210> SEQ ID NO 17
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Arg Ile Gln Asn Leu Leu Lys Ile Thr Asn Leu Arg Ile Lys Phe Val
1               5                   10                  15

Lys
```

VISCOELASTIC HYDROGELS WITH FAST STRESS RELAXATION

RELATED APPLICATIONS

This application claims priority to U.S. Provisional Application No. 62/011,512, filed on Jun. 12, 2014, the entire contents of which are hereby incorporated herein by reference.

GOVERNMENT SUPPORT

The invention was supported, in whole, or in part, by a National Institutes of Health (NIH) F32 grant (CA153802) and a NIH grant (R01 DE013033). The Government has certain rights in the invention.

FIELD OF THE INVENTION

The present invention relates to hydrogels that exhibit stress relaxation and their ability to regulate cell behavior.

SEQUENCE LISTING

The instant application contains a Sequence Listing which has been submitted electronically in ASCII format and is hereby incorporated by reference in its entirety. Said ASCII copy, created on Jun. 10, 2015, is named 117823-09202_SL.txt and is 4,561 bytes in size.

BACKGROUND OF THE INVENTION

Bone diseases and wounds are a source of mobility hindrance and mortality. No effective treatments are available for some of the common skeleton disorders, including arthritis, osteoarthritis, osteosarcoma, and metastatic bone cancer. Also, wounds, such as those caused by trauma or disease, sometimes require regeneration of bone. Accordingly, there is a need for materials and methods for bone regeneration.

Hydrogels are often used in tissue engineering as synthetic extracellular matrices for 3-dimensional (3D) culture. However, these hydrogels are typically elastic, whereas natural ECM is viscoelastic or malleable and exhibits stress relaxation, so that cell generated forces can mechanically alter matrix structure. There is a need for hydrogels, for example, for use in bone regeneration, in which stress relaxation can be tuned independently of other mechanical properties, such as initial elastic modulus, cell adhesion ligand density, and matrix degradation. The present invention addresses these needs.

SUMMARY OF THE INVENTION

The present invention is based, at least in part, on the surpring discovery that stress relaxation influences interactions between a cell and extracellular matrix (ECM). Specifically, it was determined that fast relaxing hydrogels, i.e., hydrogels characterized by a fast stress relaxation rate ($\tau_{1/2}$) of 1000 seconds or less can alter cell behavior, e.g., can increase cell spreading and proliferation. In addition, it was also determined that such hydrogels can influence differentiation of a cell, e.g., a stem cell, such as a mesenchymal stem cell (MSC), both in vitro and in vivo.

It was also surprisingly discovered that a hydrogel comprising a plurality of alginate polymer chains and a plurality of spacer molecules that are attached to, but do not cross-link the alginate polymer chains, is characterized by a fast relaxation rate ($\tau_{1/2}$). Accordingly, the present invention provides a fast relaxing hydrogel comprising a plurality of alginate polymer chains and a plurality of spacer molecules, wherein the plurality of alginate polymer chains are ionically cross-linked to each other; and wherein each of the plurality of spacer molecules comprises a first end and a second end, wherein the first end is attached to an alginate polymer chain and the second end is not attached to an alginate polymer chain; and wherein the hydrogel is characterized by a fast stress relaxation rate ($\tau_{1/2}$).

The hydrogels provided by the present invention are useful for altering cell behavior, e.g., cell spreading and proliferation, and for influencing differentiation of a cell. The hydrogels of the present invention are also useful, e.g., in the field of regenerative medicine for regenerating tissues and for preparing novel biomaterials, e.g., tissue constructs.

Accordingly, the present invention provides a fast relaxing hydrogel comprising a plurality of alginate polymer chains and a plurality of spacer molecules, wherein the plurality of alginate polymer chains are ionically cross-linked to each other; wherein each of the plurality of spacer molecules comprises a first end and a second end, wherein the first end is attached to an alginate polymer chain and the second end is not attached to an alginate polymer chain; and wherein the hydrogel is characterized by a fast stress relaxation rate ($\tau_{1/2}$).

In some aspects, each of the alginate polymer chain has a molecular weight of about 250 kDa or less. In some aspects, the alginate polymer chain has a molecular weight of about 70 kDa or less. In a specific embodiment, the alginate polymer chain has a molecular weight of about 35 kDa.

In some embodiments, the hydrogel is viscoelastic and exhibits relaxation behavior when stress is applied to the hydrogel. In one aspect, the stress relaxation rate ($\tau_{1/2}$) is 1000 seconds or less. In another aspect, the stress relaxation rate ($\tau_{1/2}$) is 500 seconds or less. In yet another aspect, the stress relaxation rate ($\tau_{1/2}$) is 100 seconds or less.

In some embodiments, the plurality of alginate polymer chains and the plurality of spacer molecules are present in the hydrogel at a ratio of between about 1:1 and about 10:1 spacer molecule:alginate polymer chain. In further embodiments, the ratio is between about 1:1 and about 4:1 spacer molecule:alginate polymer chain. Yet a specific embodiment, the ratio is about 2:1 spacer molecule:alginate polymer chain.

In one aspect, the spacer is molecule is polyethylene glycol (PEG). In a further aspect, the PEG has a molecular weight of less than 50 kDa. In yet another aspect, the PEG has a molecular weight of between about 5 kDa to about 20 kDa.

In some embodiments, the hydrogel further comprises a cell adhesive peptide. In some embodiments, the cell adhesive peptide is attached to each of the plurality of alginate polymer chains. In a specific embodiment, the cell adhesive peptide comprises an arginine-glycine-aspartate (RGD) amino acid sequence.

In certain aspects, the plurality of alginate polymer chains are ionically cross-linked using divalent or trivalent cations. In some aspects, the divalent cation is $Ca^{2+}$.

In some embodiments, the hydrogel of the invention comprises interconnected pores. In further aspects, the pores comprise nanopores.

In certain aspects, the hydrogel of the invention comprises a mammalian cell. In a further aspect, the mammalian cell is a fibroblast or a mesenchymal stem cell (MSC).

In some embodiments, the hydrogel of the invention is characterized by an initial elastic modulus of about 11 kPa to about 30 kPa.

The present invention also provides a method of enhancing proliferation or differentiation of a cell, the method comprising contacting the cell with a fast-relaxing hydrogel, wherein the hydrogel is characterized by a fast stress relaxation rate ($\tau_{1/2}$), thereby enhancing proliferation or differentiation of a cell. In some aspects, the cell is a mesenchymal stem cell (MSC). In some aspects, the ability of the MSC to undergo osteogenic differentiation is enhanced as compared to the MSC that has been contacted with a hydrogel characterized by a slow stress relaxation rate ($\tau_{1/2}$). In other aspects, the cell is encapsulated in the hydrogel.

In some embodiments, the the hydrogel comprises a plurality of alginate polymer chains and a plurality of spacer molecules, wherein the plurality of alginate polymer chains are ionically cross-linked to each other; and wherein each of the plurality of spacer molecules comprises a first end and a second end, wherein the first end is attached to an alginate polymer chain and the second end is not attached to an alginate polymer chain.

In certain embodiments, the spacer molecule is polyethylene glycol (PEG). In some embodiments, the hydrogel comprises a cell adhesive peptide. In further embodiments, the cell adhesive peptide is attached to each of the plurality of alginate polymer chains. In a further embodiment, the cell adhesive peptide comprises an arginine-glycine-aspartate (RGD) amino acid sequence.

In one embodiment, the hydrogel is characterized by an initial modulus of about 11-30 kPa.

In some aspects, the proliferation of the cell is enhanced by at least 1.5-fold as compared to proliferation of a cell that has been contacted with a hydrogel characterized by a slow stress relaxation rate ($\tau_{1/2}$).

The present invention also provides a method of regenerating a tissue in a subject in need thereof, comprising administering to the subject a fast-relaxing hydrogel, wherein the hydrogel is characterized by a fast stress relaxation rate ($\tau_{1/2}$), thereby regenerating a tissue in a subject.

In some embodiments, the hydrogel comprises a plurality of alginate polymer chains and a plurality of spacer molecules, wherein the plurality of alginate polymer chains are ionically cross-linked to each other; and wherein each of the plurality of spacer molecules comprises a first end and a second end, wherein the first end is attached to an alginate polymer chain and the second end is not attached to an alginate polymer chain. In a specific embodiment, the spacer molecule is polyethylene glycol (PEG).

In some aspects, the hydrogel further comprises a cell adhesive peptide. In a further aspect, the cell adhesive peptide is attached to each of the plurality of alginate polymer chains. In another further aspect, the cell adhesive peptide comprises an arginine-glycine-aspartate (RGD) amino acid sequence.

In some embodiments, the tissue comprises a bone tissue.

In certain aspects, the hydrogel is characterized by an initial modulus of about 11-30 kPa.

In some embodiments, the hydrogel is seeded with mammalian cells prior to administration to the subject. In a further aspect, the mammalian cells are encapsulated by the hydrogel prior to administration to the subject.

In certain embodiments, the subject's cells seed onto the hydrogel after the hydrogel is administered to the subject. In some aspects, proliferation and/or osteogenic differentiation of a stem cell in the subject is enhanced as compared to proliferation and/or osteogenic differentiation of a stem cell in the subject who has been administered a hydrogel characterized by a slow stress relaxation rate ($\tau_{1/2}$).

In some embodiments, the present invention also provides a tissue construct comprising the hydrogel of the invention, e.g., a fast relaxing hydrogel comprising a plurality of alginate polymer chains and a plurality of spacer molecules, wherein the plurality of alginate polymer chains are ionically cross-linked to each other; wherein each of the plurality of spacer molecules comprises a first end and a second end, wherein the first end is attached to an alginate polymer chain and the second end is not attached to an alginate polymer chain; and wherein the hydrogel is characterized by a fast stress relaxation rate ($\tau_{1/2}$).

In another embodiments, the spacer is molecule in the hydrogel is polyethylene glycol (PEG). In another embodiment, the hydrogel further comprises a cell adhesive peptide. In yet another embodiment, the cell adhesive peptide is attached to each of the plurality of alginate polymer chains. In a further embodiment, the cell adhesive peptide comprises an arginine-glycine-aspartate (RGD) amino acid sequence.

Other features and advantages of the invention will be apparent from the following detailed description and claims.

Figure 1:
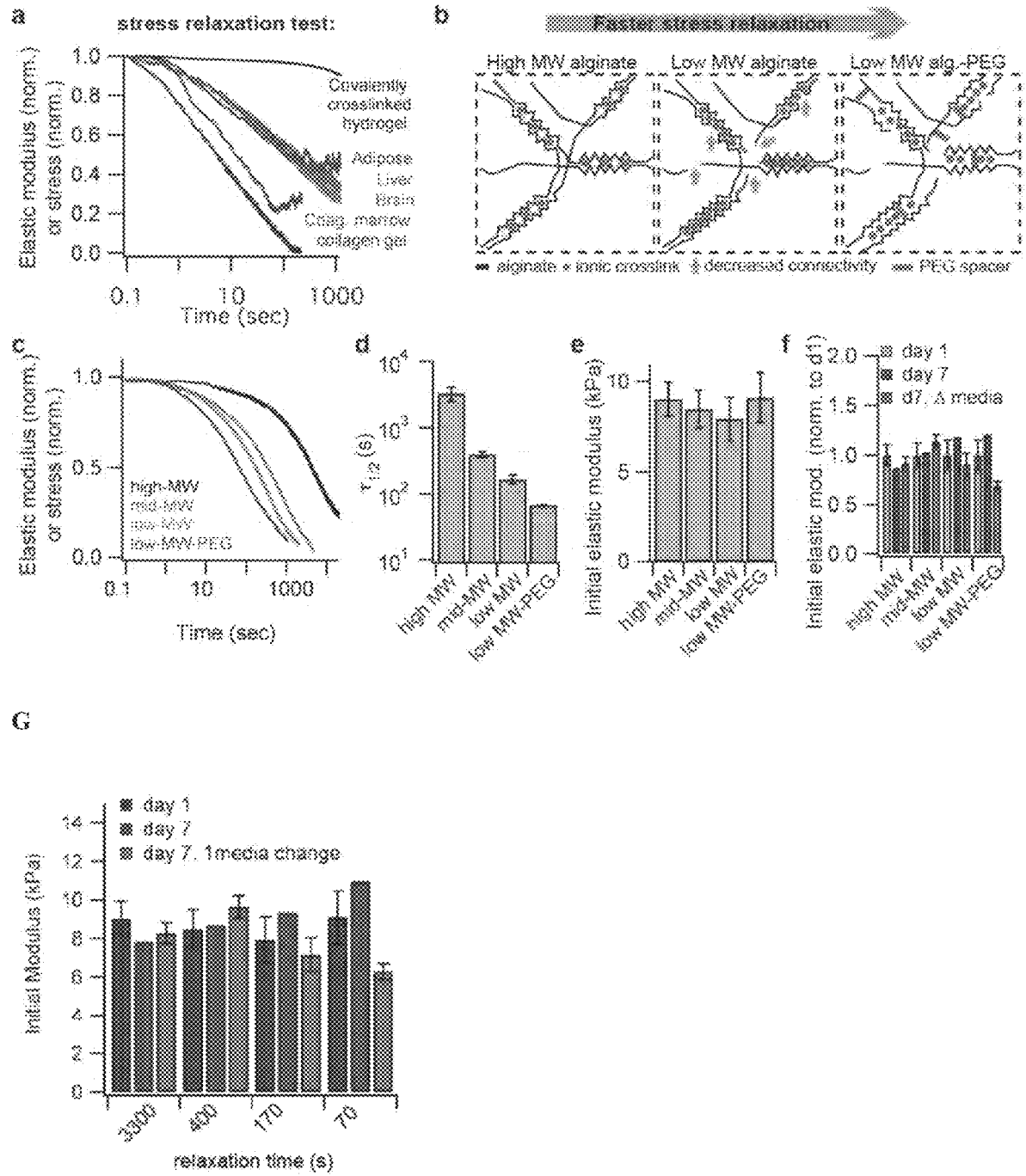
FIG. 1 demonstrates that changes to the nanoscale architecture of alginate hydrogels modulate their stress relaxation properties independent of initial elastic modulus.

Panel a of FIG. 1 is a graph showing that living tissues are viscoelastic and exhibit stress relaxation. The graph shows the results of stress relaxation tests for a number of materials, including a covalently crosslinked polyacrylamide hydrogel, a collagen gel, and various rat tissues at a strain of 15%. Stress was normalized by the initial stress value, and was the same as the normalized elastic modulus in a stress relaxation test.

Panel b of FIG. 1 is a set of schematics illustrating the influence of the molecular weight of the alginate polymer chain (shown in blue) on the stress relaxation of a hydrogel. Specifically, stress relaxation in hydrogels comprising lower molecular weight alginate polymer chains would increase due to the decreased connectivity and long range entanglement of the polymer chain network (left & middle panels). Arrows indicated the decreased connections in hydrogels composed of lower molecular weight alginate polymer chains. The associated reduction in the initial modulus is compensated for by increasing the number of ionic cross-links with the increasing concentration of a crosslinker, e.g., $Ca^{2+}$ (depicted by circles). Additionally, coupling low molecular weight spacers, e.g., PEG spacers, to the alginate polymer chain also increased the stress relaxation properties in the hydrogel due to steric interference with crosslinking zones in the alginate (right panel).

Panel c of FIG. 1 is a graph demonstrating the results of stress relaxation tests performed on hydrogels composed of alginates with different molecular weights, or on a hydrogel composed of low molecular weight alginate coupled to a PEG spacer at 15% compressional strain.

Panel d of FIG. 1 is a bar graph showing the quantification of timescale at which the stress is relaxed to half of its original value, $\tau_{1/2}$, from stress relaxation tests in FIG. 1C. Changes in the architecture of hydrogels significantly decrease the timescale of stress relaxation (Spearman's rank correlation coefficient, p<0.0001).

Panel e of FIG. 1 is a bar graph showing the results of initial modulus measurements of gels in FIG. 1C and demonstrates that gels with widely varying relaxation kinetics exhibited similar initial moduli. Differences between moduli were not significant, and elastic moduli showed no trend with altered hydrogel architecture.

Panel f of FIG. 1 is a bar graph showing the initial compressional modulus of alginate hydrogels with the indicated timescale of stress relaxation. The hydrogels were equilibrated in DMEM after 1 day, after 7 days with no media change, and after 7 days when the media is replaced at day 3.

Panel G of FIG. 1 is a bar graph showing the initial modulus of hydrogels. In particular, the bar graph shows initial compressional modulus at the indicated timescale of stress relaxation of alginate hydrogels equilibrated in DMEM after 1 day, after 7 days with no media change, and after 7 days when the media is replaced at day 3. As shown in FIGS. 1F-G, the similarity in modulus after 7 days for gels without a media change indicated that there is minimal degradation of the alginate gels after 7 days. The slight decrease in the modulus observed for faster relaxing gels after 7 days was attributed to calcium leaching out of the gels. All data are shown as mean+/−s.d.

Figure 2:
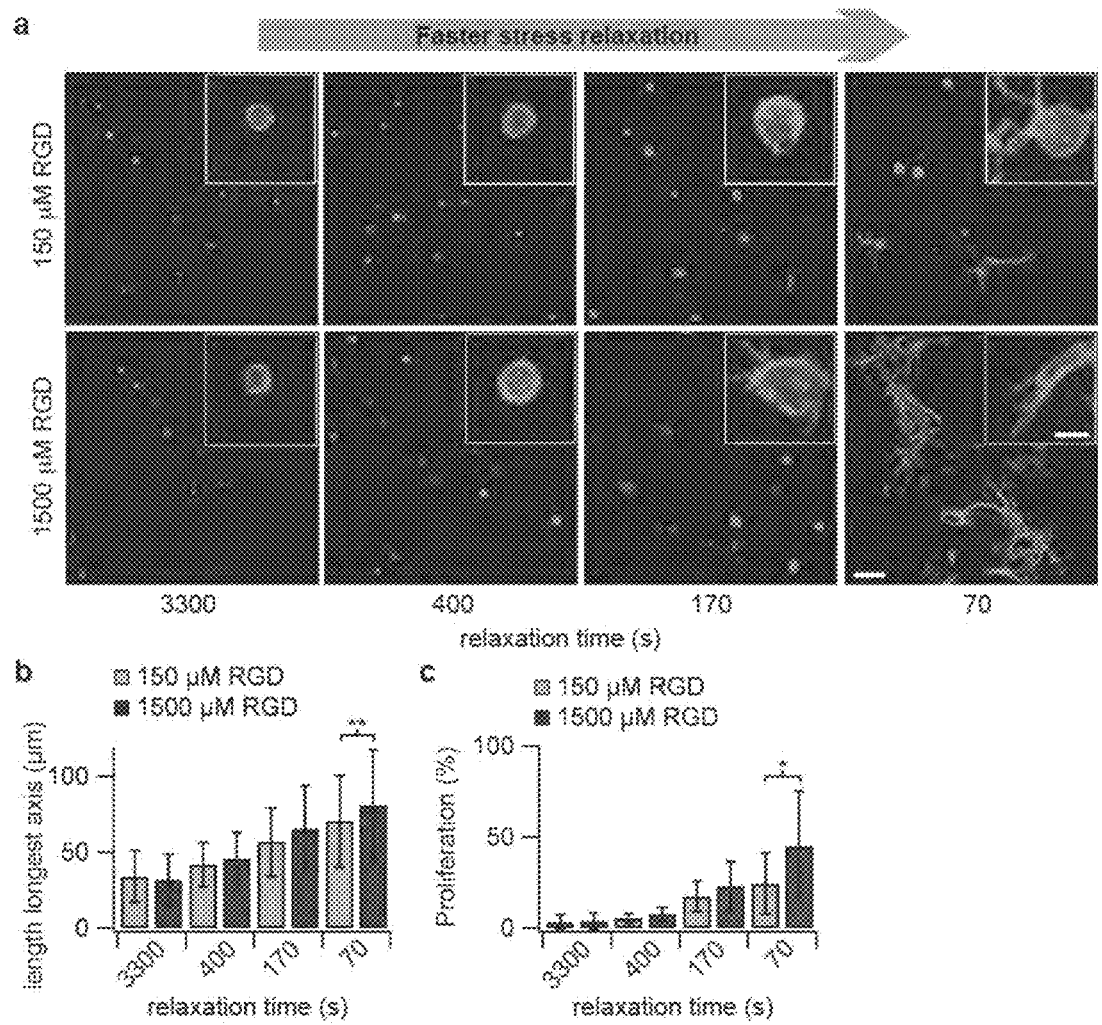

FIG. 2 shows that cell spreading and proliferation for fibroblasts encapsulated within gels were enhanced with faster stress relaxation.

Panel a of FIG. 2 is a panel of representative images of 3T3 cells encapsulated within alginate hydgels characterized by the indicated $\tau_{1/2}$ for stress relaxation and two different RGD concentrations (average initial modulus of 9 kPa). Green color represents actin staining and blue represents nucleus. Images were taken after 7 days in culture. Scale bar is 100 μm for the larger image and 20 μm for the inset.

Panel b of FIG. 2 is a graph showing the magnitude of the longest dimension of the smallest bounding box fully containing individual 3T3 cells as a function of relaxation time. ** indicates p<0.01 (student's t-test). Cell spreading increased significantly with faster stress relaxation (Spearman's rank correlation, p<0.0001 for both values of RGD).

Panel c of FIG. 2 is a graph showing the magnitude of cell proliferation as a function of relaxation time. * indicates p<0.05 (student's t-test). Proliferation was found to increase with faster stress relaxation (Spearman's rank correlation, p<0.0001 for both values of RGD). Data are shown as mean+/−s.d.

Figure 3:
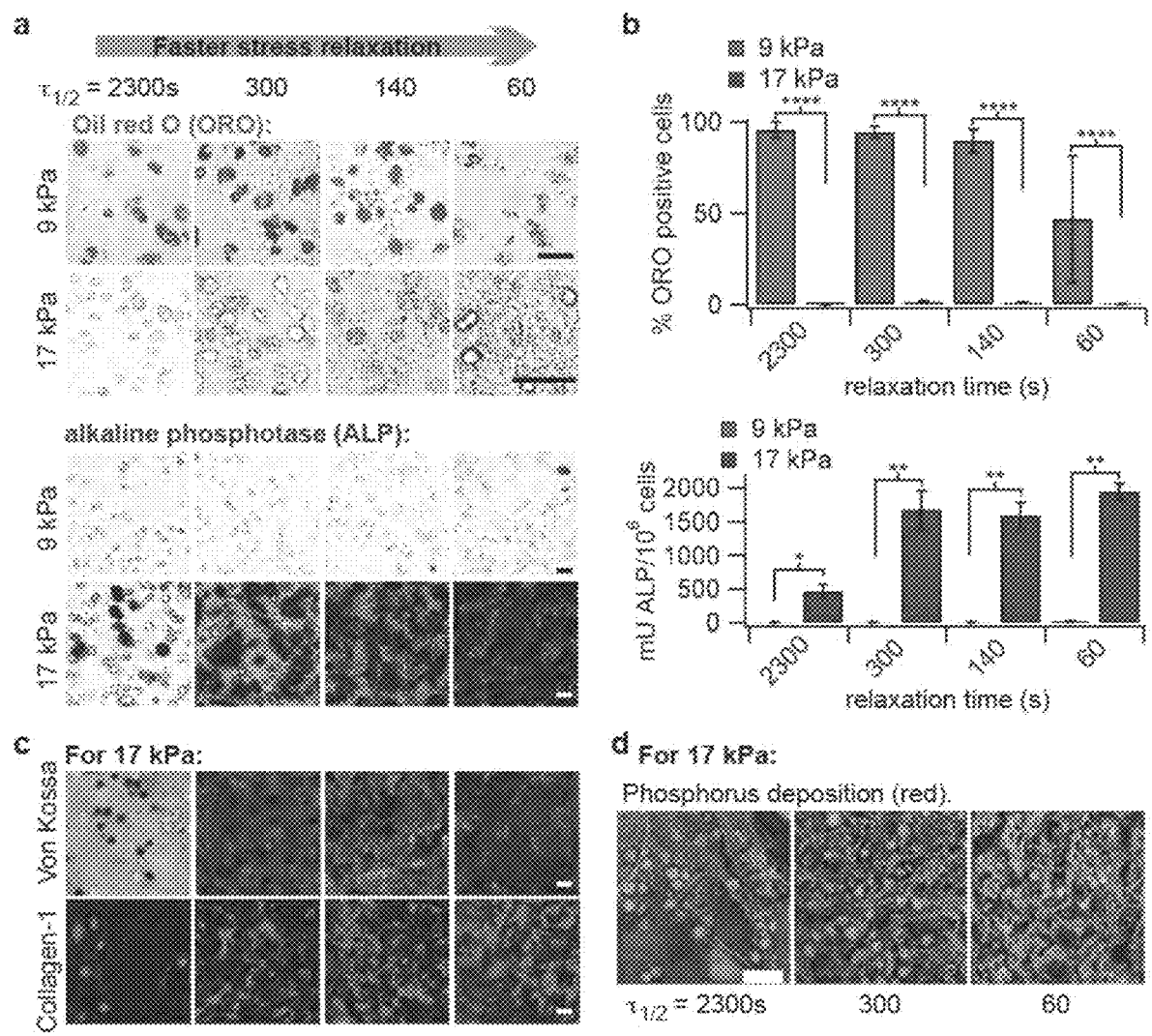

FIG. 3 shows that MSCs underwent osteogenic differentiation and formed an interconnected mineralized collagen-1 rich matrix only in rapidly relaxing gels.

Panel a of FIG. 3 is a panel of representative images of cryosections with Oil red O (ORO) staining (red), indicating adipogenic differentiation, and alkaline phosphatase staining (blue), indicating early osteogenic differentiation, for MSC cultured for 7 days in hydrogels characterized by the indicated initial modulus and timescale of stress relaxation. RGD density was 1500 μM. Scale bars were 25 μm.

Panel b of FIG. 3 is a graph showing the % of cells staining positive for ORO (top panel), and the results of a quantitative assay for alkaline phosphatase activity from lysates of cells in hydrogels from the indicated conditions at 7 days in culture (bottom panel), with *, , and ** indicating p<0.05, 0.01, & 0.0001, respectively (Student's t-test). Bars for % cells staining for ORO in gels with initial modulus of 17 kPa and alkaline phosphatase activity of cells in gels with initial modulus of 9 kPa were barely visible due to the small values relative to the other conditions. Osteogenic differentiation increased significantly with a faster stress relaxation (Spearman's rank correlation, p<0.0001).

Panel c of FIG. 3 is a panel of images showing a Von Kossa (mineralization) and collagen-I stain on cryosections from gels with the indicated characteristics after 2 weeks of culture. Scale bars are 25 μm.

Panel d of FIG. 3 is a panel of scanning electron microscope (SEM) and energy dispersive X-ray spectrometry (SEM-EDS) images of sections of gels with the indicated characteristics (all gels at 1500 μM RGD) after 2 weeks of 3D culture of MSCs. Phosphorus elemental maps (P mapped in red) are overlaid on their corresponding backscattered SEM images. Scale bar is 50 μm. All data are shown as mean+/−s.d. For simplicity, $\tau_{1/2}$ values shown in this figure are an average of the $\tau_{1/2}$ values at 9 kPa and 17 kPa. Specific values for each condition are shown in Table 1.

Figure 4:
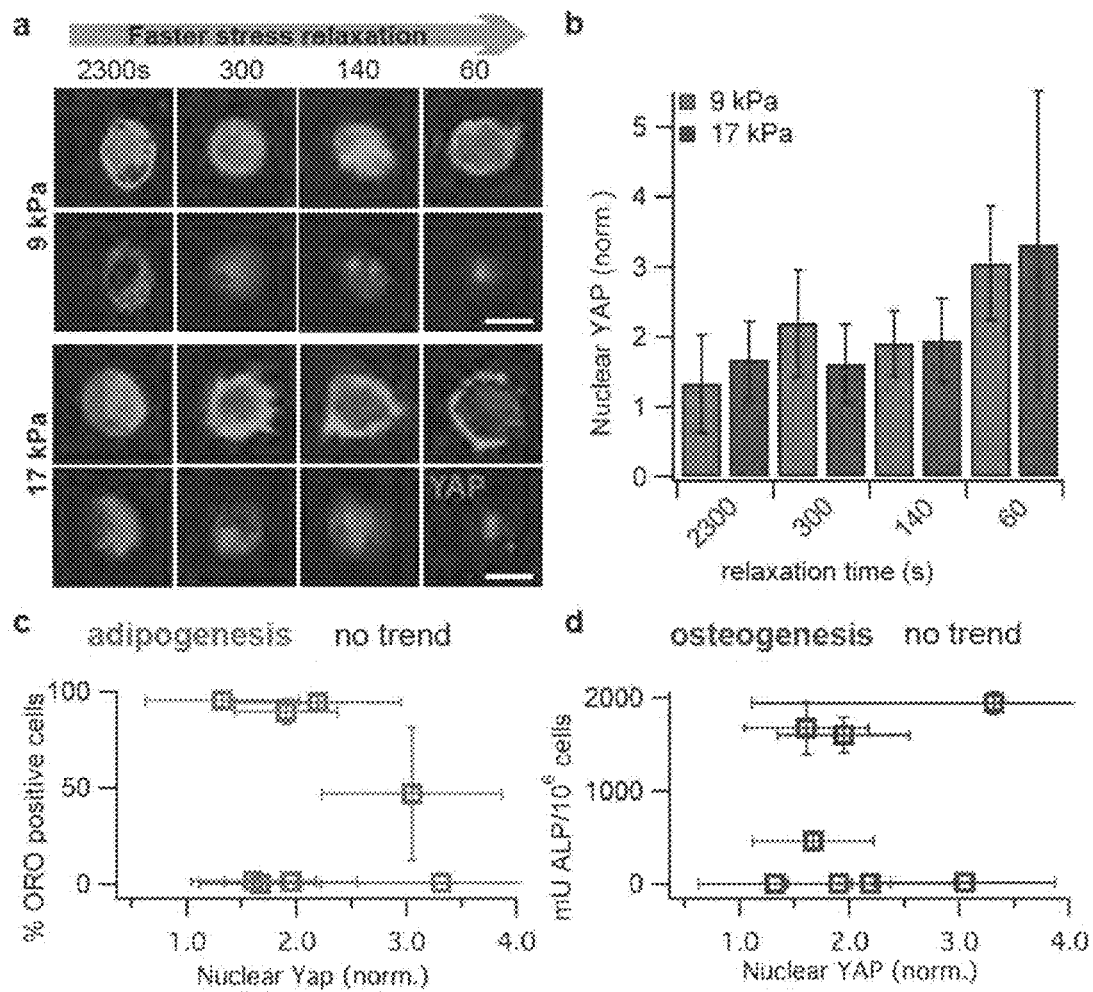

FIG. 4 shows that nuclear localization of YAP is enhanced by faster stress relaxation, but decoupled from MSC fate. YAP is a transcriptional regulator that is thought to be the key regulatory element controlling the gene expression of cells in response to mechanical or geometric cues. Nuclear localization of YAP was previously found to direct MSC differentiation into adipogenic or osteogenic lineages for MSCs cultured on 2D acrylamide substrates in response to altered substrate stiffness.

Panel a of FIG. 4 is a panel of representative immunofluorescence staining for actin (green), nucleus (blue), and YAP (red) in MSCs cultured in the indicated conditions for a week. Scale bar is 10 μm.

Panel b of FIG. 4 is a graph showing the ratio of the concentration of nuclear YAP to the concentration of YAP in the cytoskeleton. Nuclear YAP increases significantly with faster stress relaxation for both initial elastic moduli (Spearman's rank correlation, p<0.0001 for both).

Panel c of FIG. 4 is a graph showing the percentage of D1 cells that stain positive for ORO as a function of the relative nuclear YAP.

Panel d of FIG. 4 is a graph showing the quantity of ALP in osteogenically differentiated D1 cells as a function of the relative nuclear YAP. No trend is observed in FIGS. 4C and 4D. All data are shown as mean+/−s.d.

Figure 5:
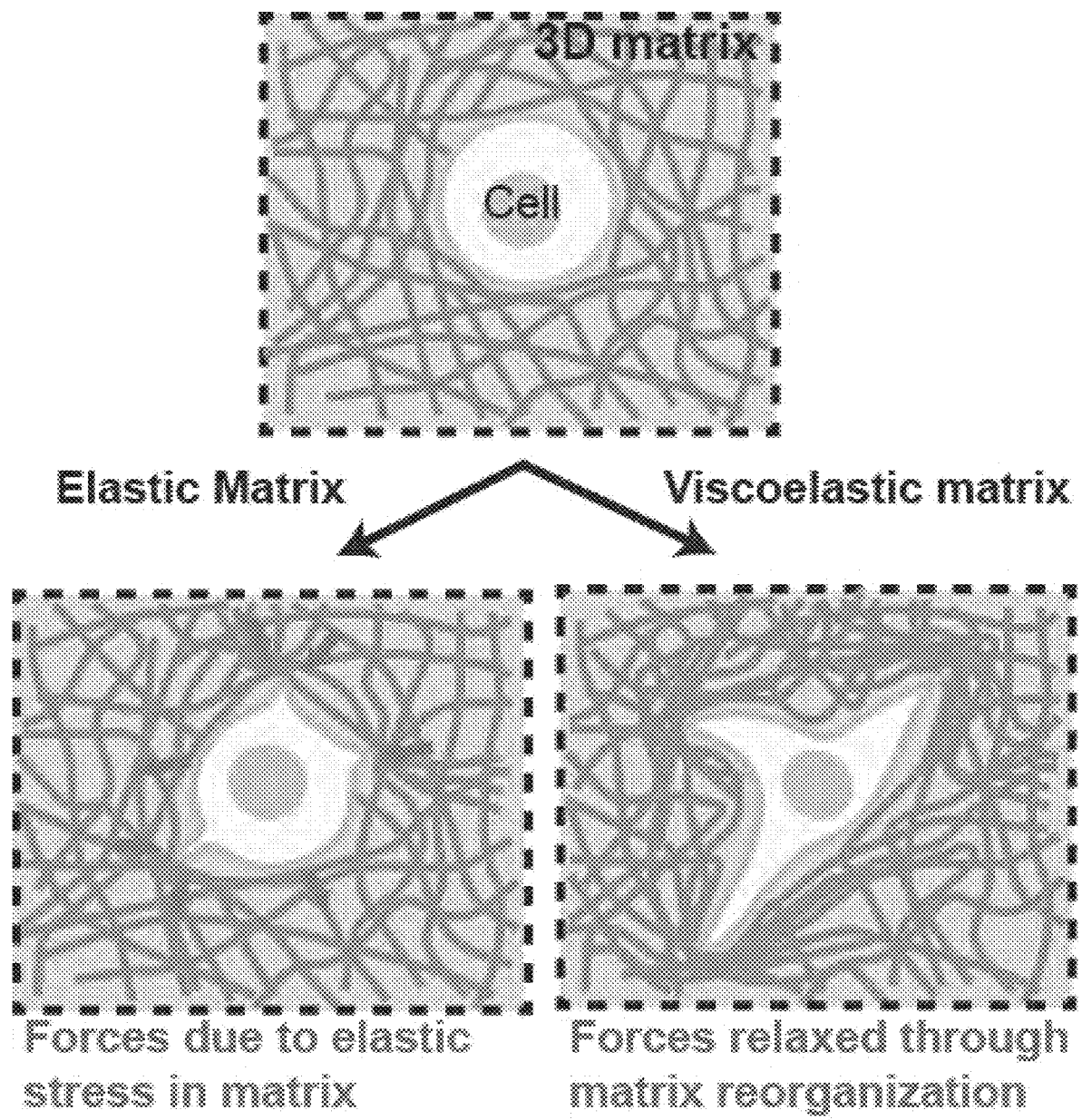

FIG. 5 is a schematic illustrating how altered stress relaxation properties of matrix may allow cell spreading and other behaviors. In an elastic matrix, stresses in the matrix due to protrusions or contractions by cells are maintained over time, restricting cell shape change, proliferation, and other behaviors. In a viscoelastic matrix, stresses in the matrix (e.g., forces against cell contraction or protrusion) are relaxed over time due to mechanical yielding, reorganization, and remodeling of the matrix, allowing cell shape change, proliferation, and other cell behaviors.

Figure 6:
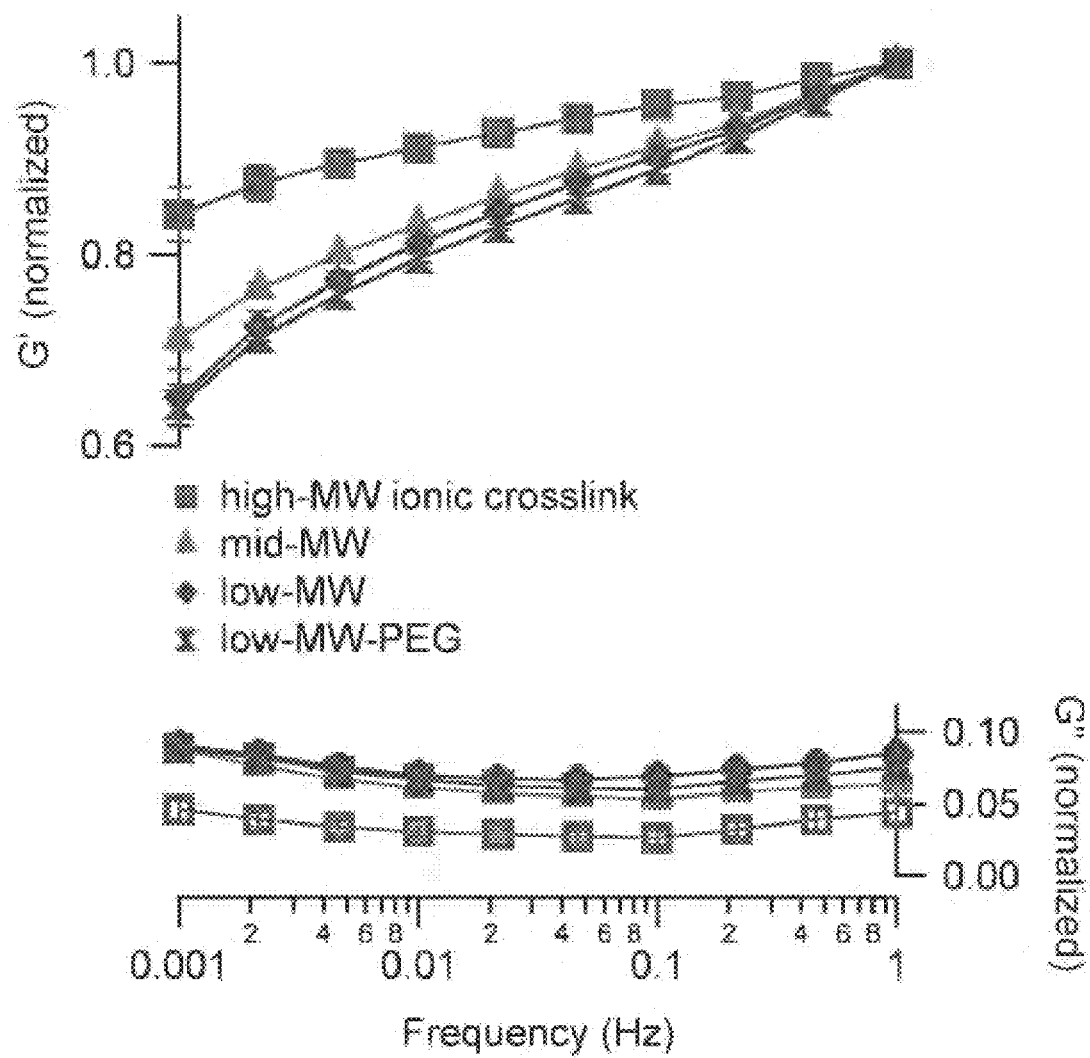

FIG. 6 is a graph of the shear storage (G') and the shear loss (G") modulus of ionically crosslinked alginate hydrogels at 1% strain. The alginates were of different molecular weights, or coupled with a PEG spacer for low MW alginate. All values were normalized by G' for the specific gel at 1 Hz. The rate of decrease of the storage modulus (G') as a function of frequency was greater for lower molecular weight alginate (and also low molecular weight alginate coupled to PEG). In other words, the storage modulus was lower at longer timescales for low molecular weight alginate relative to high molecular weight alginate. This is consistent with the results of the stress relaxation tests. Data are shown as mean+/−s.d, but s.d. is too small to be visible for most data points.

Figure 7:
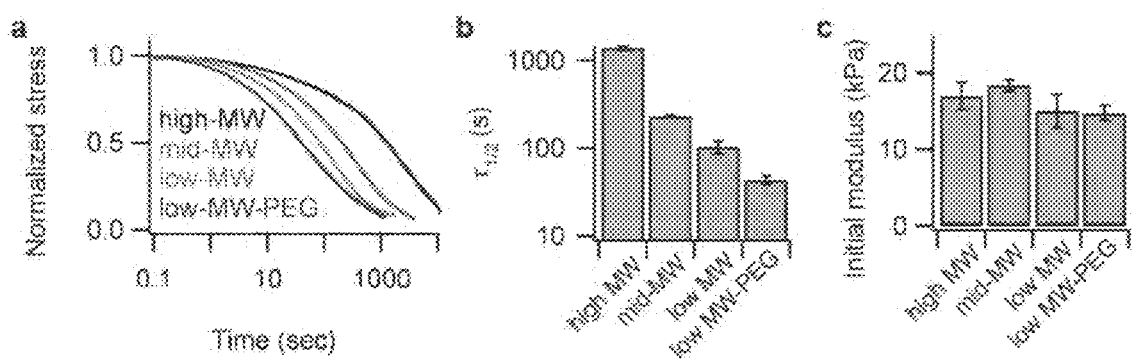

FIG. 7 is a series of graphs showing the results of mechanical characterization of alginate hydrogels with an initial modulus of 17 kPa.

Panel a of FIG. 7 shows the results of stress relaxation tests for alginate hydrogels with an initial modulus of 17 kPa with a compressional strain of 15%.

Panel b of FIG. 7 shows $\tau_{1/2}$ for gels in FIG. 7A. Timescale of stress relaxation decreases significantly with alteration in architecture (Spearman's rank correlation coefficient, p<0.0001).

Panel c of FIG. 7 shows the initial modulus of the gels in FIG. 7A. No significant dependence between initial modulus and matrix architecture is measured, as judged by Spearman's rank correlation test.

Figure 8:
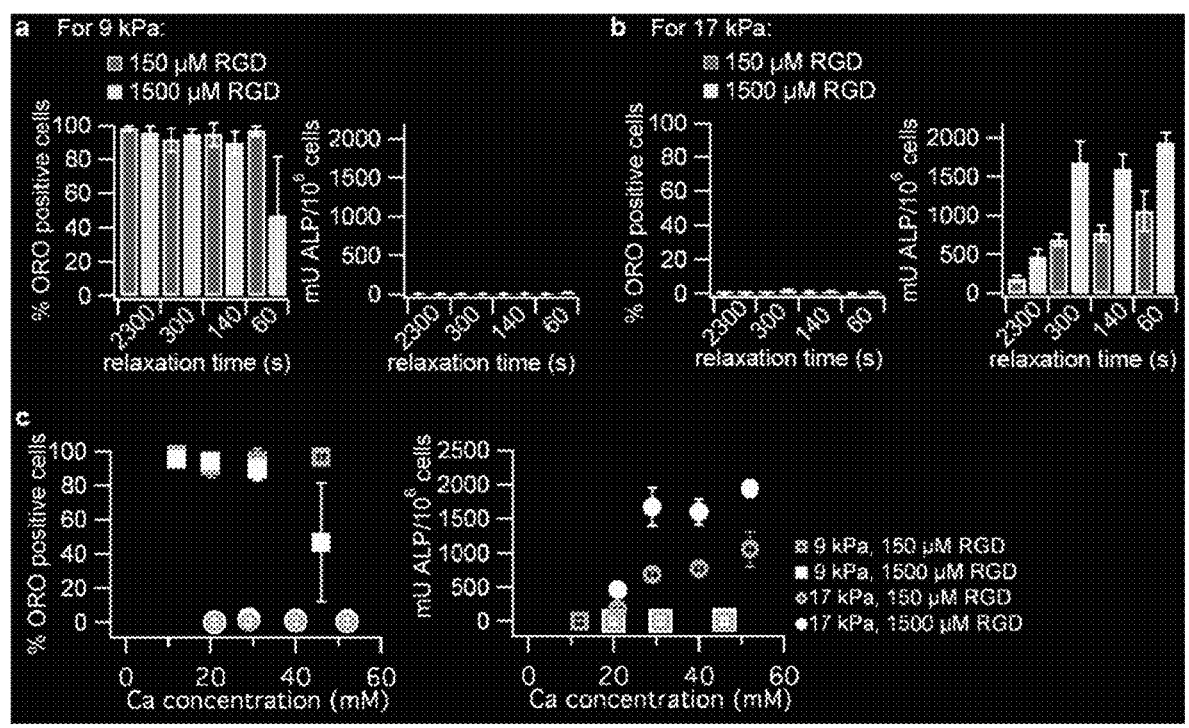

FIG. 8 shows that MSC differentiation is regulated by RGD cell adhesion ligand density but is decoupled from calcium crosslinker concentration.

Panel a of FIG. 8 is a set of bar graphs showing the percentage of cells that stain positive for ORO (left panel), and alkaline phosphatase activity for D1 cells encapsulated in gels with an initial modulus of 9 kPa and different stress relaxation timescales after 7 days in culture, at the indicated RGD ligand densities (right panel).

Panel b of FIG. 8 is a set of bar graphs showing percentage of cells that stain positive for ORO, and alkaline phosphatase activity for D1 cells encapsulated in gels with an initial modulus of 17 kPa and different stress relaxation timescales after 7 days in culture, at the indicated RGD ligand densities. The y-axis ranges in FIGS. 8A-B were set to be equal to facilitate comparison.

Panel c of FIG. 8 is a set of bar graphs showing percentage of cells that stain positive for ORO and alkaline phosphatase activity for D1 cells encapsulated at the indicated conditions as a function of concentration of calcium used to ionically crosslink the alginate polymer chains. There is no correlation between calcium concentration and the extent of differentiation.

Figure 9:
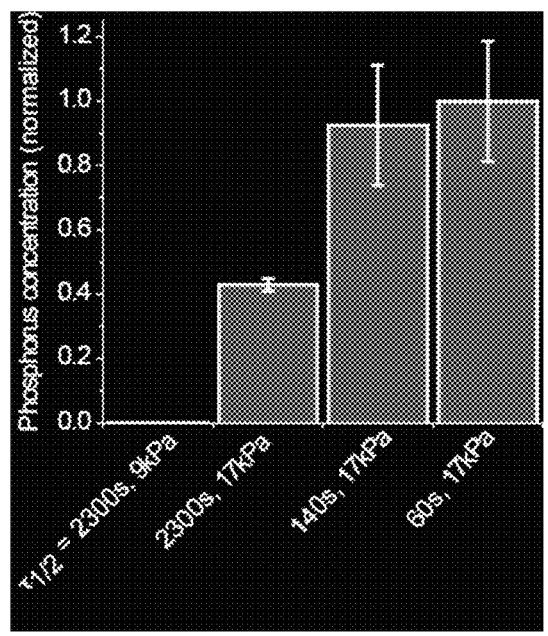
Figure 9:
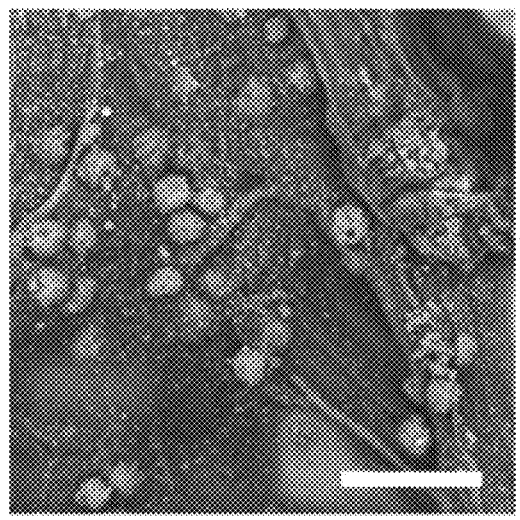
Figure 9:
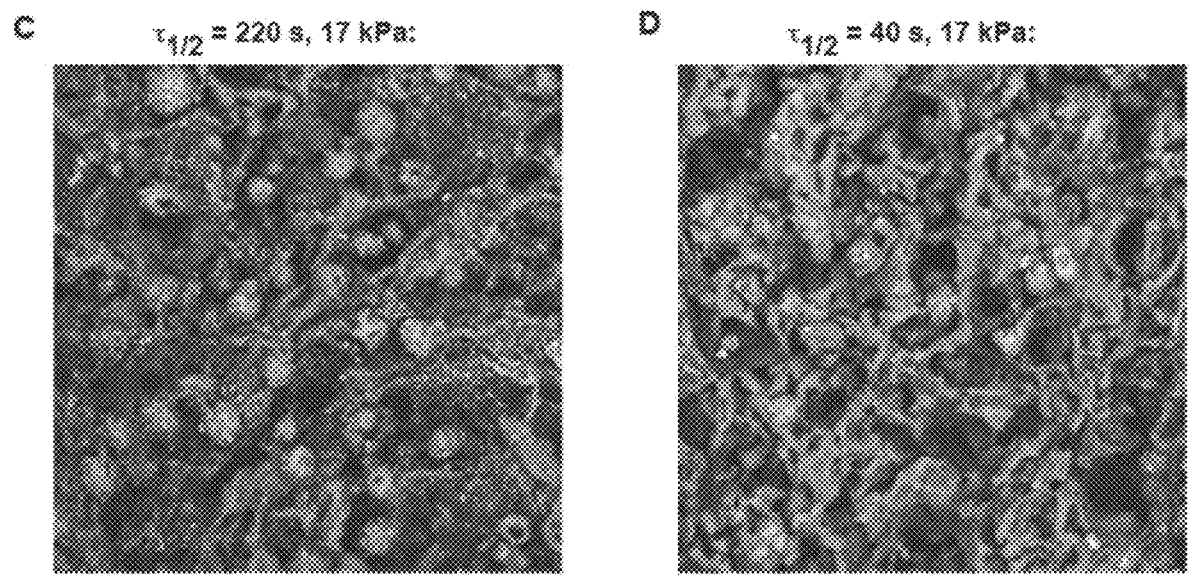

Panel A of FIG. 9 is a bar graph showing the compositional analysis of alginate gels with scanning electron microscope and energy dispersive X-ray spectrometry (SEM-EDS). Phosphorus (P) concentration in cryosections of gels with the indicated conditions (all gels at 1500 µM RGD) after 2 weeks of 3D culture of MSCs. The EDS signal of P is correlated to the quantity of phosphate mineral deposit. The P signal from 9 kPa, $\tau_{1/2}$=2300 s alginate gel (adipogenic condition) is below detection limit and not shown.

Panels B, C and D of FIG. 9 are scanning electron microscope (SEM) images showing the structure and composition of hydrogels. The P elemental maps (P mapped in red) of indicated alginate gel sections is overlaid on their corresponding backscattered SEM images. Scale bar is 50 µm and scale is the same for all images.

Figure 10:
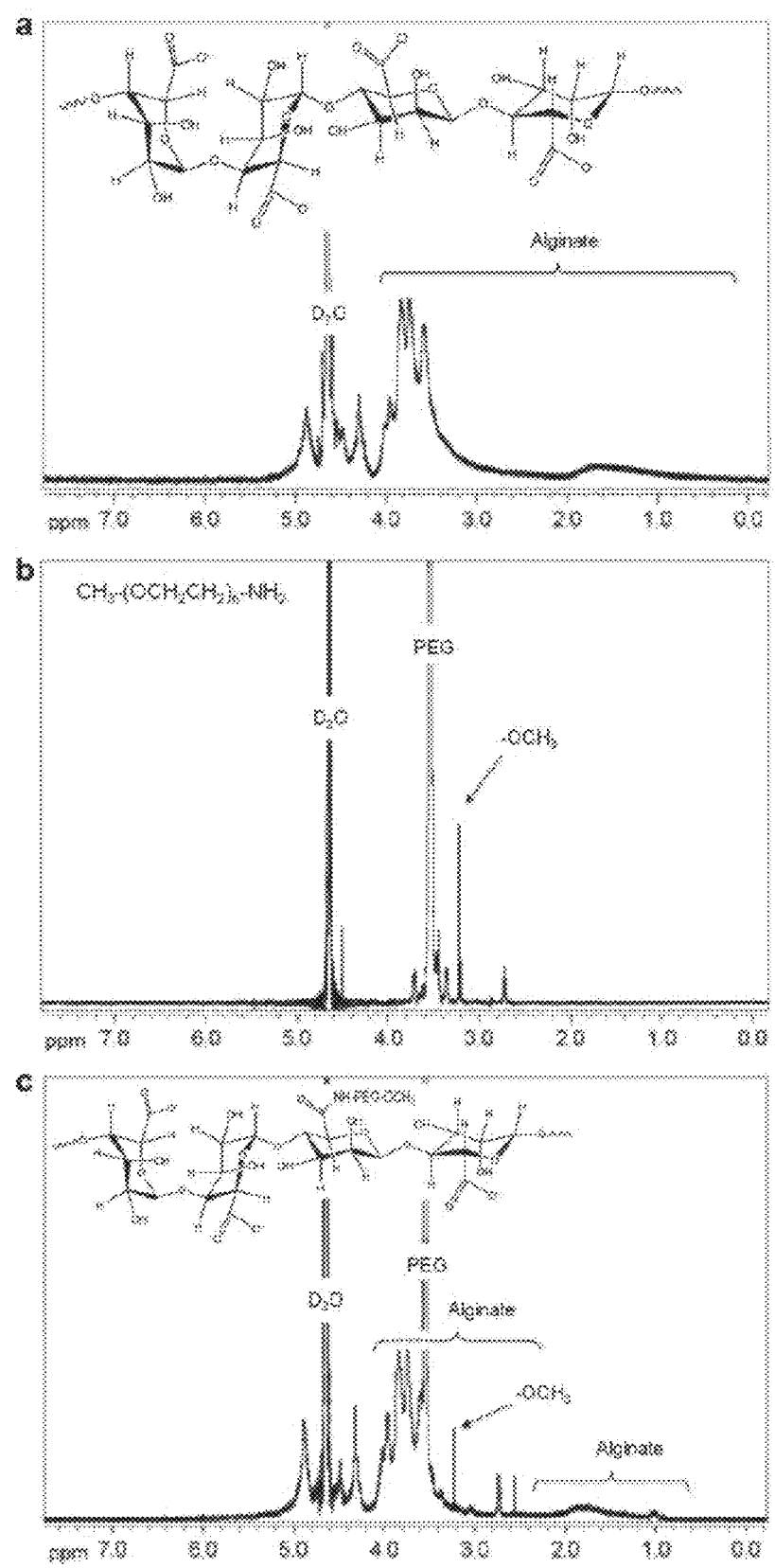

FIG. 10 is a series of panels of $^1$H NMR spectra of PEG coupled alginate.

Panel a of FIG. 10 is a $^1$H NMR spectrum of low molecular weight alginate (35 kDa).

Panel b of FIG. 10 is a $^1$H NMR spectrum of PEG-amine (5 kDa).

Panel c of FIG. 10 is a a $^1$H NMR spectrum of PEG-alginate. Deuterated water (D$_2$O) was used as solvent, and the polymer concentration was 0.5-1% (wt/vol). The efficiency of PEG engraftment was calculated based on the ratio of the integrals for alginate protons to the methyl protons from PEG's terminal methoxy group (δ ~3.2 ppm). PEG-alginate was found to have PEG engraftment of approximately 1.8 PEG per alginate backbone.

Figure 11:
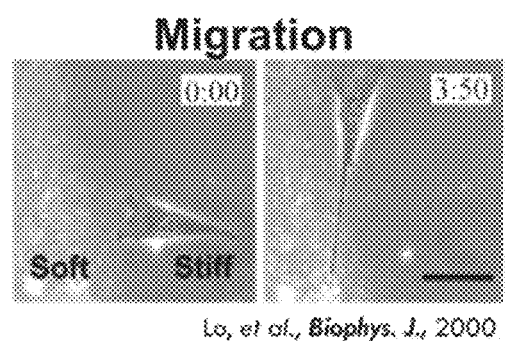
Figure 11:
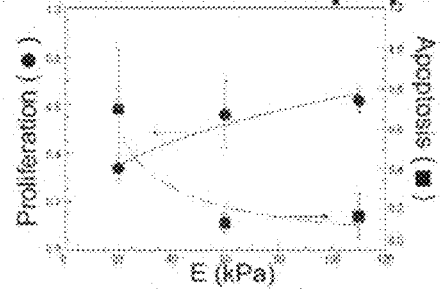
Figure 11:
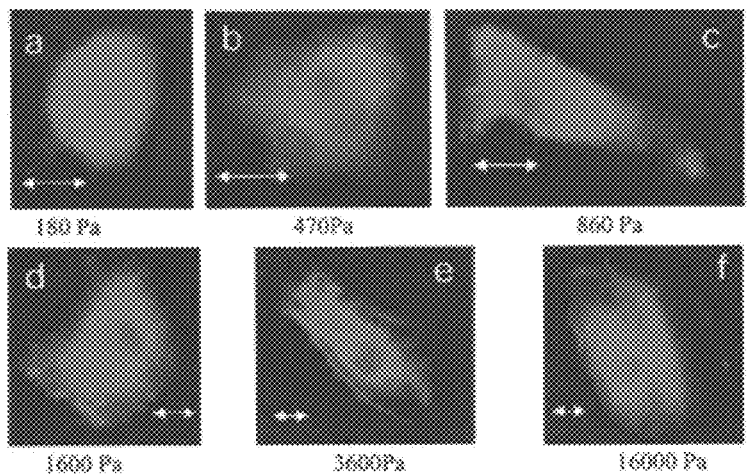
Figure 11:
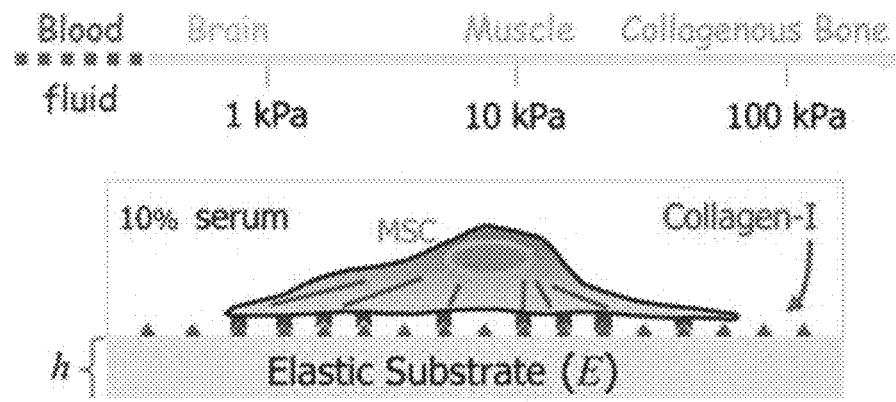

Panel A of FIG. 11 is a set of images showing migration of a cell on soft versus stiff substrates (Lo et al. Biophys. J. 79.1(2000):144-52).

Panel B of FIG. 11 is a graph showing the effect of substrate stiffness on proliferation and apoptosis on cells (Kong et al. Nat. Mat. 4.6(2005):460-5).

Panel C of FIG. 11 is a panel of images showing cell spreading on substrates of different stiffnesses (Yeung et al. Cell Motil. Cyt. 60.1(2005):24-34).

Panel D of FIG. 11 is a schematic showing stem cell differentiation into various lineages depending on stiffness of substrates (Engler et al. Cell. 126.4(2006):677-89).

Figure 12:
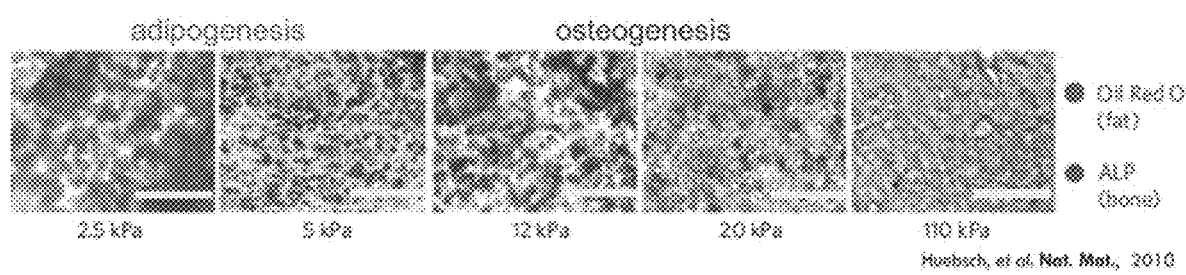

FIG. 12 is a panel of images showing adipogenesis versus osteogenesis of stem cells as a function of stiffness of the substrates (Huebsch et al. Nat. Mat. 2010).

Figure 13:
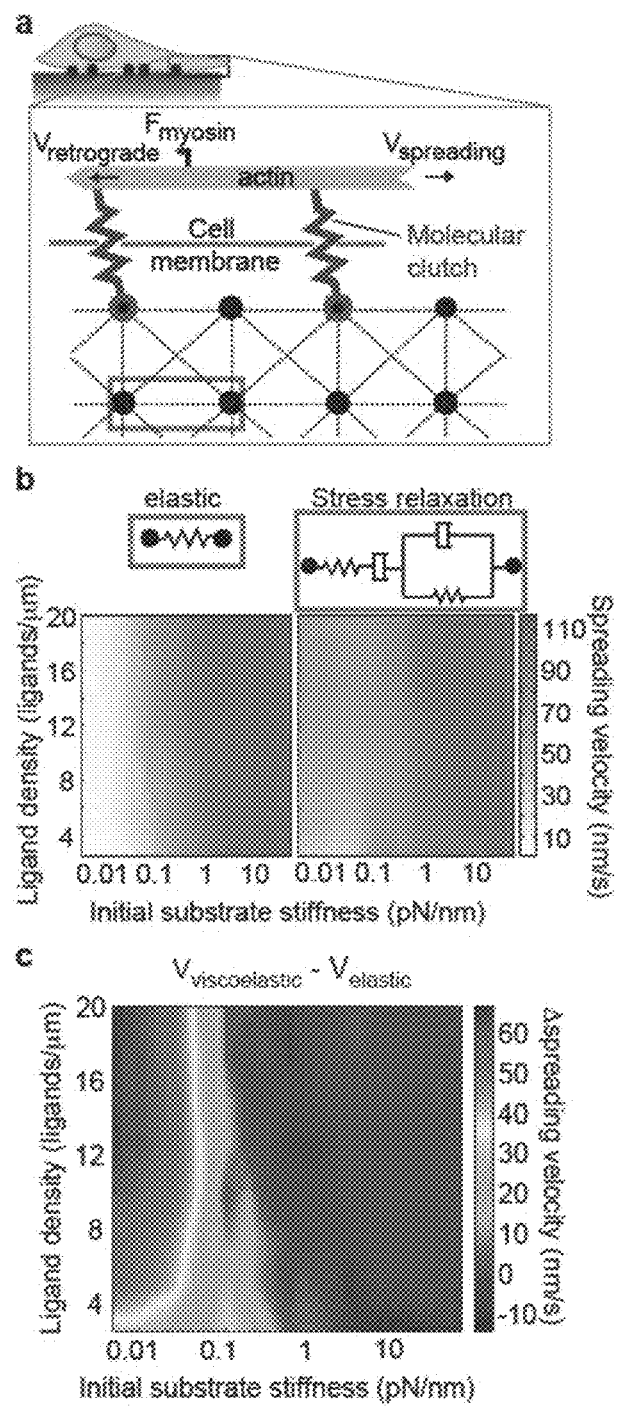

FIG. 13 shows that the stochastic lattice spring model described herein predicts increased cell spreading on viscoelastic substrates that exhibit stress relaxation relative to elastic substrates at low initial stiffness.

Panel a of FIG. 13 is a cartoon depicting a model of cell spreading on elastic or viscoelastic substrates. Actin polymerization at the leading edge of the cell is coupled to the substrate through molecular clutches, and these clutches inhibit retrograde flow of the actin driven by myosin motors. The substrate is modeled as an array of nodes connected by either Hookean springs, representing an elastic substrate, or Burger's model elements, representing a viscoelastic substrate exhibiting stress relaxation.

Panel b of FIG. 13 shows a plot of simulation results for cell spreading velocity on elastic substrates or substrates with stress relaxation as a function of initial substrate stiffness and adhesion ligand density.

Panel c of FIG. 13 is a plot showing the difference in cell spreading velocity for cells on substrates with stress relaxation relative to elastic substrates.

Figure 14:
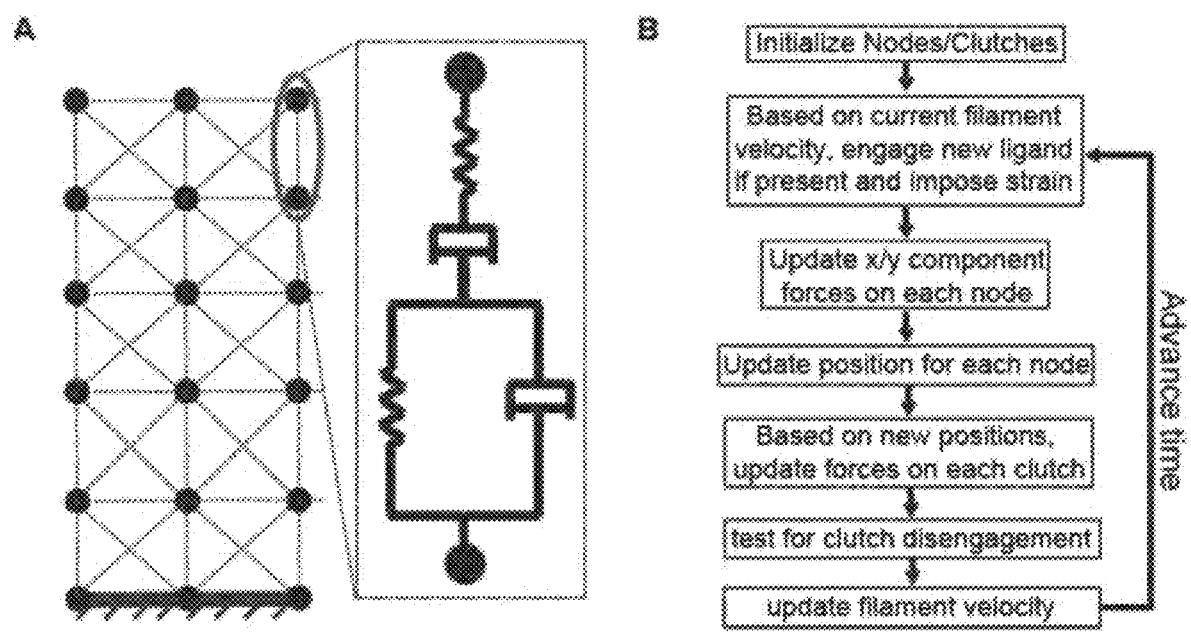

FIG. 14 show formulation of the lattice-spring model described herein.

Panel A of FIG. 14 is a schematic of lattice-spring network used to model the substrate. Simple springs are used as the linkages in a purely elastic case and the four-element Burger's model is used in the viscoelastic case.

Panel B of FIG. 14 is a flowchart depicting the simulation algorithm.

Figure 15:
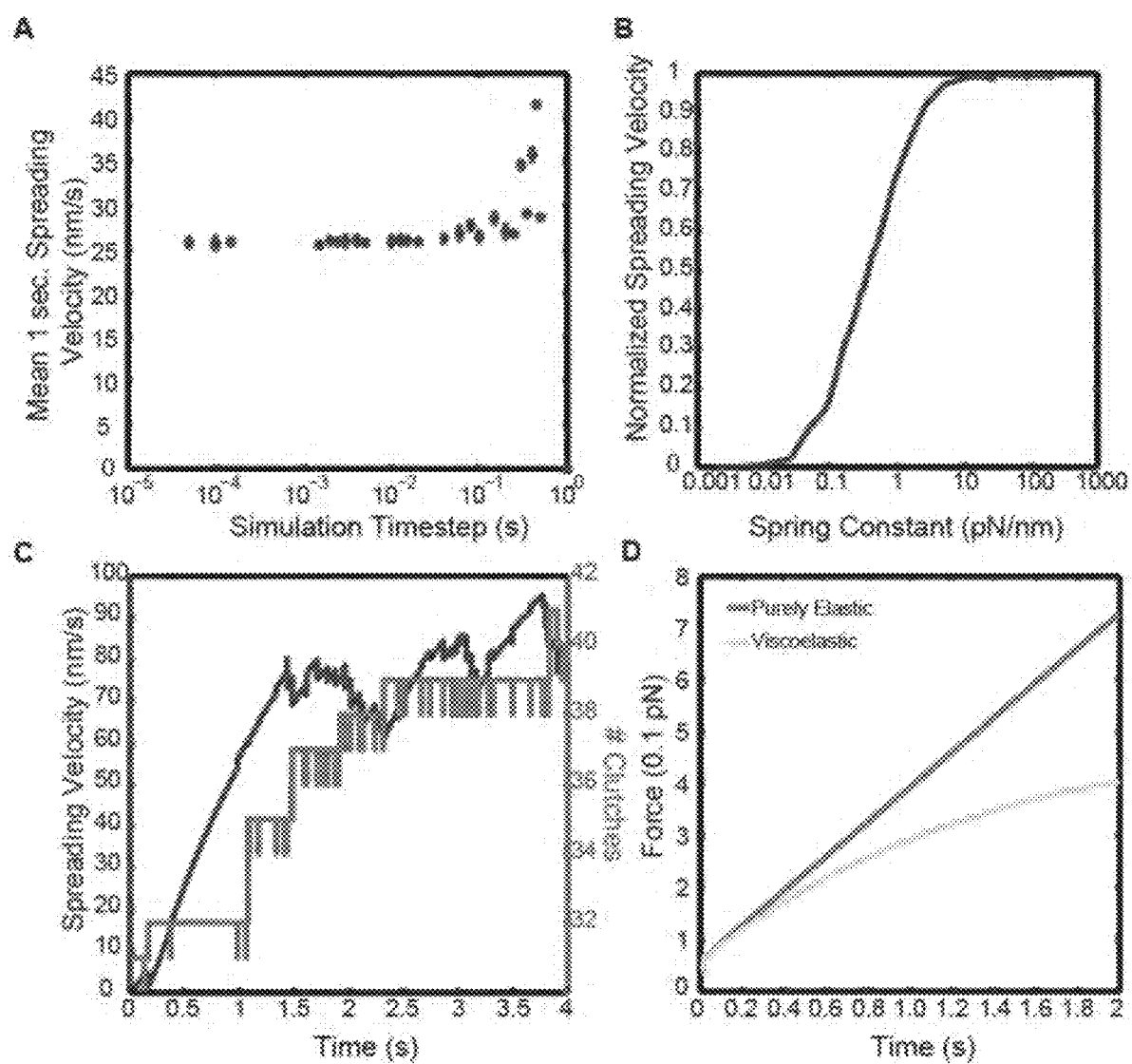

FIG. 15 is a series of graphs illustrating characterization of the model described herein.

Panel A of FIG. 15 is a graph showing the time-step dependence of algorithm. Simulations were run for 1 second in simulation time using various time steps, and the resulting average spreading velocities for 20 simulation runs were recorded. Error bars represent S.D. (n=20).

Panel B of FIG. 15 is a graph showing the average spreading velocity as a function of substrate stiffness if ligand density dependence and substrate lattice are removed. Data is reported as the mean of five simulation runs.

Panel C of FIG. 15 is a graph showing the spreading velocity (blue) and number of molecular clutches (red) for a representative purely elastic substrate (k=1 pN/nm, 0.02 ligands/nm). Spikes are indicative of bond rupture.

Panel D of FIG. 15 is a graph of examplary force/extension curves from simulated tensile testing. Substrates were strained at 0.17 nm/ms and the resulting force in a given linkage was recorded. A representative purely elastic substrate is given in red and a representative viscoelastic substrate is given in green, both at the same initial elastic modulus.

Figure 16:
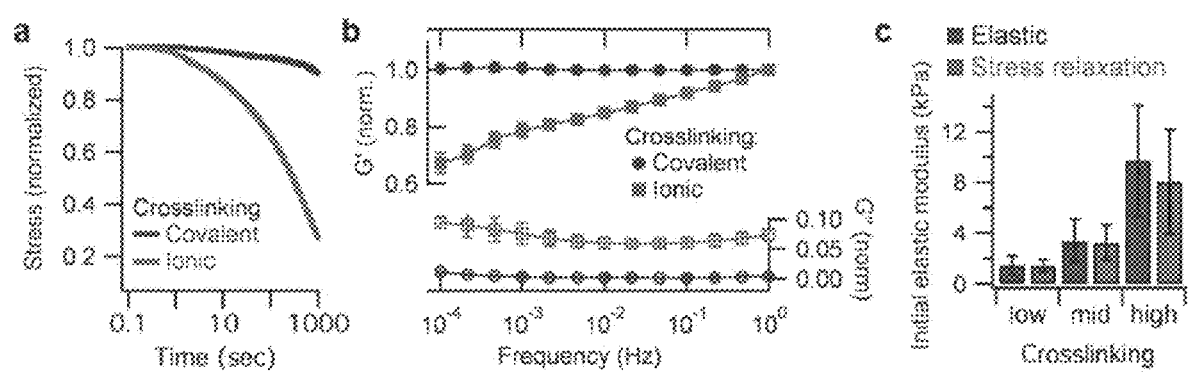

FIG. 16 shows that crosslinking alginate gels covalently or ionically leads to substrates that are either purely elastic or exhibit stress relaxation, respectively.

Panel a FIG. 16 is a graph showing the stress relaxation of covalently and ionically crosslinked alginate gels. Covalent crosslinking led to elastic gels that show little stress relaxation. Ionically crosslinked gels were viscoelastic and exhibited stress relaxation over time under a constant strain.

Panel b of FIG. 16 is a graph showing shear storage and shear loss modulus as a function of frequency for ionically and covalently crosslinked gels. All values are normalized by the shear storage modulus at 1 Hz for that gel.

Panel c of FIG. 16 is a bar graph showing initial Young's modulus of covalently (elastic) or ionically (stress relaxing) crosslinked alginate gels as measured by atomic force microscopy for different concentrations of crosslinker (see Table 3).

Figure 17:
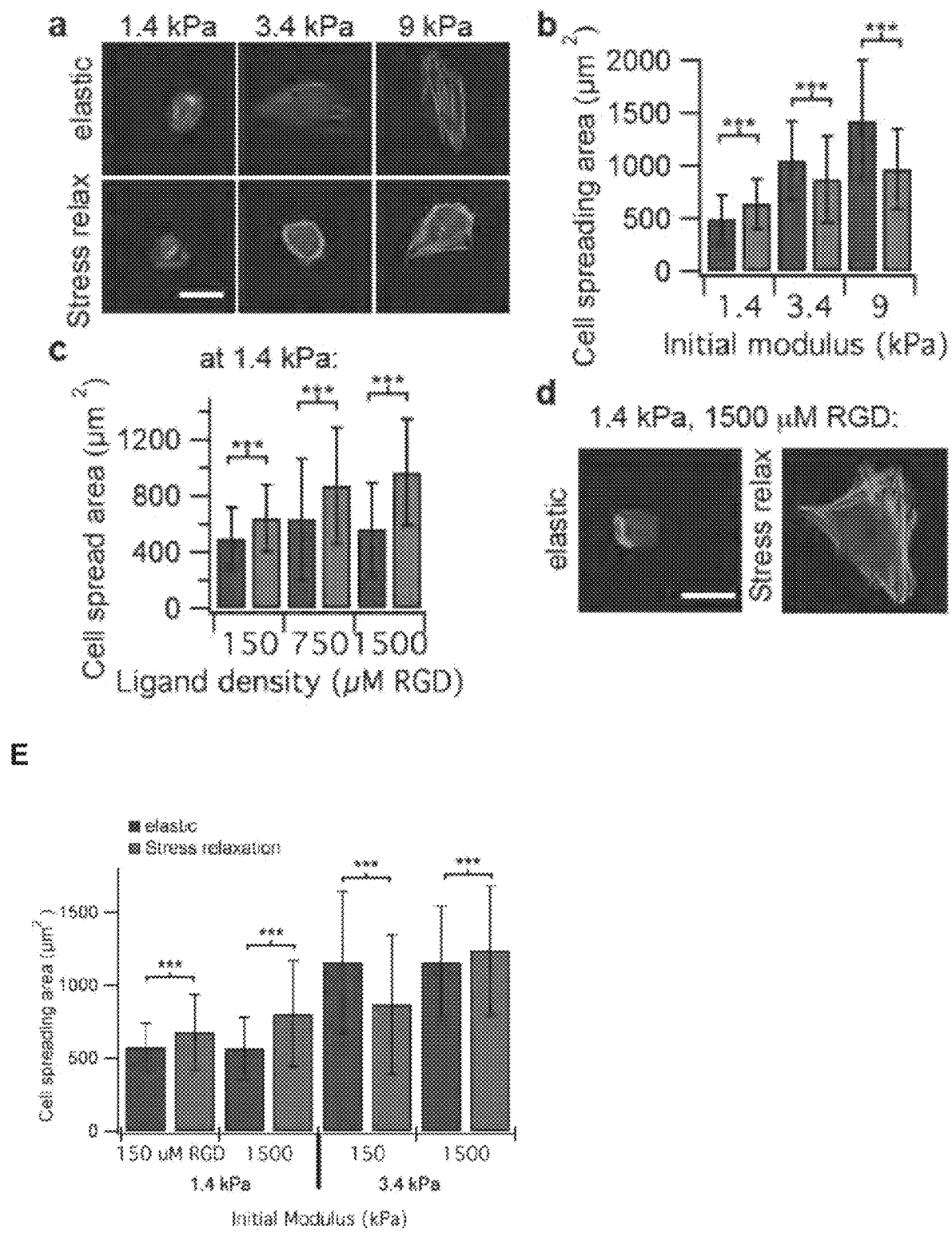

FIG. 17 shows that cell spreading in 2D cultures is enhanced for cultures grown on substrates that exhibit stress relaxation at a low initial elasticity and high ligand density.

Panel a of FIG. 17 is a panel of representative images of cells cultured at the indicated conditions, taken after 20 hours. Actin is depicted in green; nucleus is depicted in blue.

Panel b of FIG. 17 is a bar graph showing the size of cell spreading area as a function of initial modulus for cells on elastic (grey/left-hand bars) or stress relaxing (maroon/right-hand bars) substrates with an RGD density of 150 µM.

Panel c of FIG. 17 is a bar graph showing the size of cell spreading area as a function of RGD ligand density for cells on elastic (grey/left-hand bars) or stress relaxing (maroon/right-hand bars) substrates. The initial modulus is 1.4 kPa for all substrates.

Figure d of FIG. 17 is a panel of representative image of cells plated on substrates with an initial modulus of 1.4 kPa, RGD density 1500 µM, and the indicated stress relaxation behavior.

Panel E of FIG. 17 is a bar graph showing 3T3 cell spreading on 2D substrates that are either elastic or exhibit stress relaxation. Cells were tested on substrates with an initial modulus of either 1.4 kPa or 3.4 kPa. Two RGD concentrations, 150 µM and 1500 µM, were compared on each modulus. Data are shown as mean+/−s.d. *** indicates p<0.001 (Student's t-test).

Figure 18:
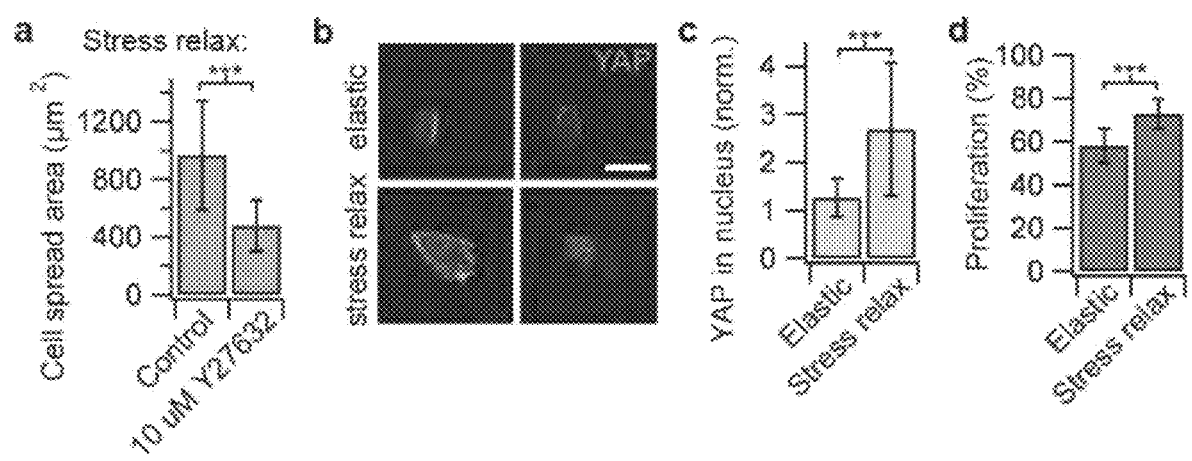

FIG. 18 shows that enhanced cell spreading on substrates with stress relaxation at a low initial elasticity is mediated through actomyosin contractility and associated with increased YAP nuclear localization and proliferation.

Panel a of FIG. 18 is a bar graph showing the size of cell spreading area on substrates with stress relaxation (initial Young's modulus of 1.4 kPa and RGD density of 1500 µM), with and without addition of 10 µM of a Rho associated protein kinase (ROCK) inhibitor (Y27632).

Panel b of FIG. 18 shows immunohistochemical stains of actin (green), nucleus (blue), and YAP (red) for cells cultured on purely elastic or stress relaxing substrates with an initial Young' modulus of 1.4 kPa, and a RGD density of 1500 µM.

Panel c of FIG. 18 is a bar graph showing the ratio of nuclear YAP to cytoskeletal YAP for cells on substrates with an initial modulus of 1.4 kPa, and a RGD density of 1500 µM.

Panel d of FIG. 18 is a bar graph showing % of proliferating cells after 20 hours in culture for cells cultured on substrates with an initial modulus of 1.4 kPa and a RGD density of 1500 µM. Data are all shown as mean+/−s.d. *** indicates p<0.001 (student's t-test). Scale bars are all 25 µm.

Figure 19:
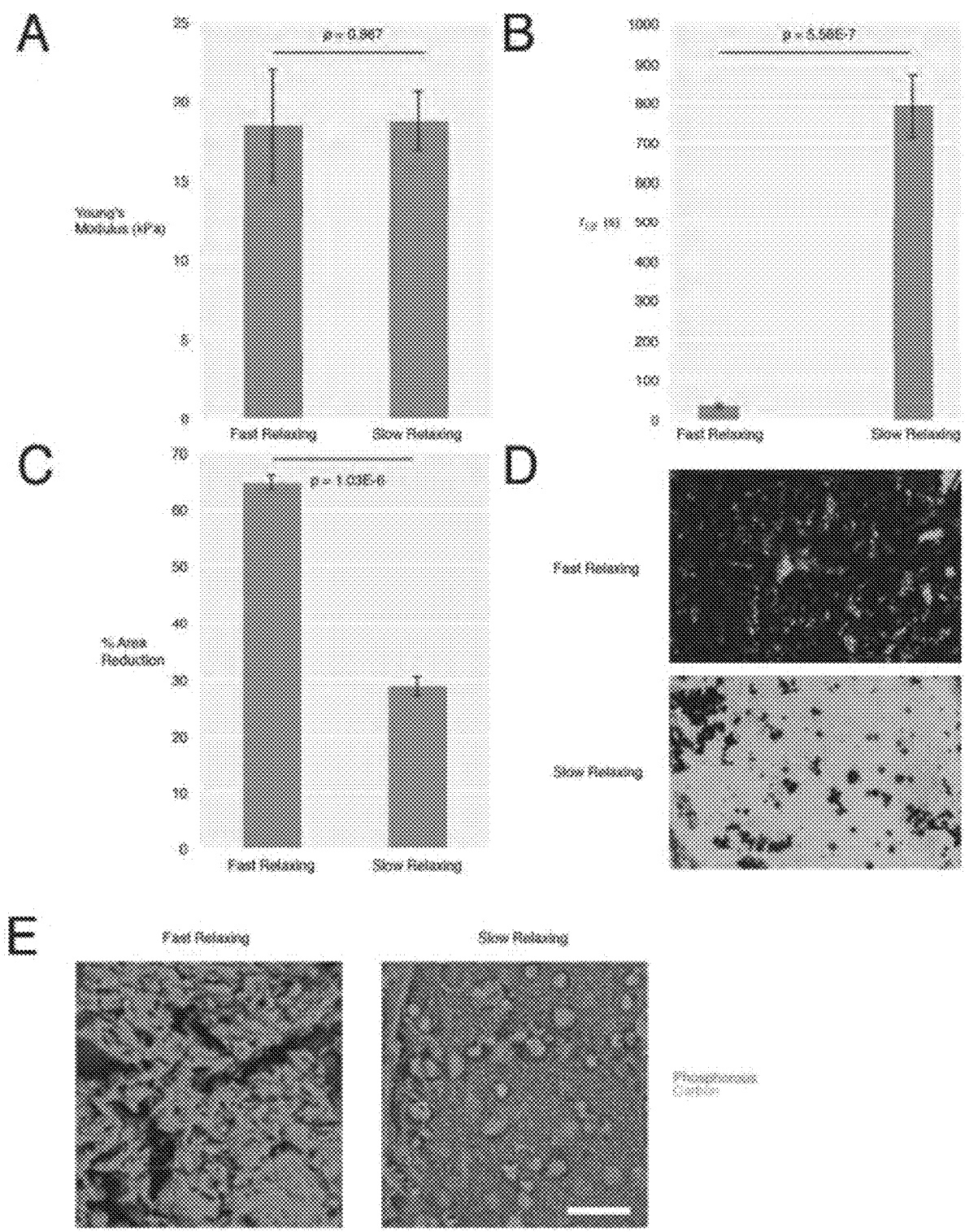

FIG. 19 shows the results of in vitro characterization of alginate hydrogels and their effects on osteogenic differentiation of human MSCs (hMSCs).

Panel A of FIG. 19 is a bar graph depicting the magnitude of Young's modulus as determined by compression testing of slow and fast-relaxing alginate hydrogels (Student's t-test).

Panel B of FIG. 19 is a bar graph showing time to 50% stress relaxation ($\tau_{1/2}$) at 15% strain for slow and fast-relaxing alginate hydrogels (Student's t-test).

Panel C of FIG. 19 is a bar graph showing the extent of gel contraction after culture with encapsulated hMSCs for two weeks. (Student's t-test).

Panel D of FIG. 19 is a panel of images showing representative Von Kossa staining for matrix mineralization between slow and fast relaxing gels with encapsulated hMSCs in osteo-inductive medium after two weeks.

Panel E of FIG. 19 is a panel of representative pseudo-colored EDS elemental maps for slow and fast-relaxing gels with encapsulated hMSCs in osteo-inductive medium after two weeks. Orange depicts phosphorous and marks phosphate deposition, while green depicts carbon.

Figure 20:
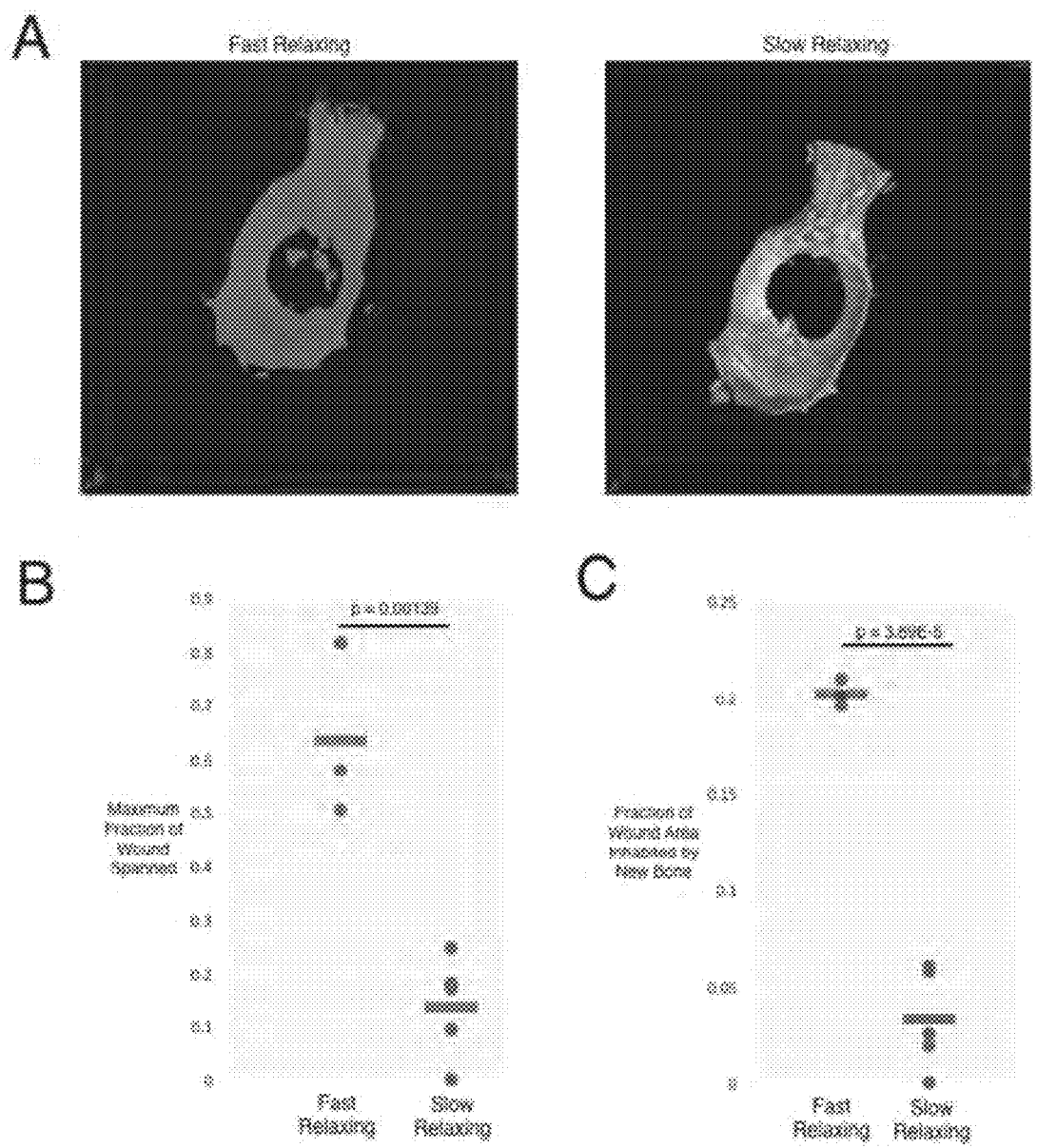

FIG. 20 shows micro-computed tomography analysis of new bone formation after implantation of hydrogels in rat calvarial defect model.

Panel A of FIG. 20 is a panel of representative uCT renderings of rat calvaria three months post-injury. Scale bar—1 cm.

Panel B of FIG. 20 is a graph showin a maximum fraction of the original 8 mm diameter wound spanned after three months (Student's t-test).

Panel C of FIG. 20 is a graph shown fraction of the original wound area inhabited by new bone after three months (Student's t-test).

Figure 21:
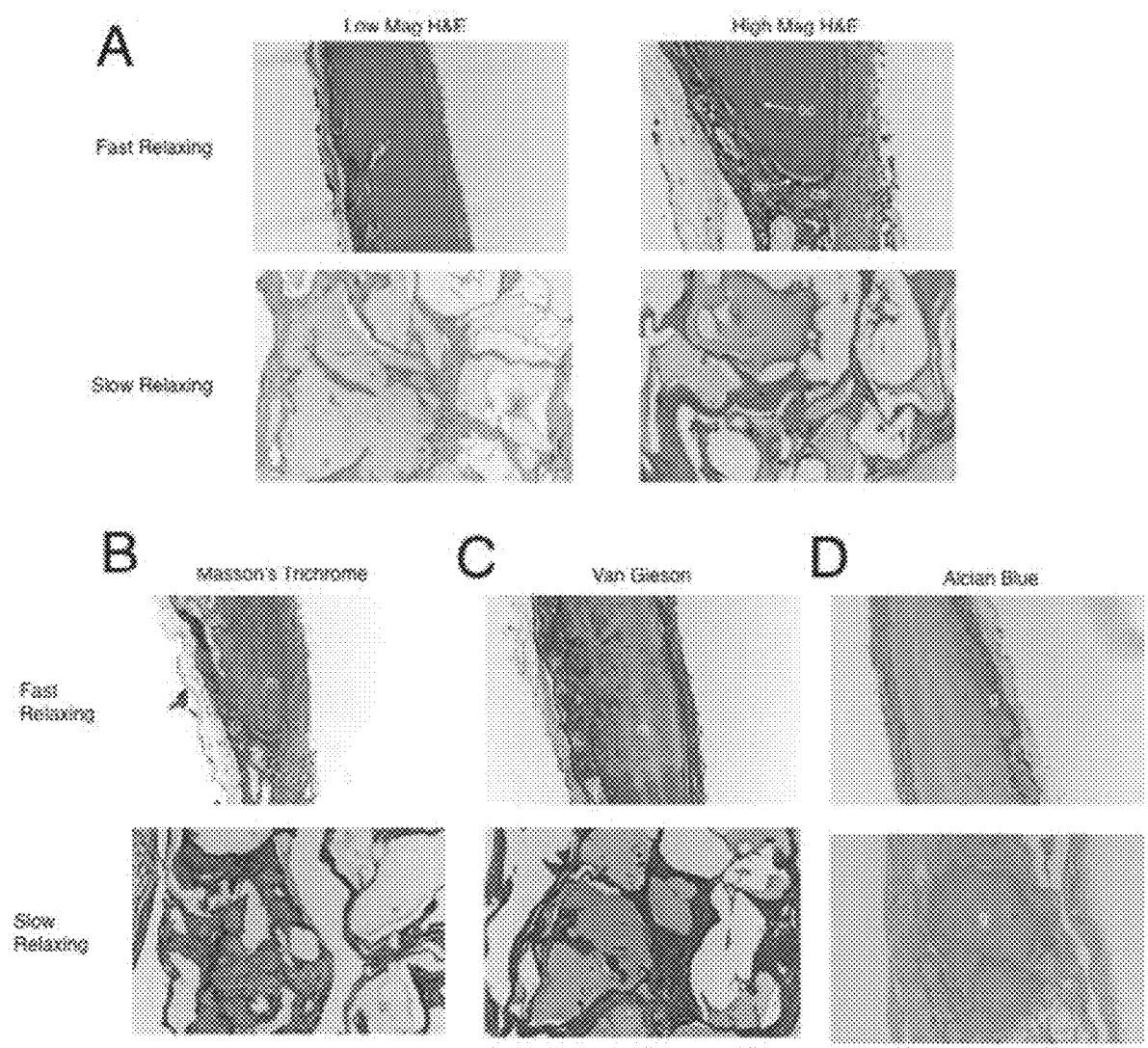

FIG. 21 is a panel of images showing histological staining of calvarial wound sites in rat calvarial defect model three months post-injury.

Panel A of FIG. 21 is a panel of representative Hematoxylin and Eosin staining of new bone in rats implanted with fast-relaxing hydrogels (top panels) and a disorganized environment in rats implanted with slow relaxing hydrogels (bottom panels). The label "OS" indicates the osteoid region, the label "OC" indicates osteocytes, and the label "OB" indicates elongated, activated osteoblasts on the new bone growth front.

Panel B of FIG. 21 is a panel of images showing representative Masson's trichrome staining of mature bone (labeled as "m") in rats implanted with fast-relaxing hydrogels (top panel) and disorganized collagen in rats implanted with slow relaxing hydrogels (bottom panel).

Panel C of FIG. 21 is panel of representative Van Gieson staining of mature bone ("m") in rats implanted with fast-relaxing hydrogels (top panel) and disorganized collagen in rats implanted with slow relaxing hydrogels (bottom panel).

Panel D of FIG. 21 is a panel of representative alcian blue staining of residual alginate hydrogel ("g") showing small remnants in rats implanted with fast-relaxing hydrogels (top panel) and large remnants in rats implanted with slow relaxing hydrogels (bottom panel).

Figure 22:
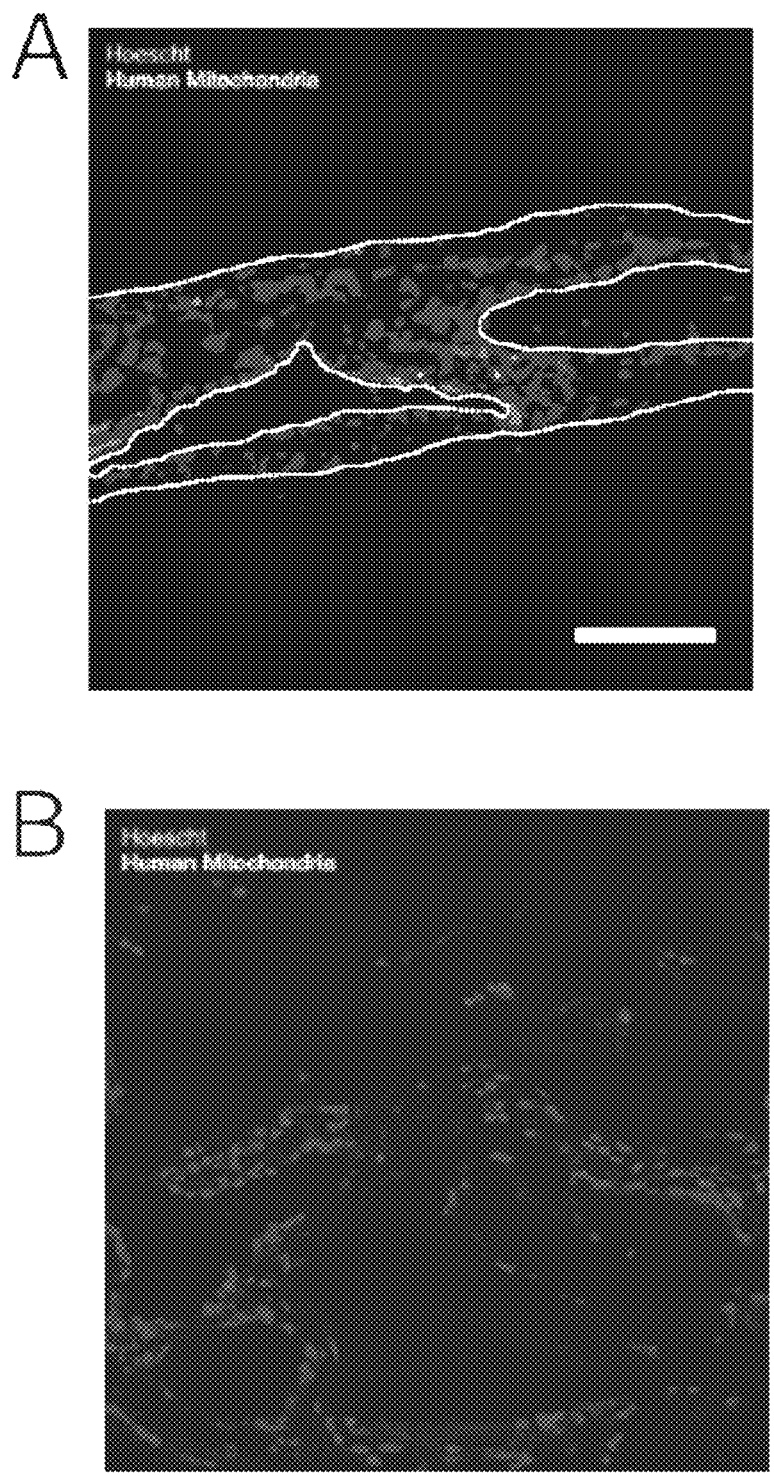

FIG. 22 shows localization of progeny of transplanted cells in calvarial defect site three months postinjury.

Panel A of FIG. 22 is an image of human mitochondrial staining in rats implanted with fast-relaxing hydrogels depicting human cells on the new bone periphery.

Panel B of FIG. 22 is an image of human mitochondrial staining in in rats implanted with slow relaxing hydrogels depicting an absence of human cells.

Figure 23:
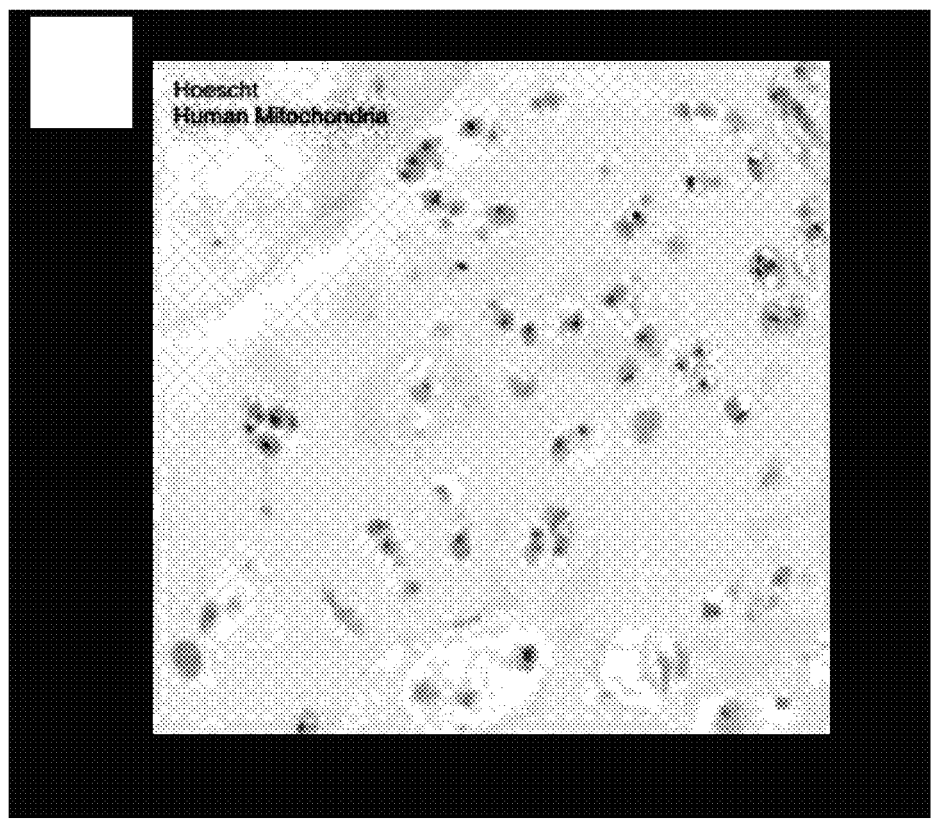

FIG. 23 is an image representing positive control for human mitochondrial staining in human bone section.

DETAILED DESCRIPTION OF THE INVENTION

Hydrogels composed of crosslinked networks of polymers, such as poly-ethylene glycol (PEG) (Raeber, et al., *Biophys. J.* 89, 1374-1388 (2005); Burdick, et al., *Biomaterials* 23, 4315-4323 (2002)), alginate (Rowley, et al., *Biomaterials* 20, 45-53 (1999); Huebsch, et al., *Nat Mater* 9, 518-526 (2010)), and hyaluronic acid (Burdick, et al., *Biomacromolecules* 6, 386-391 (2005); Park, et al. *Biomaterials* 24, 893-900 (2003)), that are covalently coupled to integrin binding ligands, such as RGD, are often used for 3-dimensional (3D) cell culture or as cell-laden biomaterial implants to promote tissue regeneration. The use of these hydrogels is often preferred over reconstituted extracellular matrices of collagen, fibrin, or basement membrane due to the independent control over the physical and chemical properties (e.g. matrix elasticity and ligand density) possible in these hydrogels (Huebsch, et al., *Nat Mater* 9, 518-526 (2010); Peyton, et al., *Biomaterials* 27, 4881-4893 (2006); Khetan, et al., *Nat. Mater.* (2013), doi:10.1038/nmat3586), as well as their homogeneity at the microscale. However, normal cellular processes such as shape change, migration, and proliferation are inhibited in these hydrogels unless they are designed to degrade over time (Raeber, et al. *Biophys. J.* 89, 1374-1388 (2005); Burdick, et al., *Biomacromolecules* 6, 386-391 (2005); Alsberg, et al., *J. Dent. Res.* 82, 903-908 (2003); Huebsch, et al., *Nat Mater* 9, 518-526 (2010)). While non-degradable hydrogels can capture some characteristics of physiological ECM, they are typically almost purely elastic, failing to mimic the viscoelasticity of natural ECM.

In contrast, reconstituted extracellular matrices, such as collagen, or fibrin (Raeber, et al., *Biophys. J.* 89, 1374-1388 (2005)), and various tissues, such as brain (Levental, et al., *Soft Matter* 3, 299-306 (2007)), liver (Liu, et al., *Biorheology* 37, 191-201 (2000)), adipose tissue (Geerligs, et al., *Biorheology* 45, 677-688 (2008)), coagulated bone marrow, or the soft callus of regenerating bone (McDonald, et al., *J. Orthop. Res. Off. Publ. Orthop. Res. Soc.* 27, 1508-1513 (2009)), are all viscoelastic and exhibit stress relaxation, or a decrease in the stress, and thus elastic modulus, over time when a constant strain is applied (FIG. 1A). As the mechanical properties of materials regulate adherent cell behavior (Discher, et al., *Science* 310, 1139-1143 (2005); DuFort, et al., *Nat Rev Mol Cell Biol* 12, 308-319 (2011); Wozniak, et al., *Nat. Rev. Mol. Cell Biol.* 10, 34-43 (2009)), the ability of a substrate to either store (purely elastic) or dissipate (viscoelastic) cellular forces likely provides a powerful cue to interacting cells. In gels that exhibit stress relaxation, each force or strain a cell applies to the matrix over time is initially resisted with a certain stiffness, defined by the initial elastic modulus, followed by a decrease in stiffness due to hydrogel flow (i.e. a mechanical remodeling of matrix) over time as in the stress relaxation tests.

Effects in 3D Cell Cultures

The results described herein show the influence of hydrogel viscoelasticity and stress relaxation on cell biology in 3D culture. In particular, substrate stress relaxation has a profound effect on cell biology, and likely is useful for regeneration, e.g., bone regeneration. Previous studies have highlighted the importance of matrix remodeling through proteolytic degradation on cell function (Page-McCaw, et al., *Nat. Rev. Mol. Cell Biol.* 8, 221-233 (2007)). The altered behavior of cells in rapidly relaxing gels described herein showed that the ability of cells to mechanically remodel their matrix was also an essential component of ECM interactions (FIG. 5). Tissue remodeling involves proteolytic degradation of matrix followed by ECM deposition. Enhancement in cell spreading and proliferation correlated with the ability of the matrix to be mechanically remodeled by cells. The process of differentiation depended strongly upon both the initial elastic modulus and the rate of stress relaxation. Similar to the observed trend of diminishing osteogenic differentiation with decreased stress relaxation, osteogenic differentiation of MSCs was inhibited in non-degradable covalently crosslinked gels, which likely cannot be remodeled mechanically, though differences in polymers, crosslinking chemistries, pore size, ligand densities, and the lack of stress relaxation data precluded a direct comparison (Khetan, et al., *Nat. Mater.* 12(2013):384-386).

Previous work has highlighted the effect of matrix degradation in bone regeneration (Alsberg, et al. *J. Dent. Res.* 82, 903-908 (2003) or cartilage formation (Metters, et al., *Biomed. Sci. Instrum.* 35, 33-38 (1999)) in implantable scaffolds, as well as on cell shape and MSC differentiation in 3D culture in vitro (Khetan, et al., *Nat. Mater.* 12(2013): 384-386). The results described herein demonstrate that the effect of degradation is likely in part due to enhanced matrix stress relaxation in regions of the matrix that exhibit substantial degradation. These results highlight that matrix stress relaxation is a fundamental signal in cell-ECM interactions and mechanotransduction, as most physiological extracellular matrices exhibit some degree of stress relaxation. The findings described herein also exemplify the use of stress relaxation as a design parameter for materials in tissue engineering, particularly in the context of regulating cell proliferation and promoting bone regeneration. The approach to decouple the initial elastic modulus from relaxation rate, and the associated development of rapidly relaxing hydrogels, is useful in a variety of material applications. In addition to promoting bone regeneration and/or osteogenesis, the materials described herein are also useful for the regulation and enhancement of a multitude of cell differentiation and tissue regeneration pathways. For example, the hydrogels described herein mediate adipogenesis, osteogenesis, neurogenesis, and/or chondrogenesis. Tuning or altering the rate of stress relaxation of the hydrogel controls (e.g., enhances of diminishes) cell differentiation. For example, the rate of stress relaxation is altered by varying the type of polymer, by increasing or decreasing the molecular weight of the polymer, by varying the type of spacer molecule, by increasing or decreasing the molecular weight of the spacer, by increasing or decreasing the length of the spacer, by increasing or decreasing the amount of polymer or spacer, by increasing or decreasing the ratio of spacer to polymer, or by using covalent versus noncovalent methods of including the spacer in the hydrogel. In some examples, higher ratios of spacer to polymer (e.g., 2:1 or higher), or lower molecular weight polymers (e.g., 70 kDa or lower, e.g., around 35 kDa) lead to faster stress relaxation. In some cases, a faster rate of stress relaxation (e.g., $\tau_{1/2}$ of 300 seconds or less) can be achieved by using a higher ratio of spacer to polymer (e.g., 2:1 or higher) along with higher molecular weight polymers (e.g., greater than 35 kDa). In other cases, a faster rate of stress relaxation (e.g., $\tau_{1/2}$ of 300 seconds or less) can be achieved by using lower molecular weight polymers (e.g., 70 kDa or lower, e.g., around 35 kDa) combined with any ratio of spacer to polymer. In some cases, the length of the spacer molecule ranges from about 80 Angstroms to about 1500 Angstroms, e.g., about 100 Angstroms to about 1000

Angstroms, e.g., about 250 Angstroms to about 750 Angstroms, e.g., about 500 Angstroms.

For example, as shown by the data presented herein, hydrogels with faster stress relaxation diminish adipogenesis, while hydrogels with faster stress relaxation enhance osteogenesis. The effects of hydrogels on differentiation lineage depend on the substrate stiffness and viscoelasticity of the material. The combination of the rate of stress relaxation and stiffness together determine the effects on differentiation, e.g., diminish or enhance differentiation down particular lineages, such as adipogenesis, osteogenesis, chondrogenesis, or neurogenesis.

Substrate stiffness regulates numerous important biological processes, such as migration, spreading, proliferation, apoptosis, and stem cell differentiation. See, e.g., Lo et al. Biophys. J. 2000; Kong et al. Nature Mat. 2005; Yeung et al. Cell Motil. Cyt. 2005; and Engler et al. Cell 2006. In some cases, mechanistically, e.g., at some length scale, cells gauge resistance to traction forces that they are exerting on a substrate. See, e.g., FIGS. 11A-D.

Huebsch et al. Nat. Mat. 2010 described the effect of stiffness on MSC differentiation, e.g., in alginate hydrogels in 3D. For example, a stiffness/initial elastic modulus of 1-10 kPa led to primarily adipogenesis in MSCs, a stiffness/initial elastic modulus of 11-30 kPa led to primarily osteogenesis of MSCs, where the relaxation time of the hydrogels was about 3300 seconds. See, e.g., FIG. 12.

Living tissues and reconstituted extracellular matrices are viscoelastic and exhibit stress relaxation. See, e.g., FIG. 1A. Many reconstituted ECMs and living tissues are viscoelastic and exhibit stress relaxation. However, many commonly used hydrogels before the present invention were primarily elastic and did not exhibit stress relaxation due to viscoelasticity.

Stress relaxation has effects on cell behavior. The studies described herein investigated whether cells integrate the elastic modulus over time to feel a lower effective modulus, or whether each force/strain a cell exerts resists with initial stiffness, which is relaxed over time by matrix flow (i.e., the cell can mechanically reorganize the matrix). As shown in the Examples, cells reorganize the matrix of the hydrogels presented herein. In some cases, cells do not integrate the elastic modulus over time.

The results presented herein show that both initial elastic modulus and stress relaxation regulate stem cell (e.g., MSC) differentiation. 3D hydrogels with an initial elastic modulus of about 9 kPa led primarily to adipogenesis, while hydrogels with an initial elastic modulus of about 17 kPa led primarily to osteogenesis. Osteogenesis was enhanced with faster stress relaxation of the hydrogel. See, e.g., FIGS. 3A-B. In addition, bone forming activity of osteogenically differentiated MSCs was enhanced with faster stress relaxation. Two main structural features of bone are type-1 collagen and phosphorus containing mineral deposits. The hydrogels described herein, e.g., at about 17 kPa and with a rapid stress relaxation time ($\tau_{1/2}$ of about 1 min) led to the formation of interconnected, mineralized, collagen-1 rich matrix. Such mineralization and collagen-1 formation was not observed in hydrogels with slower stress relaxation times. See, e.g., FIGS. 3A-D. Thus, stress relaxation properties influence both the fate and bone-forming activity of differentiated MSCs.

Effects in 2D Cell Cultures

The results presented herein also demonstrate an effect in 2D cell cultures of stress relaxation on cell behavior. Prior to the invention, studies of cellular mechanotransduction had converged upon the idea that cells sense ECM elasticity by gauging resistance to the traction forces they exert on the ECM, and found that cell spreading, proliferation, osteogenic differentiation, and nuclear localization of the transcriptional regulator YAP were all suppressed on soft substrates. However, these studies typically utilized purely elastic materials as substrates, whereas physiological ECM are viscoelastic, and exhibit stress relaxation, so that cellular traction forces exerted by cells remodel the ECM. By investigating the influence of ECM stress relaxation on cell behavior through computational modeling and cellular experiments, the computational model and results presented herein show that cells cultured on soft substrates that exhibit stress relaxation respond as if the substrate was stiff, with cell spreading, nuclear translocation of YAP, and proliferation all enhanced in 2D cultures. These findings were unexpected, given the previous view of how cells sense and respond to the ECM.

Mechanical properties of ECM play an important role in regulating cell behaviors in development, tissue homeostasis, and disease. See, e.g., Mammoto et al. Dev. Camb. Engl. 137, 1407-1420 (2010); DuFort et al. Nat. Rev. Mol. Cell Biol. 12, 308-319 (2011); Vogel et al. Nat. Rev. Mol. Cell Biol. 7, 265-275 (2006); Discher et al. Science 310, 1139-1143 (2005); and Wozniak et al Nat. Rev. Mol. Cell Biol. 10, 34-43 (2009). Previous studies investigating the influence of substrate elasticity on biological processes typically utilized 2D surfaces of collagen or fibronectin coated polyacrylamide gels as substrates for cell culture. These studies described that cell spreading, proliferation, and nuclear localization of the transcriptional regulator YAP are all suppressed on soft substrates. See, e.g., Engler et al. Biophys. J. 86, 617-628 (2004); Yeung et al. Cell Motil. Cytoskeleton 60, 24-34 (2005); Klein et al. Curr. Biol. CB 19, 1511-1518 (2009); and Dupont et al. Nature 474, 179-183 (2011). The mechanistic understanding from previous studies was that cells sense substrate elasticity by gauging resistance to the traction forces the cells exert on the substrate. See, e.g., Trappmann et al. Nat. Mater. 11, 642-649 (2012); and Swift et al. Science 341, 1240104 (2013). However, the covalent crosslinking of these polyacrylamide hydrogels resulted in purely elastic substrates with a time independent storage or elastic modulus. See, e.g., Cameron et al. Biomaterials 32, 5979-5993 (2011). Correspondingly, deformations of the polymer matrix in previous studies were elastic, not plastic, so that resistance to traction forces exerted by cells was constant over time, and elastic energy was stored in the substrate. See, e.g., Dembo et al. Biophys. J. 76, 2307-2316 (1999).

In contrast, reconstituted extracellular matrices, such as collagen, or fibrin, and many tissues, exhibit stress relaxation, or a decrease in the storage or elastic modulus over time when a constant strain is applied. See, e.g., Raeber et al. Biophys. J. 89, 1374-1388 (2005); Levental et al. Soft Matter 3, 299-306 (2007); Liu et al. Biorheology 37, 191-201 (2000); and Geerligs et al. Biorheology 45, 677-688 (2008). On such matrices, the resistance to cellular traction forces is likely relaxed over time due to reorganization and remodeling of the matrix, dissipating the energy that cell-generated forces imparted into the material. While presented to cells under physiological conditions, the influence of substrate stress relaxation on cell behavior was previously unknown.

The results presented herein on 2D cultures demonstrate that, parallel to the stiffness, substrate stress relaxation is a fundamental physical property of model ECM that has a profound impact on cell behavior and function. Specifically, the effect of stress relaxation was mediated through integrin adhesions and actomyosin based contractility, and increased stress relaxation drove nuclear translocation of YAP. Increased stress relaxation could compensate for matrices with a lower stiffness. Cell spreading and proliferation were increased on substrates with stress relaxation, compared to elastic substrates with the same initial elastic modulus. Cells responded to stress relaxation on the order of minutes (FIG. 16A). This observation is consistent with previous studies of reorganization of the actin cytoskeleton in response to mechanical cues that initiated within seconds, and, in the case of cell spreading, equilibrated over minutes to hours. See, e.g., Vogel et al. *Nat. Rev. Mol. Cell Biol.* 7, 265-275 (2006); Zhang et al. *Nat. Cell Biol.* 10, 1062-1068 (2008); and Mooney et al. *J. Cell Sci.* 108 (Pt 6), 2311-2320 (1995).

Previous studies with cells cultured on purely elastic substrates have found that the stored elastic energy increases with the substrate modulus due to an increase in cellular traction stress, but it was unclear how this translates to viscoelastic substrates. See, e.g., Discher et al. *Science* 310, 1139-1143 (2005); and Ghosh et al *Biomaterials* 28, 671-679 (2007). One possibility was that the dissipation of energy through matrix yielding, and resultant decrease in stored energy, allowed cells to generate more work on viscoelastic substrates relative to purely elastic substrates of the same elasticity—thereby enabling spreading. Alternatively and unexpectedly, the model described below shows that this behavior is likely an intrinsic result of molecular clutch based adhesions. One study showed that an increase in the loss modulus of polyacrylamide substrates led to increased cell spreading. See, e.g., Cameron et al. *Biomaterials* 32, 5979-5993 (2011). However, due to the covalent crosslinking and an associated time independent storage modulus of these substrates, as well as possible alterations in pore size arising from the method used to alter the loss modulus (Trappmann et al. *Nat. Mater.* 11, 642-649 (2012)), the mechanism for enhanced cell spreading differs from that described in the Examples below.

On soft viscoelastic substrates in 2D culture, mechanotransduction is not solely mediated through cells sensing resistance to traction forces. Since physiological extracellular matrices typically exhibit various degrees of stress relaxation, this result highlights the importance of considering matrix stress relaxation as a fundamental property of the ECM that is critical to understanding the basics of cell-ECM interactions and the underlying biophysics of mechanotransduction.

In both 2D and 3D cultures, the results presented herein show that cell spreading and proliferation were increased with faster rates of stress relaxation. This finding was unexpected and surprising, as it was counter to what was expected from previous models of mechanotransduction. For example, it was surprising that gels that relax quickly (relative to other substrates) increased differentiating of stem cells, e.g., MSCs, to an osteogenic lineage and promoted bone formation in vivo in a rat calvarial defect model. It was also surprising that an alginate polymer chain that is coupled to a spacer molecule that does not cross-link two alginate polymer chains can be used to produce a hydrogel that is characterized by a particularly fast stress relaxation rate.

Hydrogels of the Invention

The present invention provides a fast relaxing hydrogel comprising a plurality of alginate polymer chains and a plurality of spacer molecules, wherein the plurality of alginate polymer chains are ionically cross-linked to each other; wherein each of the plurality of spacer molecules comprises a first end and a second end, wherein the first end is attached to an alginate polymer chain and the second end is not attached to an alginate polymer chain; and wherein the hydrogel is characterized by a fast stress relaxation rate ($\tau_{1/2}$).

A "fast relaxing hydrogel", as defined herein, includes a hydrogel that exhibits a fast relaxation behavior when stress is applied to the hydrogel. The fast relaxing hydrogel is characterized by a stress relaxation rate ($\tau_{1/2}$) of 1000 seconds of less, e.g., 950, 900, 850, 800, 750, 700, 650, 600, 550, 500, 450, 400, 350, 300, 250, 200, 150, 100, 80, 60, 40, 20, 10, 9, 8, 7, 6, 5, 4, 3, 2, 1 seconds or less. The fast relaxing hydrogel may be characterized by a stress relaxation rate ($\tau_{1/2}$) of about 500 to about 1000, about 700 to about 900, about 400 to about 750, about 500 to about 600, about 200 to about 400, about 300 to about 450, about 100 to about 250, about 90 to about 150, about 80 to about 100, about 60 to about 85, about 45 to about 70, about 20 to about 50, about 35 to about 55, about 10 to about 25, about 1 to about 15, or about 0.1 to about 5 seconds.

A "fast stress relaxation rate", as defined herein, is a stress relaxation rate ($\tau_{1/2}$) of 1000 seconds of less, e.g., 950, 900, 850, 800, 750, 700, 650, 600, 550, 500, 450, 400, 350, 300, 250, 200, 150, 100, 80, 60, 40, 20, 10, 9, 8, 7, 6, 5, 4, 3, 2, 1 seconds or less. The fast relaxing hydrogel may be characterized by a stress relaxation rate ($\tau_{1/2}$) of about 500 to about 1000, about 700 to about 900, about 400 to about 750, about 500 to about 600, about 200 to about 400, about 300 to about 450, about 100 to about 250, about 90 to about 150, about 80 to about 100, about 60 to about 85, about 45 to about 70, about 20 to about 50, about 35 to about 55, about 10 to about 25, about 1 to about 15, or about 0.1 to about 5 seconds.

A "slow relaxing hydrogel", as defined herein, includes a hydrogel that is characterized by a stress relaxation rate ($\tau_{1/2}$) of greater than 1000 seconds. Methods for measuring stress relaxation rate ($\tau_{1/2}$) of a hydrogel are well known in the art.

The present invention also provides a hydrogel comprising a plurality of polymer chains, e.g., alginate polymer chains. The polymer chains may have a molecular weight of less than 250 kDa or less, e.g., 240, 230, 220, 210, 200, 190, 180, 170, 160, 150, 140, 130, 120, 110, 100, 95, 90, 85, 80, 75, 70, 65, 60.55, 50, 45, 40, 35, 30, 25, 20, 15, 10, 5 or 1 kDa or less.

The stress relaxation of a material determines how polymers in the material relieve stress under constant strain. In some examples, the hydrogel is characterized by a stress relaxation rate ($\tau_{1/2}$) of 1000 seconds or less, e.g., 1000, 900, 800, 700, 600, 500, 400, 300, 200, 100, 80, 60, 40, 20, 10, 9, 8, 7, 6, 5, 4, 3, 2, 1 seconds or less). In one example, the hydrogel is characterized by a stress relaxation rate ($\tau_{1/2}$) of about 1 min. The stress relaxation behavior of the hydrogel may be adjusted to mimic what is similar in natural biological tissues, e.g., fracture callus and/or coagulated bone marrow.

In some cases, the hydrogel is characterized by an initial elastic modulus of about 1-30 kPa, e.g., about 1-10 kPa, or about 11-30 kPa, e.g., about 9 kPa, or about 17 kPa. For example, the hydrogel is characterized by an initial elastic modulus of about 17 kPa or about 9 kPa.

The stiffness and viscoelasticity of materials, such as the hydrogels described herein, are determined by applying a stress (e.g., oscillatory force) to the material and measuring the resulting displacement (i.e., strain). For an applied oscillatory stress or strain, the stress and strain occur in phase in purely elastic materials, such that the response of one (stress or strain) occurs simultaneously with the other. In purely viscous materials, a phase difference is detected between stress and strain. The strain lags behind the stress by a 90 degree (radian) phase lag. Viscoelastic materials have behavior in between that of purely elastic and purely viscous—they exhibit some phase lag in strain. The storage modulus in viscoelastic solid materials is a measure of the stored energy, representing the elastic portion, while the loss modulus in viscoelastic solids is a measure the energy dissipated as heat, representing the viscous portion. The hydrogels described herein are characterized as viscoelastic.

The elastic modulus (also called Young's modulus) is a measure of stiffness of a material, such as a hydrogel. The elastic modulus is the slope of the initial straight portion, e.g., the first 5-10% of strain, of a stress-strain curve. The modulus is the ratio of the change in stress to the change in strain expressed as a fraction of the original length. The elastic modulus has units of Pa (or $N/m^2$ or $m^{-1} \cdot kg \cdot s^{-2}$). For viscoelastic materials, the measured elastic modulus can depend on the timescale of the stress-strain measurement, since viscoelastic materials can exhibit stress relaxation leading to a decrease in the measured modulus for measurements taken over longer timescales. For materials that exhibit significant stress relaxation, the initial elastic modulus is defined as the elastic modulus for a stress-strain measurement that is performed over a timescale at which there is minimal stress relaxation. The initial elastic modulus can be determined using standard methods available in the art, e.g., by a compression test or rheology. For example, a hydrogel is compressed, e.g., to 15% strain, e.g., with a deformation rate of about 1 mm/min. With 15% compression, the stress versus strain relations of the hydrogels are almost linear, and the slope of the initial portion (first 5-10% strain) of the stress strain curves gives the initial elastic modulus.

Exemplary polymers suitable or use in the hydrogels of the invention include alginate, polylactic acid, polyglycolic acid, PLGA, gelatin, collagen, agarose, poly(lysine), poly-hydroxybutyrate, poly-epsilon-caprolactone, polyphosphazines, poly(vinyl alcohol), poly(alkylene oxide), poly(ethylene oxide), poly(allylamine), poly(acrylate), poly(4-aminomethylstyrene), pluronic polyol, polyoxamer, poly (uronic acid), poly(anhydride) or poly(vinylpyrrolidone). For example, a preferred polymer is alginate.

Alginates are versatile polysaccharide based polymers that may be formulated for specific applications by controlling the molecular weight, rate of degradation and method of scaffold formation. Coupling reactions can be used to covalently attach bioactive epitopes, such as the cell adhesion sequence RGD to the polymer backbone. Alginate polymers are formed into a variety of scaffold types. Injectable hydrogels can be formed from low MW alginate solutions upon addition of a cross-linking agents, such as calcium ions, while macroporous scaffolds are formed by lyophilization of high MW alginate discs. Differences in hydrogel formulation control the kinetics of their degradation. Release rates of morphogens or other bioactive substances from alginate hydrogels is controlled by the hydrogel formulation to present morphogens in a spatially and temporally controlled manner. This controlled release not only eliminates systemic side effects and the need for multiple injections, but can be used to create a microenvironment that activates host cells at the implant site and transplanted cells seeded onto a hydrogel.

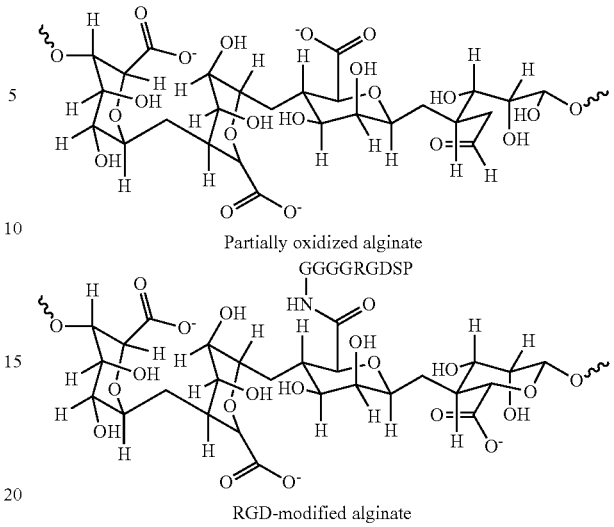

Partially oxidized alginate

RGD-modified alginate

"GGGGRGDSP" disclosed as SEQ ID NO: 12.

The hydrogels are fabricated from a variety of synthetic polymers and naturally-occurring polymers such as, but not limited to, collagen, fibrin, hyaluronic acid, agarose, and laminin-rich gels. One preferred material for the hydrogel is alginate or modified alginate material. Alginate molecules are comprised of (1-4)-linked β-D-mannuronic acid (M units) and α L-guluronic acid (G units) monomers, which can vary in proportion and sequential distribution along the polymer chain. Alginate polysaccharides are polyelectrolyte systems which have a strong affinity for divalent cations (e.g., $Ca^{+2}$, $Mg^{+2}$, $Ba^{+2}$) and form stable hydrogels when exposed to these molecules. See Martinsen A., et al., Biotech. & Bioeng., 33 (1989) 79-89). For example, calcium cross-linked alginate hydrogels are useful for dental applications, wound dressings chondrocyte transplantation and as a matrix for other cell types.

An exemplary hydrogel utilizes an alginate or other polysaccharide of a relatively low molecular weight, preferably of size which, after dissolution, is at the renal threshold for clearance by humans, e.g., the alginate or polysaccharide is reduced to a molecular weight of 80 kDa or less, e.g., 75, 70, 65, 60, 55, 50, 45, 40, 35, 30, 25, 20, 15, 10, 5, 4, 3, 2, 1, 0.5, 0.4, 0.3, 0.2 or 0.1 kDa or less. Preferably, the molecular weight is between about 1 to about 60 kDa, particularly preferably 1 to 50 Kda. Moreover, hydrogels with the relatively low molecular weight of the alginate chain are characterized by the increased chain mobility within the gel mesh and thus a faster relaxation timescale. See Alsberg E et al., (2001) *Journal of Dental Research* 80(11):2025-2029 and Chaudhuri O, et al. (2015) *Nat Commun* 6.

In certain examples, the polymer chain, e.g., the alginate polymer chain, may have a molecular weight of less than 250 kDa, e.g., 249 kDa or less (e.g., 249, 240, 220, 200, 175, 150, 125, 100, 80, 60, 40, 35, 30, 25, 20, 15 kDa, or less).

In some embodiments, the hydrogel is characterized by a stress relaxation rate ($\tau_{1/2}$) of 1000 seconds or less, e.g., 1000, 900, 800, 700, 600, 500, 400, 300, 200, 100, 80, 60, 40, 20, 10, 9, 8, 7, 6, 5, 4, 3, 2, 1 s, or less; or 16, 14, 12, 10, 8, 6, 4, 2, or min or less). In one example, the hydrogel is characterized by a stress relaxation rate ($\tau_{1/2}$) of about 1 min.

Useful polysaccharides other than alginates include agarose and microbial polysaccharides such as those listed in the table below.

| Polysaccharide Scaffold Compositions | |
|---|---|
| Polymers[a] | Structure |
| Fungal | |
| Pullulan (N) | 1,4-;1,6-α-D-Glucan |
| Scleroglucan (N) | 1,3;1,6-α-D-Glucan |
| Chitin (N) | 1,4-β-D-Acetyl Glucosamine |
| Chitosan (C) | 1,4-β.-D-N-Glucosamine |
| Elsinan (N) | 1,4-;1,3-α-D-Glucan |
| Bacterial | |
| Xanthan gum (A) | 1,4-β.-D-Glucan with D-mannose; D-glucuronic Acid as side groups |
| Curdlan (N) | 1,3-β.-D-Glucan (with branching) |
| Dextran (N) | 1,6-α-D-Glucan with some 1,2;1,3-; 1,4-α-linkages |
| Gellan (A) | 1,4-β.-D-Glucan with rhamose, D-glucuronic acid |
| Levan (N) | 2,6-β-D-Fructan with some β-2,1-branching |
| Emulsan (A) | Lipoheteropolysaccharide |
| Cellulose (N) | 1,4-β-D-Glucan |

[a]N-neutral, A = anionic and C = cationic.

A hydrogel of the invention comprises a plurality of alginate polymer chains and a plurality of spacer molecules. A "spacer", or a "spacer molecule", as defined herein, includes a molecule, e.g., a linear molecule, that acts to physically separate the chains of a polymer, such as an alginate polymer. The spacer molecule that comprises a first end and a second end. One of the ends of the spacer molecule may comprise a functional group that allows attachment, e.g., attachment via a covalent bond, of one end of the spacer molecule to the polymer chain. The spacer molecule does not cross-link polymer chains, i.e., it does not attach to two different polymer chains via its two ends. In a specific embodiment, the spacer molecule may be polyethylene glycol (PEG), for example, a PEG molecule that comprises a functional group at one of its ends. Exemplary functional groups are known in the art and include, but are not limited to amine, carboxylic acid, carbodiimide, N-Hydroxysuccinimide, hydroxyl group, thiol group, maleimide group, azide, alkyne, alkene groups, etc. In other examples, a spacer molecule, e.g., PEG, may be attached to an alginate polymer chain using tetrazine-norbornene chemistry. See Desai et al., *Biomaterials* 60(2015):30-37.

In some cases, the PEG molecule may have a molecular weight of less than 50 kDa, e.g., 49 kDa or less (e.g., 49, 40, 35, 30, 25, 20, 15, 10, 5 kDa, or less), e.g., 5 kDa.

In other examples, spacer molecules include but are not limited to a polymer such as collagen, alginate, poly(glycolide) (PGA), poly(L-lactide) (PLA), poly(lactide-co-glycolide) (PLGA), poly lactic-coglycolic acid, silk, polylactic acid, polyglycolic acid, alginate derivatives, gelatin, agarose, natural and synthetic polysaccharides, polyamino acids such as polypeptides particularly poly(lysine), polyesters such as polyhydroxybutyrate and poly-epsilon.-caprolactone, polyanhydrides; polyphosphazines, poly(vinyl alcohols), poly(alkylene oxides) particularly poly(ethylene oxides), poly(allylamines)(PAM), poly(acrylates), modified styrene polymers such as poly(4-aminomethylstyrene), pluronic polyols, polyoxamers, poly(uronic acids), poly(vinylpyrrolidone) and copolymers of the above, including graft copolymers.

For example, the spacer molecules act as plasticizers, which are materials that impart flexibility, workability or stretchability to the polymers (e.g., alginate) in the hydrogel. The spacer molecules provide steric hindrance between main polymer chains (e.g., alginate chains) in the hydrogel. In some examples, the spacer molecules are not covalently coupled to the polymer (e.g., alginate) or to each other, e.g., the polymer and spacer are in a mixture but not chemically attached to one another. Alternatively, the spacer molecules are covalently coupled to the polymer, e.g., alginate. In some cases, the length of the spacer molecule ranges from about 80 Angstroms to about 1500 Angstroms, e.g., about 100 Angstroms to about 1000 Angstroms, e.g., about 250 Angstroms to about 750 Angstroms, e.g., about 500 Angstroms.

For example, the plurality of alginate polymer chains and the plurality of spacer molecules are present in the hydrogel at a ratio of between about 1:1 and about 10:1 spacer molecule:alginate polymer chain. For example, the ratio may be between about 1.5 to about 2 (e.g., about 1.5, 1.8, or 2), i.e., a PEG engraftment of 1.5-2 (e.g., 1.5, 1.8, or 2) PEG per polymer backbone. In some cases, the polymer comprises alginate. For example, the hydrogel comprises 1.5-2 (e.g., 1.5, 1.8, or 2) PEG molecules per alginate chain.

In some embodiments, the ratio of the spacer molecules to polymers (e.g., alginate) is at least 1:1 (e.g., at least 2:1, 3:1, 4:1, 5:1, 6:1, 7:1, 8:1, 9:1, 10:1, or greater). In some cases, the combination of the ratio and the molecular weight of the polymer and/or spacer is specifically designed to tune or alter the rate of stress relaxation of the hydrogel. For example, higher ratios of spacer to polymer (e.g., 2:1 or higher), or lower molecular weight polymers (e.g., 70 kDa or lower, e.g., around 35 kDa) lead to faster stress relaxation. In some cases, a faster rate of stress relaxation (e.g., $\tau_{1/2}$ of 300 seconds or less) can be achieved by using a higher ratio of spacer to polymer (e.g., 2:1 or higher) along with higher molecular weight polymers (e.g., greater than 35 kDa). In other cases, a faster rate of stress relaxation (e.g., $\tau_{1/2}$ of 300 seconds or less) can be achieved by using lower molecular weight polymers (e.g., 70 kDa or lower, e.g., around 35 kDa) combined with any ratio of spacer to polymer.

In the hydrogels of the invention, the plurality of polymer chains, e.g., alginate polymer chains, are ionically cross-linked to each other. Without wishing to be bound by a specific theory, it is believed that hydrogels comprising ionic cross-links are viscoelastic and are capable of stress relaxation behavior because ionic cross-links, being reversible, can un-bind and re-bind when stresses are applient to the hydrogel. U.S. Pat. No. 6,642,363, the entire contents of which are incorporated herein by reference, discloses methods for making and using polymers containing polysaccharides such as alginates or modified alginates that are particularly useful for cell transplantation and tissue engineering applications. Specifically, the hydrogels of the invention may be prepared by combining the plurality of alginate polymer chains in an aqueous solution with ionic cross-linking agents, such as divalent or trivalent cations. Exemplary divalent cations include $Ca^{2+}$, $Mg^{2+}$, $Sr^{2+}$, $Ba^{2+}$, and $Be^{2+}$. Exemplary trivalent cations include $Al^{3+}$ and $Fe^{3+}$. In a specific example, the divalent cation is $Ca^{2+}$. For example, the plurality of alginate polymer chains may be crosslinked by combining them with $Ca^{2+}$ at a concentration of about 2 mM to about 60 mM.

In some examples, the alginate polymer chains of the invention comprise high guluronate content. Alginate polymer chains with high guluronate content possess better ability to form a hydrogel because they may contain regions of guluronate monomers, or G-blocks, which can be linked to each other by a divalent or trivalent cation, e.g., $Ca^{2+}$. In some examples, the divalent cation, $Ca^{2+}$, fits into the guluronate blocks and binds the alginate polymer chains together by forming junction zones, resulting in hydrogel formation.

The hydrogels of the invention may be porous or nonporous. For example, the hydrogels may contain nanopores, micropores, macropores, or a combination thereof. The size of the pores permits cell migration or movement (e.g., fibroblast, MSC, osteogenic cell, bone cell, or cartilage cell migration into and/or egress out of the delivery vehicle) through the pores. For example, the hydrogel comprises pores that are characterized by a diameter of 20-500 µm (e.g., 50-500 µm, or 20-300 µm). In other examples, the hydrogel comprises nanopores, such as pores of 1-500 nm in diameter. In some cases, hydrogels comprising alginate polymer chains comprise pores of 1-10 nm in diameter, and in other cases, hydrogels comprising collagen comprise pores of 100-500 nm in diameter. For example, the hydrogels are nanoporous having a diameter of less than about 10 nm; microporous wherein the diameter of the pores is preferably in the range of about 100 nm-20 µm; or macroporous wherein the diameter of the pores is greater than about 20 µm, more preferably greater than about 100 µm and even more preferably greater than about 400 µm. In one example, the hydrogels are macroporous with aligned pores of about 400-500 µm in diameter. Methods for the preparation of polymer matrices having the desired pore sizes and pore alignments are described, e.g., in U.S. Pat. No. 6,511,650 and US Publication No. 2013/0202707, the entire contents of each of which are incorporated herein by reference.

The consistency of a hydrogel varies from a soft/pliable (e.g., a gel) to glassy, rubbery, brittle, tough, elastic, stiff. The structures contain pores, which are nanoporous, microporous, or macroporous, and the pattern of the pores is optionally homogeneous, heterogenous, aligned, repeating, or random.

The hydrogels of the invention enhance the viability of passenger cells (e.g., mammalian cells, such as fibroblasts or MSCs) and induce their outward migration to populate injured or defective bodily tissues enhance the success of tissue regeneration, e.g., the regeneration of bony tissue, cartilage tissue, neural tissue, muscle tissue or other tissues, as well as angiogenesis. Such a hydrogel that controls cell function and/or behavior, e.g., locomotion, optionally further contains a bioactive composition. The bioactive composition is incorporated into or coated onto the hydrogel. The hydrogel formulation and/or bioactive composition temporally and spatially (directionally) controls egress of a resident cell (e.g., fibroblast or MSC) or progeny thereof. At the end of a treatment period, the hydrogel has release a substantial number of the passenger cells that were originally used to seed the hydrogel, e.g., there is a net efflux of passenger cells. For example, the hydrogel releases 10% or more (e.g., 10%, 20%, 30%, 40%, 50%, 60%, 70%, 80%, 90%, 100%, 200%, 300%, 400%, or more) of the seeded passenger cells by the end of a treatment period compared to at the commencement of treatment. In another example, the hydrogel contains 50% or less (e.g., 50%, 40%, 30%, 25%, 20%, 15%, 10%, 5%, 2.5%, 1%, or less) of the seeded passenger cells at the end of a treatment period compared to at the commencement of treatment. In some cases, a greater number of cells can be released than originally loaded if the cells proliferate after being placed in contact with the hydrogel.

In some cases, the hydrogels mediate modification and release of host cells from the material in vivo, thereby improving the function of cells that have resided in the hydrogel. For example, the hydrogel temporally and spatially (directionally) controls fibroblast or MSC migration. For example, the hydrogel mediates release of fibroblasts or MSC from the material in vivo.

Depending on the application for which the hydrogel is designed, the hydrogel regulates egress through the physical or chemical characteristics of the composition itself. For example, the hydrogel is differentially permeable, allowing cell egress only in certain physical areas of the hydrogel. The permeability of the hydrogel is regulated, for example, by selecting or engineering a material for greater or smaller pore size, density, polymer cross-linking, stiffness, toughness, ductility, or viscoelascticity. The hydrogel contains physical channels or paths through which cells can move more easily towards a targeted area of egress of the hydrogel or of a compartment within the hydrogel. The hydrogel is optionally organized into compartments or layers, each with a different permeability, so that the time required for a cell to move through the hydrogel is precisely and predictably controlled. Migration is also regulated by the degradation, de- or re-hydration, oxygenation, chemical or pH alteration, or ongoing self-assembly of the hydrogel. These processes are driven by diffusion or cell-secretion of enzymes or other reactive chemicals.

Alternatively or in addition, egress is regulated by a bioactive composition. By varying the concentration of growth factors, homing/migration factors, morphogens, differentiation factors, oligonucleotides, hormones, neurotransmitters, neurotransmitter or growth factor receptors, interferons, interleukins, chemokines, cytokines, colony stimulating factors, chemotactic factors, extracellular matrix components, adhesion molecules and other bioactive compounds in different areas of the hydrogel. The hydrogel controls and directs the migration of cells through its structure. Chemical affinities are used to channel cells towards a specific area of egress. For example, adhesion molecules are used to attract or retard the migration of cells. By varying the density and mixture of those bioactive substances, the device controls the timing of the migration and egress. The density and mixture of these bioactive substances is controlled by initial doping levels or concentration gradient of the substance, by embedding the bioactive substances in hydrogel material with a known leaching rate, by release as the hydrogel material degrades, by diffusion from an area of concentration, by interaction of precursor chemicals diffusing into an area, or by production/excretion of compositions by resident support cells. The physical or chemical structure of the hydrogel also regulates the diffusion of bioactive agents through the device.

Accordingly, the hydrogels of the invention may include one or more compounds that regulate cell function and/or behavior. For example, the hydrogels of the invention may also contain cell adhesion ligands (e.g., RGD-containing peptides) and growth factors (e.g., FGF and HGF). The bioactive substances may be covalently linked to the hydrogel or non-covalently associated with the hydrogel. For example, the bioactive composition may be an ECM component that is chemically crosslinked to the polymer chain that is used to make hydrogel.

Regardless of the tissue of origin, ECM components generally include three general classes of macromolecules: collagens, proteoglycans/glycosaminoglycans (PG/GAG), and glycoproteins, e.g., fibronectin (FN), laminin, and thrombospondin. ECM components associate with molecules on the cell surface and mediate adhesion and/or motility. Preferably, the ECM component associated with the scaffold composition is a proteoglycan attachment peptide or cyclic peptide containing the amino acid sequence arginine-glycine-aspartic acid (RGD).

In some examples, the ECM component, such as an RGD peptide, may be cross-linked to the polymer chain, e.g., alginate polymer chain. In further embodiments, the concentration of a cell adhesive peptide, such as RGD, in the crosslinking reaction is greater than 5 µM, e.g., at least 5.1, 10, 15, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 300, 350, 400, 450, 500, 550, 600, 650, 700, 750, 800, 850, 900, 1000, 1200, 1300, 1400, 1500, 1750 µM, or greater. For example, the concentration of the cell adhesive peptide is 5.1 µM-1500 µM. In an embodiment, the concentration of the cell adhesive peptide is about 1500 µM.

In some embodiments, the weight ratio of RGD to alginate is greater than 1:500,000 RGD:alginate, e.g., 1:500 to 1:20 RGD:alginate.

In some examples, hydrogels of the invention may comprise proteoglycan attachment peptides that are selected from the group consisting of G$_4$RGDSP (SEQ ID NO: 12), XBBXBX (SEQ ID NO: 13), PRRARV (SEQ ID NO: 14), YEKPGSPPREVVPRPRPGV (SEQ ID NO: 15), RPSLAKKQRFRHRNRKGYRSQRGHSRGR (SEQ ID NO: 16), and RIQNLLKITNLRIKFVK (SEQ ID NO: 17), and cell attachment peptides are selected from the group consisting of RGD, RGDS (SEQ ID NO: 1), LDV, REDV (SEQ ID NO: 2), RGDV (SEQ ID NO: 3), LRGDN (SEQ ID NO: 4), IKVAV (SEQ ID NO: 5), YIGSR (SEQ ID NO: 6), PDSGR (SEQ ID NO: 7), RNIAEIIKDA (SEQ ID NO: 8), RGDT (SEQ ID NO: 9), DGEA (SEQ ID NO: 10), and VTXG (SEQ ID NO: 11).

Components of the ECM, e.g., FN, laminin, and collagen, interact with the cell surface via the integrin family of receptors, a group of divalent cation-dependent cell surface glycoproteins that mediate cellular recognition and adhesion to components of the ECM and to other cells. Ligands recognized by integrins typically contain an RGD amino acid sequence that is expressed in many ECM proteins. Exemplary molecules that mediate cell adhesion and/or movement include FN, laminin, collagen, thrombospondin 1, vitronectin, elastin, tenascin, aggrecan, agrin, bone sialoprotein, cartilage matrix protein, fibrinogen, fibrin, fibulin, mucins, entactin, osteopontin, plasminogen, restrictin, serglycin, SPARC/osteonectin, versican, von Willebrand Factor, polysaccharide heparin sulfate, cell adhesion molecules including connexins, selectinsinclude collagen, RGD (Arg-Gly-Asp) and YIGSR (Tyr-Ile-Gly-Ser-Arg) (SEQ ID NO: 6) peptides, glycosaminoglycans (GAGs), hyaluronic acid (HA), integrins, selectins, cadherins and members of the immunoglobulin superfamily. Carbohydrate ligands of the ECM include the polysaccharides hyaluronic acid, and chondroitin-6-sulfate.

Signal transduction events that participate in the process of cell motility are initiated in response to cell growth and/or cell differentiation factors. Thus, the device optionally contains a second bioactive composition that is a growth factor, morphogen, differentiation factor, or chemoattractant. For example, the device includes vascular endothelial growth factor (VEGF), hepatocyte growth factor (HGF), or fibroblast growth factor 2 (FGF2) or a combination thereof. Other factors include hormones, neurotransmitters, neurotransmitter or growth factor receptors, interferons, interleukins, chemokines, MMP-sensitive substrate, cytokines, colony stimulating factors. Growth factors used to promote angiogenesis, bone regeneration, wound healing, and other aspects of tissue regeneration are listed herein and are used alone or in combination to induce colonization or regeneration of bodily tissues by cells that have migrated out of an implanted device.

In some examples, the hydrogel comprises a bioactive composition, where the bioactive composition is an agent that promotes bone regeneration, e.g., transforming growth factor-β (TGF-β), bone morphogenetic protein (BMP), insulin-like growth factor (IGF-1), fibroblast growth factor-2 (FGF-2), or platelet-derived growth factor (PDGF), e.g., as shown in the table below.

| Growth factors used for bone regeneration | | |
|---|---|---|
| Growth factor | Abbreviation | Relevant activities |
| Transforming growth factor-β | TGF-β | Proliferation and differentiation of bone-forming cells |
| Bone morphogenetic protein | BMP | Differentiation of bone-forming cells |
| Insulin-like growth factor | IGF-1 | Stimulates proliferation of osteoblasts and the synthesis of bone matrix |
| Fibroblast growth factor-2 | FGF-2 | Proliferation of osteoblasts |
| Platelet-derived growth factor | PDGF | Proliferation of osteoblasts |

Cells (e.g., fibroblasts, MSCs, or differentiated MSCs (e.g., into osteogenic cells)) contained in the hydrogels described herein promote regeneration of a tissue or organ (e.g., bone) immediately adjacent to the hydrogel, or at some distant site.

Methods of the Invention

The present invention further provides methods of enhancing proliferation or differentiation of a cell. The methods include contacting the cell with a fast relaxing hydrogel as defined herein, i.e., a hydrogel characterized by a fast stress relaxation rate ($\tau_{1/2}$). The cell may be an isolated cell or may be a cell inside a body of a subject in need of tissue regeneration and/or bone formation. For example, such contacting step enhances the proliferation, spreading, and/or differentiation of the cell. The proliferation (e.g., growth rate) of a cell is determined by standard methods available in the art. In some embodiments, the hydrogel increases the growth rate of a cell or population of cells by at least 1.5-fold, e.g., at least 1.5, 2, 3, 4, 5, 6, 7, 8, 9, 10-fold, or more, compared to the growth rate of the cell or population of cells prior to contacting the hydrogel. Alternatively, the hydrogel increases the growth rate of a cell or population of cells by at least 1.5-fold, e.g., at least 1.5, 2, 3, 4, 5, 6, 7, 8, 9, 10-fold, or more, compared to the average growth rate of the type of cell in a subject prior to administration of the hydrogel. Differentiation of a cell down a certain lineage, e.g., adipogenic or osteogenic, can be determined by standard methods available in the art, such as the measurement of expression markers characteristic of differentiated cells. Exemplary methods/differentiation methods are described herein greater detail below.

The invention also provides a method of enhancing proliferation and/or differentiation of a cell, comprising contacting the cell with a hydrogel described herein. In some cases, the cell comprises a fibroblast, MSCs, osteogenic cell, bone cell, or cartilage cell. In other examples, the cell comprises a neuroprogenitor cell, adipogenic cell, or muscle precursor cell. In one example, the cell comprises a stem cells, such as an MSC. For example, the hydrogel enhances osteogenic differentiation of the MSC. Osteogenic differentiation is determined, e.g., by standard methods commonly known in the art, e.g., alkaline phosphate staining, Von Kossa (mineralization) assays, collagen-I staining. For example, MSCs contacted with the hydrogel differentiate into active osteoblasts. In some examples, the MSCs contacted with the hydrogel undergo osteogenic differentiation and form an interconnected mineralized matrix, e.g., containing collagen-1.

In some examples, the MSC migrates out of the hydrogel into a surrounding tissue. In other examples, the MSC differentiates in/on the hydrogel (e.g., into an osteogenic cell, bone cell, or cartilage cell), and subsequently migrates out of/away from the hydrogel into a surrounding tissue, e.g. a bone or cartilage.

The invention also provides methods of regenerating a tissue in a subject in need thereof. The methods include administering to the subject a fast relaxing hydrogel as defined herein, i.e., a hydrogel characterized by a fast stress relaxation rate ($\tau_{1/2}$). The tissue may be a bone tissue, muscle tissue, cartilage tissue, or vascular tissue. A subject may be a mammal, such as a human, monkey, horse, cow, sheep, dog, cat, or rabbit. The subject may suffer from a bone or cartilage defect, such as a damaged bone/cartilage, e.g., caused by a wound, surgery, injury, or a disease.

In some cases, the subject suffers or has suffered from a bone/cartilage disorder or a disease associated with bone damage, such as osteoporosis, osteoarthritis, rheumatoid arthritis, osteogenesis imperfecta, Paget's disease, cancer (e.g., lung cancer, breast cancer, prostate cancer, leukemia, osteosarcoma, Ewing sarcoma, malignant fibrous histiocytoma, or chondrosarcoma), metastatic cancer, rickets, osteomalacia, acromegaly, Perthes' disease, fibrous dysplasia, osteomyelitis, an infection, chondrodystrophy, rupture/detachment of a joint (e.g., knee cartilage), achondroplasia, costochondritis, spinal disc herniation, or polychondritis (e.g., relapsing polychrondritis).

In other cases, the subject suffers or has suffered from a wound, e.g., a hematoma, a blunt force trauma, a cut, scrape, gunshot wound, battlefield wound, stabbing wound, a bone fracture, a chronic wound (e.g., a diabetic wound), an ulcer, a bruise, a concussion, a contusion, a laceration, an abration, or a surgical wound.

In other cases, the subject suffers or has suffered from a surgery, e.g., an amputation, heart surgery, breast surgery, laparoscopic surgery, colon or rectal surgery, endocrine surgery, eye surgery, otolaryngology surgery, neurosurgery, plastic/reconstructive surgery (e.g., rotationplasty), vascular surgery, endovascular surgery, a surgery to remove a tumor, arthroplasty, bone surgery (e.g., to fix a fracture, e.g., by open reduction and/or internal fixation), insertion/replacement of a bone graft, surgery to remove a bone cancer (e.g., limb-salvage surgery, curettage, cryosurgery, optionally with the use of bone cement), or implantation of a medical device. Exemplary medical devices include stents, catheters, and drug delivery depots.

In some examples, the subject suffers from a fracture, e.g., bone fracture. For example, the microenvironment around a bone fracture contains coagulated bone marrow, blood, and/or cells. For example, the stress relaxation timescale of an early fractured callus (e.g., after 7 days) is about 1 min. See, e.g., FIG. 1A and McDonald et al. J. Orthopaedic Res. 2009. Fracture healing occurs in three phases. In the first phase after a fracture occurs, or reactive phase, blood cells are detected in the tissues adjacent to the injury site. To stop further bleeding, e.g., within a few hours after fracture, a blood clot (hematoma) is formed by the extravascular blood cells. At the site of the blood clot, fibroblasts proliferate and form a loose aggregate of cells interspersed among small blood vessels. This loose aggregate of cells is called granulation tissue. In the second phase of fracture healing (reparative phase), which occurs days after the fracture, periosteal cells located in close proximity to the fracture gap proliferate and develop into chondroblasts that form hyaline cartilage. The fibroblasts in the granulation tissue also develop into chondroblasts and form hyaline cartilage. Periosteal cells located farther away from the fracture gap develop into osteoblasts that form woven bone. The new tissue grow to form in a mass of heterogeneous new tissue called a fracture callus. The fracture gap is eventually filled in by hyaline cartilage and woven bone. Next, the hyaline cartilage and woven bone are replaced with lamellar bone in a process called endochondral ossification and bony substitution. In these processes, collagen matrix of the cartilage/woven bone becomes mineralized, and the mineralized matrix is penetrated by channels containing osteoblasts and microvessels. The osteoblasts form new lamellar bone in the form of trabecular bone. During the reparative phase, eventually all of the woven bone and cartilage of the fracture callus becomes replaced by trabecular bone. The third phase of fracture healing is remodeling, in which trabecular bone is replaced with compact bone. The trabecular bone is resorbed by osteoclasts, and osteoblasts deposit compact bone at the resorption pit. Over time, in the remodeling phase, the fracture callus is reshaped into a new shape similar to the bone's original strength and shape. The amount of time for completion of the remodeling phase varies depending on the health and age of the subject, and generally takes several years.

In some cases, the fast relaxing hydrogels described herein accelerate the fracture healing process, e.g., reduce the amount of time for one or more of the three phases of fracture healing to complete in a subject, as compared to the average time required for the phase to complete in a normal healthy subject of a similar age group that has not been administered a hydrogel described herein or who has been administered a hydrogel characterized by a slow stress relaxation rate.

In some embodiments, the methods are useful for cartilage replacement, regeneration or repair; bone regeneration, replacement or repair; or joint regeneration, replacement or repair. For example, a bone comprises a tooth, a scapula, a sternum, a clavicle, a humerous, ulna, radius, carpus, metacarpus, a phalange, a femur, patella, tibia, fibula, vertebrae, cuboid bone, navicular bone, cuneiform bone, metatarsal, talus, or calcaneus. For example, a joint comprises a rotator cuff, a ball-and-socket shoulder joint, an elbow joint, wrist joint, a condyloid joint in a hand, hip joint, neck, knee, or ankle. For example, cartilage comprises elastic cartilage, hyaline cartilage, or fibrocartilage. For example, the methods/hydrogels described herein are useful for accelerating or mediating the healing of a fracture.

In some examples, the hydrogel is seeded with mammalian cells prior to administration, e.g., the mammalian cells are encapsulated into the hydrogel. For example, the cells are encapsulated during the cross-linking process to form the hydrogel. In other cases, the hydrogel contacts a mammalian cell after administration into a subject. In some cases, the mammalian cell comprises a stem cell, such as a MSC. In some examples, the MSC differentiates down an osteogenic lineage, e.g., into an osteoprogenitors/pre-osteoblasts, or into a bone cell (e.g., osteoblast, osteoclast, osteocyte, or lining cell). In other examples, the MSC differentiates into a chondrocyte. Alternatively or in addition, the mammalian cell comprises a differentiated cell, such as an osteoprogenitor, bone cell, or chondrocyte.

In some cases, an endogenous cell migrates to and/or into an administered hydrogel (e.g., through the pores). For example, a MSC enters the hydrogel, and optionally differentiates and/or proliferates on/in the hydrogel. In some cases, the MSC subsequently leaves the hydrogel as a MSC or differentiated cell (e.g., osteoprogenitor/pre-osteoblast, bone cell, or chrondrocyte).

In some embodiments, the hydrogel is useful as a bone/cartilage replacement, such as a bone/cartilage graft.

In some examples, the hydrogels of the invention enhance bone or cartilage formation at the site of hydrogel administration or at a site away from the site of administration (e.g., within 1 m, e.g., within 10 cm, 8 cm, 6 cm, 4 cm, 2 cm, 1 cm, 10 mm, 9 mm, 8 mm, 7 mm, 6 mm, 5 mm, or less, of a perimeter/border of the hydrogel).

The term "isolated" used in reference to a cell type, e.g., a fibroblast or MSC, means that the cell is substantially free of other cell types or cellular material with which it naturally occurs. For example, a sample of cells of a particular tissue type or phenotype is "substantially pure" when it is at least 60% of the cell population. Preferably, the preparation is at least 75%, more preferably at least 90%, and most preferably at least 99% or 100%, of the cell population. Purity is measured by any appropriate standard method, for example, by fluorescence-activated cell sorting (FACS). Optionally, the hydrogel is seeded with two or more substantially pure populations of cells. The populations are spatially or physically separated, e.g., one population is encapsulated, or the cells are allowed to come into with one another. The hydrogel or structural support not only provides a surface upon which cells are seeded/attached but indirectly affects production/education of cell populations by housing a second (third, or several) cell population(s) with which a first population of cells associates (cell-cell adhesion).

In accordance with the methods of the invention, hydrogels described herein are administered, e.g., implanted, e.g., orally, systemically, sub- or trans-cutaneously, as an arterial stent, surgically, or via injection. In some examples, the hydrogels described herein are administered by routes such as injection (e.g., subcutaneous, intravenous, intracutaneous, percutaneous, or intramuscular) or implantation.

The term, "about", as used herein, refers to a stated value plus or minus another amount; thereby establishing a range of values. In certain preferred embodiments "about" indicates a range relative to a base (or core or reference) value or amount plus or minus up to 15%, 14%, 13%, 12%, 11%, 10%, 9%, 8%, 7%, 6%, 5%, 4%, 3%, 2%, 1%, 0.75%, 0.5%, 0.25% or 0.1%.

The invention also includes a method of making the hydrogels described herein. For example, the method comprises providing a polymer, such as alginate, e.g., a low molecular alginate of less than 250 kDa. The polymer, e.g., alginate, is then mixed with (noncovalently) or coupled (covalently) to a spacer molecule, such as PEG. The polymer, such as alginate, can also be coupled to cell adhesion ligand, such as an RGD-containing peptide, prior or subsequent to the coupling to the spacer molecule, e.g., PEG.

Exemplary hydrogels and methods of making them are described in US 2012/0100182, PCT/US2010/057630, and PCT/US2012/35505, the entire contents of each of which is hereby incorporated by reference. U.S. Pat. No. 6,642,363, incorporated herein by reference, discloses methods for making and using polymers containing polysaccharides such as alginates or modified alginates that are particularly useful for cell transplantation and tissue engineering applications.

Methods of making a hydrogel described herein include using gas foaming, e.g., as described in detail in Harris et al. J. Biomed. Materials Res. Part A. 42.3(1998)396-402 and Sheridan et al. J. Control. Rel. 64(2000)91-102, both incorporated herein by reference. In other embodiments, wires (e.g., a template containing multiple wires) are used as porogens, i.e., to create pores in the scaffold, e.g., to create aligned pores. In other examples, methods for making hydrogels, e.g., encapsulating cells, are also described in PCT/US2012/033208, the entire contents of which are incorporated herein by reference.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and are not intended to be limiting.

The invention is further illustrated in the following non-limiting examples.

Examplification of the Invention

Materials and Methods
  Alginate Preparation.
  Sodium alginate rich in guluronic acid blocks and with a high molecular weight (280 kDa, LF20/40) was purchased from FMC Biopolymer, and was prepared as has been described previously (Rowley, et al., *Biomaterials* 20, 45-53 (1999)). Briefly, high molecular weight alginate was irradiated by a 3 or 8 Mrad Cobalt source to produce lower molecular weight alginates. RGD-alginate was prepared by coupling the oligopeptide GGGGRGDSP (Peptides International) (SEQ ID NO: 12) to the alginate using carbodiimide chemistry at concentrations such that 2, 10, or 20 RGD peptides were coupled to 1 alginate chain on average for high molecular weight alginate (peptide molar concentrations in low molecular weight alginates were kept the same according to high molecular weight alginate for each degree of substitution, respectively). The coupling efficiency using this procedure was previously characterized using $^{125}$I labeled RGD peptides (Rowley, et al., *Biomaterials* 20, 45-53 (1999)). These correspond to densities of 150 µM, 750 µM, and 1500 µM RGD in a 2% wt/vol alginate gel. Alginate was dialyzed against deionized water for 2-3 days (molecular weight cutoff of 3.5 kDa), treated with activated charcoal, sterile filtered, lyophilized, and then reconstituted in serum free DMEM (Life Technologies).

For in vivo studies, sodium alginate (280 kDa, LF20/40) was used as-received for preparing slow-relaxing hydrogel and was irradiated with an 8 mRad cobalt source for preparing fast-relaxing hydrogel. The irradiation of the alginate lowered its molecular weight while maintaining the same G to M block ratio. Alginates were modified with GGGGRGDSP peptides (Peptide 2.0) (SEQ ID NO: 12) at a ratio of 20 peptides per alginate. After modification, alginates were dialyzed against an NaCl gradient, treated with activated charcoal, and sterile-filtered. After lyopholization, all alginate was dissolved in serum-free DMEM (Lonza) at 2.5%.

Hydrogels used in the in vivo studies were cast by mixing the alginate prepolymer solution with $CaSO_4$ slurry rapidly via two syringes and ejecting the mixture between two glass plates, where it gelled over 1.5 hours. Slow-relaxing gels consisted of 2% alginate and 20 mM Ca, while fast relaxing gels consisted of 2% alginate and 42 mM Ca. This difference in calcium concentration has previously been noted to have no effect on mesenchymal stem cell viability and differentiation RR. 8 mm disks were then cut from the gel using a biopsy punch.

Polyethylene glycol (PEG)-alginate was prepared by coupling PEG-amine (5 kDa, Laysan Bio) to the low molecular weight alginate (35 kDa) using carbodiimide chemistry in a similar procedure to the RGD coupling (Rowley et al. Biomaterials 20, 45-53 (1999)). 295 mg of PEG-amine was mixed with 50 mL of 10 mg/mL alginate in 0.1 M MES (2-(N-morpholino)ethanesulfonic acid, Sigma-Aldrich) buffer at pH 6.5. Then 242 mg of EDC (N-(3-Dimethylaminopropyl)-N'-ethylcarbodiimide hydrochloride, Sigma-Aldrich) and 137 mg of Sulfo-NHS (N-hydroxysulfosuccinimide, Thermo Fisher Scientific) were added into the solution. The reaction was carried out for 20 hours under constant stiffing. The product was dialyzed against deionized water for 3 days (molecular weight cutoff of 10 kDa), filtered with activated charcoal, sterile filtered, and lyophilized. The structure of the PEG-alginate was confirmed with nuclear magnetic resonance (NMR) and gel permeation chromatography (GPC). Based on the change of molecular weight of alginate before and after PEG coupling (from 35 kDa to 45 kDa), an average of 2 PEG molecules were coupled to 1 alginate chain. This number was confirmed by $^1$H NMR spectroscopy (FIGS. 10A-C).

Alginate Characterization.

Molecular weights of alginates and PEG-alginate were analyzed with a Malvern Viscotek 270max GPC equipped with a GPCmax solvent and sample delivery module, an Eldex Ch-150 temperature-controlled column holder, a VE 3580 refractive index (RI) detector, viscotek 270 Dual Detector featuring intrinsic viscosity (IV-DP) and right angle light scattering (RALS), and OmniSec software. Samples were dissolved in 0.1 M $NaNO_3$ buffer solution at a concentration of 5 mg/mL, and 200 µL of sample was injected. Polymers separated through a set of two TSK-gel columns (G4000PWXL and G3000PWXL) were analyzed with the triple detector system. Malvern PEO and pullulan standards were used in molecular weight calculation, and weight average molecular weights (Mw) were used.

High-resolution $^1$H NMR spectra were obtained in deuterium oxide ($D_2O$) using a Varian Unity-400 (400 MHz) NMR spectrometer (Varian). $^1$H NMR was used to characterize PEG coupling of alginate and degree of functionalization of PEG-alginate.

Mechanical Characterization.

AFM measurements of the Young's modulus of the alginate gels were performed with an MFP-3D system (Asylum Research) using silicon nitride cantilevers (MLCT, Bruker AFM Probes). The stiffness was calibrated from the thermal fluctuations of the cantilever in air, and cantilevers with a stiffness of ~13 pN/nm were used. The cantilever was moved towards the stage at a rate of 1 µm/s and force indentation curves were interpreted using the Hertzian model for a pyramidal indentor (Bilodeau, G. G. J. Appl. Mech. 59, 519 (1992)). Rheology measurements were made with an AR-G2 stress controlled rheometer (TA Instruments). Alginate gels were deposited directly onto the surface plate of the rheometer immediately after mixing with the crosslinker. A 20 mm plate was immediately brought down, forming a 20 mm disk of gel with an average thickness of ~1.8 mm. The mechanical properties were then measured over time until the storage modulus reached an equilibrium value. The storage modulus at 0.5% strain and at 1 Hz was recorded periodically until the storage modulus reached its equilibrium value (2D studies), or after 45 minutes (3D studies). Then, a strain sweep was performed to confirm this value was within the linear elastic regime, followed by a frequency sweep. No prestress was applied to the gels for these measurements. The initial Young's moduli and stress relaxation properties of alginate gels were measured from compression tests of the gel disks (15 mm in diameter, 2 mm thick, equilibrated in DMEM for 24 hr) using a previously published method (Huebsch, et al., Nat Mater 9, 518-526 (2010); Zhao, et al., J. Appl. Phys. 107, 63509 (2010)). The gel disks were compressed to 15% strain with a deformation rate of 1 mm/min using an Instron 3342 single column apparatus. Within 15% compression, the stress vs. strain relations of the gels are almost linear, and the slope of the stress-strain curves (first 5-10% of strain) gives the initial Young's modulus. Subsequently, the strain was held constant, while the load was recorded as a function of time. Compression and stress relaxation measurements of biological tissues were performed using the same procedure. Sprague Dawley Rats (male, 7 weeks of age, Charles River Lab) were euthanized in compliance with National Institutes of Health and institutional guidelines. Brain, liver, and adipose were collected immediately after euthanization and tested with Instron 3342 single column apparatus. Bone marrow from multiple rat femurs and tibias were collected fresh after euthanization and allowed to coagulate for 1 hr before compression testing. Stress relaxation tests that were noisy were smoothed with a Savitzky-Golay filter in Igor Pro (Wavemetrics) with a 4 s window.

For in vivo studies, hydrogels were fabricated at a thickness of 2 mm and subjected to compression testing. Specifically, gels were compressed at a strain rate of 1 mm/min and the Young's Modulus was calculated as the best-fit slope of the first 5-15% of the resulting stress/strain curve. At 15% strain, the strain was held and the time required for the stress at 15% strain to decay by a factor of two was noted.

Cell Culture.

U2OS and 3T3 fibroblasts (ATCC) were cultured in standard Dulbecco's Modified Eagles Medium (DMEM, Invitrogen) with 10% Fetal Bovine Serum (Invitrogen) and 1% penicillin/streptomycin (Invitrogen). D1 cells, clonally derived mouse bone marrow stromal mesenchymal stem cells, were originally obtained from Balb/c mice (Diduch, et al., J. Bone Joint Surg. Am. 75, 92-105 (1993)). The D1s were maintained at sub-confluency in DMEM containing 10% Fetal Bovine Serum and 1% Pen/Strep. For differentiation experiments, the culture medium was supplemented with 50 µg/mL L-ascorbic acid (Sigma), 10 mM β-glycerophosphate (Sigma), and 0.1 µM dexamethasone (Sigma) (Diduch, et al., J. Bone Joint Surg. Am. 75, 92-105 (1993)). The medium was changed every 3-4 days.

Plating of Cells on Gels.

1 mm thick alginate hydrogels were prepared as previously described (Zhao et al. J. Appl. Phys. 107, 63509 (2010); and Huebsch et al. *Nat Mater* 9, 518-526 (2010)). Following gelation, 15 mm disks were punched out, and these disks were washed thoroughly 4 times over 2 days in serum free media to remove any excess calcium. Disks were held fixed to the bottom of a well-plate by a customized plastic insert (so that they did not float when submerged in media), and cells were plated at a low density of 10,000 cells/cm$^2$, so that cells did not contact other cells on average. Cells were allowed to spread for 20 hours, and then were fixed and stained for analysis. Only isolated cells, without any cell-cell contacts, were analyzed.

Encapsulation of Cells within 3-D Hydrogels.

Cells in flasks were trypsinized using 0.05% trypsin/EDTA (Invitrogen), washed once in serum free DMEM, and resuspended in serum free media at 10× the final concentration. The concentration of the cells was determined using a Coulter counter (Beckman Coulter). Cells were then mixed well with alginate, also reconstituted in serum free DMEM using luerlock syringes (Cole-Parmer) and a female-female luerlock coupler (Value-plastics). The cell-alginate solution was then rapidly mixed with DMEM containing the appropriate concentration of calcium sulfate, and then deposited between two glass plates spaced 1 mm apart. The solutions were allowed to gel for 45 minutes, and then disks of hydrogel were punched out and transferred to well plates where they were immersed in media.

In Vitro hMSC Differentiation.

For the experiments described in Example 9, human mesenchymal stem cells (Rooster Bio) were encapsulated in slow and fast relaxing hydrogels at a final concentration of 15 million cells/mL gel, punched into disks, and placed into 24-well plates. The encapsulated cells were cultured in osteogenic differentiation medium (Stempro, Life Technologies) and cell culture medium was changed every 3-4 days for two weeks. At two weeks, samples were fixed in 4% paraformaldehyde for 45 min on an orbital shaker, exposed to increasing concentrations of OCT in a sucrose solution, and flash frozen for cryosectioning. Gels were sectioned at a thickness of 50 µm before von Kossa Staining. Briefly, sections were incubated in a 1% silver nitrate solution under ultraviolet light for 20 min, rinsed with DI water, and incubated in 5% sodium thiosulfate for 5 min.

Immunohistochemistry.

For immunohistochemical staining, media was first removed from the gels. The gels were then fixed with 4% paraformaldehyde in serum free DMEM at 37° C. for 30-45 minutes. Gels were then washed 3 times in PBS containing calcium (cPBS). Gels from 3D studies were then incubated overnight in 30% sucrose in cPBS at 4° C. The gels were then placed in a mix of 50% of a 30% sucrose in cPBS solution, and 50% OCT (Tissue-Tek) for several hours. Then the media was removed, the gels were embedded in OCT and frozen. The frozen gels were sectioned with a cryostat (Leica CM1950) to a thickness of 30-100 µm, and stained following standard immunohistochemistry protocols. Gels from 2D studies were stained following standard immunohistochemistry protocols directly following washing after fixation. The following antibodies/reagents were used for immunohistochemistry: Rabbit-anti-mouse Collagen I polyclonal antibody (Abcam 34710), YAP antibody (Cell Signaling), Prolong Gold antifade reagent with DAPI (Invitrogen), AF-488 Phalloidin to stain actin (Invitrogen), Goat anti-Rabbit IgG AF 647 (Invitrogen). The Click-IT EdU cell proliferation assay (Invitrogen) was used to identify proliferating cells.

Image Analysis.

For measurements of cell spreading area in 2D, images of phalloidin/DAPI stained cells were taken for the indicated conditions at 20× or 63× with a laser scanning confocal microscope (LSM 710, Zeiss). Only cells that did not exhibit any cell-cell contacts were considered in the analysis. Images of all single cells were then thresholded manually based on the actin stain, and the area of the thresholded cell body was determined using a custom macro in ImageJ (NIH).

For measurements of YAP nuclear localization in both 2D and 3D, images of DAPI/phalloidin/YAP antibody stained cells were taken with an NA=1.40 63× PlanApo oil immersion objective with a laser scanning confocal microscope. Images were thresholded on each color channel to determine the nuclear area and cell/cytoskeleton area outside of the nucleus. The YAP nuclear localization ratio was then determined as the summed intensity of the YAP signal within the nucleus normalized by the nuclear area divided by the summed intensity of the YAP signal outside of the nucleus normalized by the non-nuclear cytoskeleton area.

Spreading of 3T3 cells in 3D gels was quantified using Imaris software (Bitplane). Z-stack images of DAPI/phalloidin stained cells were taken with a laser scanning confocal microscope. The stacks were analyzed using Imaris with embedded cell body algorithm. The DAPI channel was used for nuclei detection and the phalloidin channel was used for cell body detection. Statistics of the cells were generated by the algorithm, and the longest dimension of the object-oriented bounding box of each cell was determined as an indication of cell spreading.

Analysis of MSC Differentiation.

Oil Red O staining was performed on 100 µm frozen sections to probe for neutral lipids. Slides were equilibrated in 60% isopropanol and stained in 1.8 mg/ml Oil Red O in 60% isopropanol for 30 minutes. Frozen sections were probed for alkaline phosphatase by Fast Blue staining. The slides were equilibrated in alkaline buffer (100 mM Tris-HCl, 100 mM NaCl, 0.1% TWEEN-20, 50 mM $MgCl_2$, pH 8.2) for 15 minutes and stained in 500 µg/ml naphthol AS-MX phosphate (Sigma) and 500 µg/ml Fast Blue BB Salt Hemi (ZnCl) salt (Sigma) in alkaline buffer for 60 minutes. The sections were then washed in alkaline buffer and neutralized in PBS. Von Kossa staining was performed on 30 µm frozen section to probe for mineralized matrix. Samples were equilibrated in distilled water and exposed to 3% silver nitrate solution under UV light for 1 min. After several dips in distilled water, a 2.5% sodium thiosulphate solution in 50 mM HEPES with 25 mM $CaCl_2$ was added for 2 minutes, followed by washes in distilled water.

For the experiments described in Example 9, a Tescan Vega environmental scanning electron microscope (SEM) with a Bruker XFlash 5030 energy dispersive X-ray spectrometer (EDS) was used for elemental characterization of in vitro hMSC differentiation. Gels were prepared in frozen blocks as they were for von Kossa staining and then were sectioned at a thickness of 70 um onto a p-type silicon wafer. Excess phosphate and calcium was removed by washing in water, followed by drying under vacuum overnight. Elemental analysis and mapping of phosphorus were performed at an accelerator voltage of 20 keV and a pressure of 12 Pa.

To quantify ALP enzyme activity, cells were retrieved from the gels after 7 days of culture. Cells were collected by incubation in trypsin for 10 minutes followed by a PBS wash, and soaking gels in 50 mM EDTA in PBS for 10 minutes at room temperature. The cells were counted using a Z2 Coulter Counter and lysed for 30 min in lysis buffer (50 mM Tris-HCl, 0.1% Triton X-100) at 4° C. 10 µL of each lysate was added to 100 µL 4-Methylbelliferyl phosphate (4-MUP) substrate (Sigma) and incubated for 25 minutes at 37° C. Bovine ALP (Sigma) was used to create a standard curve. After incubation, fluorescence was read by a fluorescent plate reader (BioTek) and measured ALP activity was normalized to cell counts.

Color micrographs of Oil Red 0, Fast Blue, and von Kossa staining were acquired using a Nikon E800 upright microscope and an Olympus DP-70 color camera.

Structural and compositional analyses of the alginate gels were performed with a Tescan Vega environmental scanning electron microscope (SEM) equipped with a Bruker XFlash 5030 energy dispersive X-ray spectrometer (EDS). Frozen sections of alginate gels with a thickness of 100 µm were attached to a silicon wafer with conductive carbon tape. The gel sections were washed in DI water for 4 times, 5 minutes each time to remove any soluble $Ca^{2+}$ and phosphate, and dried under vacuum overnight before SEM-EDS. Elemental mapping and compositional analysis of phosphorus for each sample was performed under identical conditions at an accelerator voltage of 20 keV and 12 Pa of pressure. See FIGS. 9A-D.

Hydrogel Implantation in Rat Calvarial Defect Model.

All animal experiments were performed in compliance with National Institutes of Health guidelines and were approved by the Institutional Animal Care and Use Committee at Harvard University. The rat calvarial defect surgery was performed on four-week old RNU Rats (Charles River Laboratories) as described previously. Briefly, animals were anesthetized, and their heads were shaved. An incision was made longitudinally along the head and the exposed periosteum was scraped to the side. 8 mm defects were drilled and removed from the rat calvarium, and 8 mm hydrogels were implanted into the resulting void. Fascia and skin layers were sutured separately in order to keep the gels stationary. After three months, animals were euthanized with $CO_2$ and decapitated. The calvarium was removed using bone shears and placed in 10% formalin for 24 hours. Samples were then stored at 4° C. in PBS until further use.

X-Ray Micro-Computed Tomography.

Rat calvaria were wrapped in paraffin to prevent dehydration and scanned in an X-tek HMXST225 micro-computed tomography system at the Harvard University Center for Nanoscale Systems. Samples were reconstructed using CT Pro and rendered using VG Studio Max software. For new bone quantification in VG Studio Max, an 8 mm diameter cylinder volume of interest was centered over the defect site, with a height equivalent to the thickness of the adjacent bone. The volume within the cylinder encapsulated in an isosurface rendering was calculated and the percent of defect filled was treated as the fraction of the cylinder, thus representing the original defect volume, filled by the new bone.

Histology.

After tomography, samples were sent to the Dana Farber Cancer Rodent Histopathology Core for paraffin embedding and sectioning, as well as Hematoxylin and Eosin, Van Gieson, Masson's Trichrome, and Alcian Blue staining. Imaging was performed on a Nikon histology microscope. Immunofluorescence staining was performed using anti-human mitochondria primary antibodies (Abcam). Paraffin was removed with two 5 minute xylene washes, and slides were rehydrated in successively lower concentrations of ethanol in DI water. For human mitochondria antigen retrieval, samples were incubated in sodium citrate buffer, pH 6.0, at 95° C. for twenty minutes. Slides were blocked in 10% normal goat serum, 1% bovine serum albumin, and 0.05% Tween-20 in PBS for 1 hour at room temperature, and incubated in primary antibody solution using the manufacturer's recommended concentrations overnight at 4° C. Slides were then incubated in goat anti-mouse Alexa 555 secondary antibodies (Abcam) for 1 hour at room temperature and counterstained with Hoescht. Imaging was performed on a Carl Zeiss LSM 710 upright confocal microscope.

Tissue Mimicking Scaffolds/Hydrogels for Bone Regeneration

Described herein is a method of making polymer hydrogels that promote bone regeneration. For example, cobalt source irradiated sodium alginates and irradiated alginates that grafted with polyethylene glycol form hydrogels when crosslinked with divalent cations. These hydrogels are viscoelastic and exhibit fast stress relaxation behavior when strain is applied. In some cases, the stress relaxation behavior is adjusted to mimic the mechanical properties in natural biological tissues. The proliferation and differentiation of MSC that were seeded in the hydrogels were significantly influenced by the stress relaxation property of the hydrogels. The ability of MSCs to differentiate into active osteoblasts and form a highly mineralized collagen-rich matrix (indicators of bone) was significantly augmented in rapidly relaxing gels that exhibit stress relaxation behavior that is similar to biological tissues such as fracture callus and coagulated marrow.

Accordingly, the hydrogels are useful for tissue engineering, e.g., bone regeneration. For example, the invention is used for developing polymer scaffolds for bone regeneration.

Mechanical properties of ECM play an important role in regulating cell behaviors in development, tissue homeostasis, and disease. Studies in this area have converged upon the findings that cell spreading, proliferation, and osteogenic differentiation are suppressed on substrates with low stiffness in vitro. However, these studies typically utilized purely elastic materials as substrates, whereas most physiological ECM is viscoelastic and exhibits stress relaxation, so that traction forces exerted by cells remodel the ECM. As described herein, the influence of substrate stress relaxation on a variety of cell behaviors was investigated using the hydrogels described herein—a new materials approach to modulate the stress relaxation properties of alginate hydrogel substrates. The proliferation and osteogenic differentiation of MSC that were seeded in the hydrogels were markedly enhanced in rapidly relaxing gels. This phenomenon has not been previously reported, and is a key factor in designing biomaterials for bone regeneration.

Example 1

Structural and Mechanical Properties of Hydrogels of the Invention

The nanoscale architecture of hydrogels was modulated to develop a set of materials with a wide range of stress relaxation rates, but a similar initial elastic modulus. As hydrogels exhibiting minimal degradation were desired, the polysaccharide alginate was chosen for these studies since mammalian cells do not express enzymes that can degrade this polymer (Lee, et al., *Chem. Rev.* 101, 1869-1879 (2001)). Alginate presents no intrinsic integrin binding sites for cells and minimal protein absorption, but cell adhesion can be promoted through covalent coupling of the RGD cell adhesion peptide to the alginate chains.

While the stress relaxation properties of hydrogels have been altered previously by changing crosslinking chemistries (Zhao et al., *J. Appl. Phys.* 107, 63509 (2010); McKinnon, et al., *Adv. Mater.* (2013)), a new materials approach was developed to control the rate of stress relaxation of hydrogels with a single crosslinker type. By using different molecular weight polymers in combination with different crosslinking densities of calcium, which ionically crosslinks alginate, the stress relaxation properties of the resulting hydrogels were modulated due to the altered connectivity and chain mobility (Graessley, W. W. in *Synth. Degrad. Rheol. Extrus.* 47, 67-117 (Springer-Verlag)) in the network (FIG. 1B). Any associated decrease in the initial elastic modulus resulting from decreased polymer molecular weight was compensated for by increased crosslinking. Thus, lowering the molecular weight of the alginate while increasing cross-linking led to faster stress relaxation while maintaining the initial elastic modulus. Further, covalent coupling of short steric spaces (e.g., PEG spacers) to the alginate provided a steric hindrance to crosslinking of alginate chains and enhanced stress relaxation in the gel (FIG. 1B).

For example, the molecular weight of the alginate was lowered from 280 kDa to 35 kDa, and 5 kDa PEG spacers were coupled to the 35 kDa alginate. In these gels, the rate of stress relaxation was enhanced markedly (FIG. 1C). Specifically, the time for the initial stress of the material to be relaxed to half its value during a stress relaxation test ($\tau_{1/2}$) was modulated from ~1 hour to ~1 minute, while holding alginate polymer concentration and the initial gel elastic modulus constant (FIGS. 1C-E; and Table 1).

Stress relaxation measured in ionically crosslinked alginate gels represents viscoelasticity of the hydrogel and unbinding of ionic crosslinks (Zhao, et al., *J. Appl. Phys.* 107, 63509 (2010)). This interpretation was confirmed by a measurement of the frequency dependent rheology of the gels, as an increase in the rate of stress relaxation correlated with a greater rate of decrease in the shear storage modulus with decreasing frequency (FIG. 6). Also consistent with this interpretation was the complete relaxation of the stress (i.e. to zero), indicating that these matrices could be plastically deformed/mechanically remodeled and that the shorter the $\tau_{1/2}$, the faster the matrices remodel under stress.

In addition, the mechanical properties of these gels were stable over a timescale of at least 7 days under tissue culture conditions, demonstrating that the degradation of these matrices was negligible (FIGS. 1F-G). These results demonstrated a new approach to control matrix stress relaxation, independent of the initial elastic modulus, polymer concentration, and without hydrogel degradation.

Example 2

Effects of Stress Relaxation on Cell Behavior in 3D Cultures

The effect of the rate of substrate stress relaxation on cell spreading and proliferation in 3D culture was investigated using the hydrogels described herein. Stress relaxation affected both cell spreading and proliferation. 3T3 fibroblasts were encapsulated within RGD coupled alginate hydrogels with varying stress relaxation rates but all with an initial elastic modulus of ~9 kPa (FIGS. 2A-C). Both cell spreading and proliferation were suppressed within materials with long timescales for stress relaxation ($\tau_{1/2}$~1 hour), and the rounded cell morphologies typical of cells in non-degradable hydrogels were observed under this condition.

Both spreading (e.g., increase in length of longest axis of cells) and proliferation increased with faster stress relaxation (Spearman's rank correlation, p<0.0001 for both). In addition, the influence of substrate stress relaxation on cell spreading and proliferation was enhanced when RGD cell adhesion ligand density was increased. This indicates that the effect of stress relaxation was mediated through integrin adhesions. This enhancement in spreading and proliferation was attributable to altered stress relaxation alone, as the initial elastic modulus and alginate concentration was held constant, and RGD cell adhesion ligand density was also constant at either 150 or 1500 µM. The observation of striking changes in cell shape in the rapidly relaxing hydrogels was consistent with plastic deformation/mechanical remodeling of the hydrogel by the cells, as these hydrogels were nanoporous and non-degradable.

Example 3

Effects of Stress Relaxation on Cell Differentiation in 3D Cultures

The influence of substrate stress relaxation on the differentiation of a murine mesenchymal stem cell line (D1, MSCs) in 3D culture was investigated. A previous study described that D1 MSCs (as well as primary human MSCs) encapsulated in ionically-crosslinked alginate hydrogels undergo predominantly adipogenic differentiation at initial moduli of 1-10 kPa, and predominantly osteogenic differentiation at initial moduli of 11-30 kPa (Huebsch, et al., *Nat Mater* 9, 518-526 (2010)). Based on this finding, it was thought that cells integrate the elastic modulus over time and feel an effectively lower elastic modulus on a viscoelastic substrate. If this were the case, osteogenic differentiation of MSCs in matrices with an initial elastic modulus of 11-30 kPa would be reduced with faster relaxation in the gel. However, the results described herein indicated otherwise.

MSCs were encapsulated in alginate hydrogels with various timescales of stress relaxation, initial elastic moduli, and RGD densities (FIGS. 3A-B and 7A-C). When the initial elastic modulus of the matrix was ~9 kPa, MSCs exhibited primarily adipogenic differentiation, as indicated by staining for neutral lipids, and very low levels of osteogenic differentiation, as indicated by alkaline phosphatase staining and a quantitative assay of alkaline phosphatase activity, for all timescales of stress relaxation probed (FIGS. 3A-B).

The level of adipogenesis was found to decrease in rapidly relaxing gels, which had a relaxation time of ~1 min. In contrast, at a higher initial elastic modulus of ~17 kPa, no adipogenic differentiation was observed, and osteogenic differentiation was significantly enhanced in gels with faster stress relaxation (FIGS. 3A-B, Spearman's rank correlation, p<0.0001). This was a surprising result, as it was the exact opposite of what one would expect if cells were simply integrating the elastic modulus of the matrix over time. Osteogenic differentiation was diminished at lower RGD ligand densities, demonstrating that the effect of stress relaxation was mediated through integrin adhesions, though the same trend of enhanced osteogenesis with faster stress relaxation is observed (FIGS. 8A-B). Calcium used to crosslink the alginate gels did not influence differentiation (FIG. 8C), as has been shown previously (Huebsch, et al., *Nat Mater* 9, 518-526 (2010)). Specific values for the conditions used in these experiments are shown in Table 1.

TABLE 1

Hydrogel compositions used in study

| Description | MW of alginate (kDa) | cross-linker conc. (mM) | Initial elastic modulus (kPa) | Stress relaxation |
|---|---|---|---|---|
| high-MW low stiffness | 280 | 12 | 9 | $\tau(1/2) = 3286$ |
| mid-MW low stiffness | 70 | 20 | 8.5 | 392 |
| low-MW low stiffness | 35 | 31 | 7.9 | 166 |
| low-MW-5K PEG low stiffness | 35 | 46 | 9.1 | 67 |
| high-MW mid-stiffness | 280 | 21 | 17 | 1382 |
| mid-MW mid-stiffness | 70 | 29 | 19 | 211 |
| low-MW mid-stiffness | 35 | 40 | 15 | 104 |
| low-MW-5K PEG mid-stiffness | 35 | 52 | 15 | 44 |

In addition to characterizing differentiation of the MSCs, the functional activity of the osteogenically differentiated stem cells was also examined. Previous studies had described osteogenic differentiation of MSCs within 3D matrices of slowly relaxing alginate gels (Huebsch, et al., *Nat Mater* 9, 518-526 (2010)), PEG gels (Parekh, et al., *Biomaterials* 32, 2256-2264 (2011)), degradable hyaluronic acid gels (Khetan, et al., *Nat. Mater.* (2013)), or a thixotropic PEG silica gel (Pek, et al., *Biomaterials* 31, 385-391 (2010)). However, formation of an interconnected mineralized and collagen-1 rich matrix, which are the two key structural components of bone, by these differentiated cells in vitro has not been reported. As such, the ability of the differentiated stem cells to function as active osteoblasts has been limited in hydrogels used to date.

In experiments with the hydrogels of the invention, Von Kossa staining, immunohistochemistry, and energy-dispersive X-ray spectroscopy (EDS) revealed that matrix mineralization and type-1 collagen deposition were both enhanced after 14 days in culture with faster stress relaxation (FIGS. 3C-D and 9A-D). MSCs formed an interconnected bone-like matrix in rapidly relaxing gels that exhibit a time constant of stress relaxation on the order of ~1 minute. This timescale of stress relaxation approaches that of coagulated marrow (FIG. 1A), which likely resembles the microenvironment of a fracture hematoma and is likely similar to that reported for an early fracture callous (McDonald, et al., *J. Orthop. Res. Off. Publ. Orthop. Res. Soc.* 27, 1508-1513 (2009)). This result demonstrates that the rapidly relaxing gels not only promoted maximal osteogenesis but also enabled bone-forming activity in the osteogenically differentiated stem cells.

Example 4

Role of the YAP Transcriptional Regulator in Mediating Cell Response to Mechanical Changes in 3D Cultures After finding strong effects of the initial elastic modulus and the rate of stress relaxation on differentiation, nuclear localization of the YAP transcriptional regulator was investigated. The YAP transcriptional regulator was thought to be the key regulatory element controlling the gene expression of cells in response to mechanical or geometric cues (Dupont, et al., *Nature* 474, 179-183 (2011)). Nuclear localization of YAP was previously described to direct MSC differentiation into adipogenic or osteogenic lineages (Dupont, et al., *Nature* 474, 179-183 (2011); Swift, et al., *Science* 341, 1240104 (2013)) for MSCs cultured on 2D acrylamide substrates in response to altered substrate stiffness.

In the hydrogels of the invention, nuclear translocation of YAP increased with faster stress relaxation for both values of initial elastic moduli tested (Spearman's rank correlation, p<0.0001 for both), indicating that matrix stress relaxation had an important effect on transcriptional factor activity. The levels of nuclear YAP spanned the same range for the two different moduli (FIGS. 4A-B). As adipogenic differentiation is primarily observed in the soft substrates (9 kPa), and osteogenic differentiation is primarily observed in the stiff substrates (17 kPa), this indicated a decoupling of nuclear translocation of YAP from MSC fate (FIGS. 4C-D). These findings demonstrate that localization of YAP did not by itself control the differentiation of MSCs in 3D cell culture. Thus, there are critical differences in cell signaling and mechanotransduction that occur in 3D relative to 2D cell culture.

Example 5

Model for Predicting the Impact of Stress Relaxation on Cell Spreading

A model was developed to predict the impact of stress relaxation on cell spreading. Since the time dependent elastic modulus of substrates with stress relaxation decreases over time when strained by cell traction forces, it was thought that cells would integrate the modulus over time, and thus respond to substrates with stress relaxation as if they were substrates with an effectively lower elastic modulus. If this were the case, cell spreading would be attenuated in all cases on substrates with stress relaxation relative to elastic substrates, given the same initial elastic modulus.

To determine whether this was true in the very early stages of cell spreading, a stochastic lattice spring model was developed. Following a recent model of filopodial protrusion (Chan et al. *Science* 322, 1687-1691 (2008)), this model considered cell spreading to be driven by polymerization of actin that was coupled to the surface of a substrate through molecular clutch adhesions (the key parameters relevant to the early stages of cell spreading (Zhang et al. *Nat. Cell Biol.* 10, 1062-1068 (2008)). The model additionally incorporated substrate stress relaxation and cell adhesion ligand density (FIG. 13A). The substrate was modeled as a series of nodes connected by either Hookean springs, representing an elastic substrate, or 4-element Burgers models, representing a viscoelastic substrate that exhibits stress relaxation. Simulations of cell spreading based on this model were run on either elastic substrates or substrates with stress relaxation, and cell spreading velocity was predicted as a function of cell adhesion ligand density and initial stiffness (FIG. 13B). On both types of substrates, cell spreading increased as a function of stiffness, consistent with previous experimental findings. At high stiffness, the model predicted only small differences in spreading between elastic and relaxing substrates. Surprisingly, the simulations revealed a regime, at low stiffness and higher ligand densities, in which cell spreading could be significantly enhanced on substrates with stress relaxation relative to elastic substrates (FIG. 13C). While this model did not consider longer timescale and more complex feedback mechanisms (Zemel et al. *Nat. Phys.* 6, 468-473 (2010)), it predicted that substrate viscoelasticity had a significant effect when cells bound to substrates through molecular clutches.

Example 6

Stochastic Lattice Spring Model of Cell Spreading as a Function of Substrate Mechanics and Adhesion Ligand Density A more detailed description of the model discussed in Example 5 is presented below.

Model Assumptions

This model tested the influence of substrate stress relaxation and adhesion ligand density in a dynamic simulation of cell spreading, building upon the framework of a previous model by Chan and Odde (Chan et al. *Science* 322, 1687-1691 (2008)). The goal of these simulations was to, even with a simple treatment of spreading mechanics, test for striking differences in cell mechanosensing as a function of material-side parameters. To that end, the model assumed no feedback into the number or applied force of myosin motors (Clark et al. *Trends Cell Biol.* 17, 178-186 (2007); and Schwartz, M. A. *Cold Spring Harb. Perspect. Biol.* 2, a005066 (2010)) and did not distinguish between bundled and filamentous actin (Schwartz, M. A. *Cold Spring Harb. Perspect. Biol.* 2, a005066 (2010)). Also, the specific composition of linker proteins from the substrate to actin was not specified. Hence, the linker proteins were treated as a simple spring and no adhesion strengthening was considered (Schwartz, M. A. *Cold Spring Harb. Perspect. Biol.* 2, a005066 (2010)). Though more complex features of cell spreading can be incorporated into these models, they were not expected to alter the essential effect of stress relaxation revealed by this model, as the initiation of and early stages of cell spreading were thought to be independent of adhesion strengthening (i.e. focal adhesion maturation) (Zhang et al. *Nat. Cell Biol.* 10, 1062-1068 (2008)).

The linkers were assumed to undergo force-dependent dissociation as per the Bell model (Bell, G. I. *Science* 200, 618-627 (1978)) given by $k^*_{off} = k_{off} e^{F_{clutch}/F_{rup}}$, where $k^*_{off}$ is the force-dependent off-rate, $k_{off}$ is the unloaded off-rate, $F_{clutch}$ is the retarding force imposed by each clutch, and $F_{rup}$ is the rupture force per bond. In addition, it was assumed that integrins bound adhesion ligands prior to incorporation into the adhesion complex.

Inhibition of actin retrograde flow velocity was assumed to be a function of the force sustained in the molecular clutches in the following manner:

$$v_{retrograde} = v_{poly}\left(1 - \frac{\Sigma_{clutch} F_{clutch}}{F_{stall}}\right) \quad \text{(Equation 1)}$$

where $v_{spread}$ is the cell spreading velocity, $v_{poly}$ is the actin leading edge polymerization velocity, $v_{retrograde}$ is the actin retrograde flow velocity, $\Sigma_{clutch} F_{clutch}$ is the sum of retarding forces sustained in all of the adhesion sites, and $F_{stall}$ is the force required to stop actin retrograde flow velocity. The actin polymerization rate is treated as constant and the spreading velocity is thus given by $v_{spread} = v_{poly} - v_{retrograde}$.

The substrate was modeled as a 2D lattice of mass nodes, with each node connected to its neighbors via a simple spring in the purely elastic case, or a Burger's model, in the viscoelastic case (FIG. 14A). In the Burger's model, stress and strain were related by:

$$\sigma + \left(\frac{\eta_1}{E_1} + \frac{\eta_1}{E_2} + \frac{\eta_2}{E_2}\right)\frac{d\sigma}{dt} + \left(\frac{\eta_2}{E_2}\right)\frac{d^2\sigma}{dt^2} = \left(\frac{\eta_1^2 \eta_2}{E_1 E_2}\right)\frac{d\varepsilon}{dt}\frac{d^2\varepsilon}{dt^2} \quad \text{(Equation 2)}$$

where σ is the stress sustained in the linkage, ε is the linkage strain, $E_1$ is the Maxwell element stiffness, $E_2$ is the Voigt element stiffness, $\eta_1$ is the Maxwell element damping coefficient, and $\eta_2$ is the Voigt element damping coefficient. Alginate, the material used experimentally in this study, has previously been modeled using a Burger's model (Donati et al. *Biomacromolecules* 6, 1031-1040 (2005)). Material parameter ranges were calibrated based on canonical spreading responses to different parameters in the purely elastic case, with the low end for stiffness being those purely elastic substrates on which cells do not spread and the high end being those on which cells do spread (see Table 2).

TABLE 2

Parameter Values Used in Simulations[1]

| Parameter | Value | Source |
|---|---|---|
| $k_{off}$ | 0.1 s$^{-1}$ | Lele et al. *Biochem. Biophys. Res. Commun.* 369, 929-934 (2008) |
| $F_{rup}$ | 2 pN | Jiang et al. *Nature* 424, 334-337 (2003) |
| $v_{poly}$ | 120 nm/s | Cuda et al. *Biophys. J.* 72, 1767-1779 (1997) |
| $F_{stall}$ | 150 pN | Chan et al. *Science* 322, 1687-1691 (2008); and Molloy et al. *Nature* 378, 209-212 (1995) |
| $k_{on}$ | 1 s$^{-1}$ | Chan et al. *Science* 322, 1687-1691 (2008) |
| $\kappa_{clutch}$ | 5 pN/nm | Fisher et al. *Trends Biochem. Sci.* 24, 379-384 (1999) |
| Initial adhered length | 1 μm | Free parameter, adjusted to hasten simulation time required to observe differences in dynamics |
| $E_1$ | 0.01-100 pN/nm | Free parameter, ranges calibrated to experimental results on purely elastic substrate, also Chan et al. *Science* 322, 1687-1691 (2008) |

TABLE 2-continued

Parameter Values Used in Simulations[1]

| Parameter | Value | Source |
|---|---|---|
| $E_2$ | 0.01-100 pN/nm | Free parameter, ranges calibrated to experimental results on purely elastic substrate, also Chan et al. *Science* 322, 1687-1691 (2008) |
| $\eta_1$ | 0.01-100 pN s | Free parameter, ranges calibrated to experimental results on viscoelastic substrate |
| $\eta_2$ | 0.01-100 pN s | Free parameter, ranges calibrated to experimental results on viscoelastic substrate |
| Ligand Density | 0.004-0.02 ligands/nm | Comisar et al. *Biomaterials* 28, 4409-4417 (2007) |

[1]Parameters were used from representative sources, although other values from other studies on the same order of magnitude could also have been used with free parameters adjusted accordingly.

On the top level of nodes, only certain nodes were made available for binding by the cell as determined by the ligand density. Ligand densities were approximated, based on previous approaches to quantify spacing of RGD ligands on alginate hydrogels for varying degrees of coupling that were consistent with those used in this study (Comisar et al. *Biomaterials* 28, 4409-4417 (2007)).

Model Implementation

The simulations were carried out in MATLAB (FIG. 14B). The model was tested for a range of time steps, and a time step within the stable range was chosen (0.2 ms, FIG. 15A). At each time step, it was determined whether the cell spreading front had passed a new available adhesion ligand on the substrate. If so, a new bond may be formed, as determined by $k_{on}$ and the number of adhered clutches was incremented. Given the current filament velocity, a strain of $dt^* v_{fil}$ was imposed on the substrate via the clutches. Equation 2 was discretized using a Backward Euler method, and the force between each node and its neighbors was calculated based on the new strain. For each node in the lattice, the resultant horizontal and vertical forces were found by summing the horizontal and vertical components of the force between the node and each of its neighbors; the equations of motion were then solved using an implicit Beeman scheme to find the new position of each node in the lattice for that time step.

At this point, based on the new strain profile of the lattice, the new force sustained in each molecular clutch was calculated using the clutch spring constant, $\kappa_{clutch}$, and each molecular clutch was tested for dissociation per the Bell model described above. The new forces sustained in each clutch were used to update the actin retrograde flow velocity for the next time step.

Model Characterization

By eliminating the ligand density dependence and treating the substrate as a simple spring, the "load and fail" and "frictional slippage" regimes described by Chan and Odde were recreated (FIG. 15B). Upon incorporating the material lattice and ligand density, dissociation events as well as clutch addition due to spreading were noted (FIG. 15C). In order to validate the behavior of the lattice, simulated tensile tests were performed to confirm purely elastic or viscoelastic behaviors. At a constant strain rate, purely elastic substrates demonstrated a linear force/extension relationship, while viscoelastic substrates demonstrated stress relaxation, confirming the capability of the substrate lattice to capture both purely elastic and viscoelastic behaviors (FIG. 15D).

Example 7

Validation of the Cell Spreading Model in 2D Cultures

In order to test the predictions of the model described above, cell spreading was investigated in 2D cultures on alginate substrates with and without stress relaxation. Alginate is a polysaccharide derived from seaweed. It presents no intrinsic integrin binding sites and minimal protein absorption, but cell adhesion could be promoted through covalent coupling of the RGD cell adhesion peptide (Rowley et al. *Biomaterials* 20, 45-53 (1999)). RGD-coupled alginate could be crosslinked into a hydrogel and used as a substrate for cell adhesion and spreading (Kong et al. *Proc. Natl. Acad. Sci. U.S.A.* 102, 4300-4305 (2005)). Recent work has highlighted the impact of the mode of ECM molecule tethering to substrates on cell behavior (Trappmann et al. *Nat. Mater.* 11, 642-649 (2012)). Unlike previous approaches, the use of short adhesion peptides covalently coupled to the substrate in the hydrogels described herein avoided this potential complication, as the peptide attachment to the alginate was uniform and the peptides were homogenously distributed. Covalently crosslinking the alginate itself led to elastic substrates that had little stress relaxation (FIG. 16A). Some stress relaxation was measured at longer timescales; however, this was previously found to be due to water migration out of the alginate gels during bulk compression and was likely not as relevant at the length/scale of a cell (Zhao et al. *J. Appl. Phys.* 107, 63509 (2010)). This interpretation was confirmed by the frequency independence of the shear storage modulus (FIG. 16B). Alternatively, crosslinking the alginate ionically, with divalent cations such as $Ca^{2+}$, led to substrates that were viscoelastic and exhibited stress relaxation (FIG. 16A) due to matrix reorganization over time (Zhao et al. *J. Appl. Phys.* 107, 63509 (2010)). This was confirmed by the frequency dependence of the shear storage modulus (FIG. 16B), and occurred because ionic crosslinks were reversible and could unbind and rebind when stresses were applied to the hydrogels (Zhao et al. *J. Appl. Phys.* 107, 63509 (2010)). Crosslinking was adjusted so that the initial Young's moduli of the covalently and ionically crosslinked hydrogels, as measured by atomic force microscope indentation, could be matched for various values (FIG. 16C).

With these set of substrates, U2OS (a human bone osteosarcoma cell line) cells were plated on substrates with various, matched initial elasticities that were crosslinked ionically or covalently. These studies revealed that cell spreading area increased as the initial Young's modulus was increased from 1.4-9 kPa on both ionically and covalently crosslinked gels (FIGS. 17A-B, Spearman's rank correlation p<0.001), consistent with previous work and the simulations described above. At a low modulus of 1.4 kPa, greater cell spreading area and stress fiber formation were observed on substrates that exhibited stress relaxation compared to purely elastic substrates, consistent with the model prediction. This effect was enhanced markedly as ligand density was increased (Spearman's rank correlation, p<0.0001), also consistent with the model (FIGS. 17C-D). Similar results were found for spreading of 3T3 mouse fibroblasts on these substrates (FIG. 17E). Thus, in 2D cultures, U2OS cells did not spread on soft RGD-coupled elastic substrate. In 2D cultures, cell spreading and proliferation on viscoelastic substrates were similar to that of stiffer elastic substrates.

In U2OS cells, addition of a Rho associated protein kinase (ROCK) inhibitor (Y-27632) abrogated the increased cell spreading that occurred with substrate stress relaxation at low stiffness (FIG. 18A), demonstrating that the effect of stress relaxation on cell spreading was mediated through Rho and actomyosin based contractility (Wozniak et al. *Nat. Rev. Mol. Cell Biol.* 10, 34-43 (2009)). Further, substrate stress relaxation led to increased nuclear translocation of the YAP transcriptional regulator (FIGS. 18B-C), which is a key transcriptional element mediating mechanotransduction for cells on 2D substrates (Dupont et al. *Nature* 474, 179-183 (2011)). Consistent with the result of enhanced nuclear translocation of YAP, proliferation was increased in this cancer cell line with substrate stress relaxation (FIG. 18D). Surprisingly, these findings demonstrated that cells were not simply integrating the modulus over time on substrates that exhibited stress relaxation. While it had previously been thought that cell spreading and proliferation is suppressed on soft substrates, these results show that substrate stress relaxation can directly compensate for the effect of decreased stiffness, as the effect of stress relaxation is mediated through some of the same pathways as stiffness: integrin adhesions, Rho activation, and actomyosin based contractility, and nuclear translocation of YAP.

Example 8

Influence of Calcium Crosslinker on Cell Behavior

For the 2D studies described in the Examples above, gels are washed 4 times in a significant excess of media over 2 days to remove excess calcium. Further, the marked dependence of cell spreading on RGD ligand density on ionically crosslinked gels demonstrated that the effect on cell behavior was mediated through ligands attached to the alginate matrix, not due to soluble calcium. Also, for the 3D studies described in the Examples above, in which a strong dependence of cell spreading, proliferation, and differentiation on ligand density was measured, the concentrations of calcium used for the alginate gels with different stress relaxation and different initial moduli overlapped. This indicated that there was no coupling between cell fate and calcium concentrations. For example, adipogenesis was observed in ~100% of cells matrices with an initial moduli of 9 kPa, $\tau_{1/2}$=166 s, and a concentration of 31 mM Ca, whereas primarily osteogenesis was observed in matrices with an initial moduli of 17 kPa, $\tau_{1/2}$=211 s, and a calcium concentration of 29 mM Ca (Table 3).

TABLE 3

List of the hydrogel compositions used in Examples 1-8 above

| Description | Used in: | MW of alginate (kDa) | % alg. | cross-linker type | cross-linker conc. (mM) | Modulus (kPa) | Modulus measured by | Stress relaxation |
|---|---|---|---|---|---|---|---|---|
| Covalently crosslinked, high modulus | 2D | 280 | 2 | AAD | 3 | 9.7 | AFM | None |
| Covalently crosslinked, inter. Modulus | 2D | 280 | 2 | AAD | 0.6 | 3.4 | AFM | None |
| Covalently crosslinked, low modulus | 2D | 280 | 2 | AAD | 0.3 | 1.5 | AFM | None |
| Ionically crosslinked, high modulus | 2D | 280 | 3.6 | $Ca^{2+}$ | 72 | 8 | AFM | Yes |
| Ionically crosslinked, inter. Modulus | 2D | 280 | 2 | $Ca^{2+}$ | 48 | 3.3 | AFM | Yes |
| Ionically crosslinked, low modulus | 2D | 280 | 2 | $Ca^{2+}$ | 24 | 1.4 | AFM | Yes |
| high-MW low stiffness | 3D | 280 | 2 | $Ca^{2+}$ | 12 | 9 | Bulk compression | ($\tau_{1/2}$) = 3286 |
| mid-MW low stiffness | 3D | 70 | 2 | $Ca^{2+}$ | 20 | 8.5 | Bulk compression | 392 |
| low-MW low stiffness | 3D | 35 | 2 | $Ca^{2+}$ | 31 | 7.9 | Bulk compression | 166 |
| low-MW-5K PEG low stiffness | 3D | 35 | 2 | $Ca^{2+}$ | 46 | 9.1 | Bulk compression | 67 |
| high-MW mid-stiffness | 3D | 280 | 2 | $Ca^{2+}$ | 21 | 17 | Bulk compression | 1382 |
| mid-MW mid-stiffness | 3D | 70 | 2 | $Ca^{2+}$ | 29 | 19 | Bulk compression | 211 |

TABLE 3-continued

List of the hydrogel compositions used in Examples 1-8 above

| Description | Used in: | MW of alginate (kDa) | % alg. | cross-linker type | cross-linker conc. (mM) | Modulus (kPa) | Modulus measured by | Stress relaxation |
|---|---|---|---|---|---|---|---|---|
| low-MW mid-stiffness | 3D | 35 | 2 | Ca$^{2+}$ | 40 | 15 | Bulk compression | 104 |
| low-MW-5K PEG mid-stiffness | 3D | 35 | 2 | Ca$^{2+}$ | 52 | 15 | Bulk compression | 44 |

Collectively, the data showed that the calcium used to crosslink the alginate gels was not influencing cell behavior in the experiments described above. This finding was consistent with the results of a previous study of MSC differentiation inside alginate gels that were ionically crosslinked (Huebsch et al. *Nat Mater* 9, 518-526 (2010)).

Example 9

Stress Relaxation Regulates Bone Formation In Vivo

Preparation and Characterization of Hydrogels Used in In Vivo Studies

To test the ability of substrate stress relaxation to regulate osteogenic differentiation of human MSCs (hMSCs), calcium-crosslinked alginate hydrogels were chosen as cell scaffolds (Chaudhuri O, et al. (2015), *Nat Commun* 6).

Alginate hydrogels were fabricated using alginate chains of two different molecular weights at an initial stiffness slightly lower than has been reported to be optimal for osteogenic differentiation of MSCs (Huebsch N, et al. (2010) Nat Mater 9(6):518-526). This stiffness was chosen in order to sensitize the cells to the effect of the stress relaxation and ensure that stiffness effects did not dominate the mechanical cues delivered to the cells. The gels were modified with an RGD peptide motif to support cell adhesion but contained no exogenous growth factors or small molecules.

Compression testing confirmed that any difference in the initial elastic moduli of these two conditions was not statistically significant (FIG. 19A). However, hydrogels fabricated with the high molecular alginate demonstrated significantly longer relaxation times than the low molecular weight hydrogels (FIG. 19B).

Next, hMSCs were encapsulated in alginate hydrogels of the same stiffness and each molecular weight and cultured in osteogenic induction medium for two weeks in order to assess the differences in differentiation of hMSCs in hydrogels with different stress relaxation times.

Fast-relaxing gels contracted significantly more than slow-relaxing gels which is suggestive of increased cellular traction forces (FIG. 19C). Consistent with previous results in mouse stem cells, von Kossa staining of the hydrogels showed significantly more matrix deposition and mineralization for the fast-relaxing hydrogels, indicative of osteogenic differentiation (FIG. 19D) RR.

As confirmation of increased mineralization that is consistent with osteogenic differentiation of the hMSCs, energy dispersive X-ray spectroscopy (EDS) was performed to map elemental phosphorous in the interior of the hydrogels. Substantially more phosphorous was found in the fast-relaxing gels, consistent with the von Kossa staining and the notion that osteogenic differentiation of hMSCs in the fast-relaxing gels was much more potent (FIG. 19E).

In Vivo Studies Using Fast Relaxing and Slow Relaxing Hydrogels

In order to assess the in vivo effects of substrate stress relaxation, hydrogels in the same formulations used for the above in vitro studies were implanted into a rat calvarial defect model in which a circular defect is drilled into the rat calvarium and a biomaterial is placed into the void. This model of bone regeneration was chosen due to its wide use in the field and the possibility of creating a critical-sized defect that does not require external stabilization (Spicer P P, et al. (2012) *Nature Protocols* 7(10):1918-1929). For this study, 8 mm defects were drilled and hMSCs encapsulated in 8 mm-diameter slow or fast-relaxing alginate gels were implanted. After three months, the rats were euthanized and the skulls were explanted and examined for bone formation using X-ray micro-computed tomography (μCT). Representative images showed a striking increase in new bone formed for the fast-relaxing hydrogels and quantification of the new bone volume confirmed a statistically significant difference in the amount of new bone formed and the percentage of the defect that is spanned (FIG. 20).

The histology of the defects was next examined to assess the structure of the new bone (FIG. 21A-C). Hematoxyln and Eosin (H&E), van Gieson, and Masson's Trichrome stainings depict that the new bone formed in the fast-relaxing condition is mature, featuring collagen-rich and relatively acellular regions with sparse osteocytes. Furthermore, the presence of elongated osteoblasts on the periphery of the new bone and osteoid regions rich in disorganized collagen indicate active bone growth. In contrast, the slow-relaxing condition showed sparse, disorganized collagen, without prominent bone growth centers or mature bone.

Additionally, Alcian Blue staining for residual alginate revealed that the hydrogels are mostly degraded in the fast-relaxing case, whereas significant residual hydrogel is noted in the slow-relaxing case (FIG. 21D). These results indicate that the matrix is more remodeled in the fast-relaxing condition.

In order to gauge the relative contribution of rat versus human cells to the new bone formed, human mitochondria were stained to label all progeny of the transplanted human cells. (FIGS. 22A-B and 23). Human cells were markedly absent from the slow-relaxing condition, while a small number of human cells were localized to the periphery of new bone in the fastrelaxing condition. The relative paucity and localization of human cells indicates that involvement of these cells in the bone formation process occurred early and at least partially via paracrine mechanisms. Moreover, the presence of these cells in the zone of new bone formation and not in the mature bone indicates that these cells are actively participating in new bone growth.

These results demonstrate that substrate stress relaxation can be a potent regulator of bone formation in vivo. Specifically, rat calvarial defects treated with stiffness-matched hydrogels carrying hMSCs showed significantly more bone formation after three months if the hydrogels exhibited a relatively fast stress relaxation time. Such a result demonstrates the idea that substrate mechanical properties can be used as pro-osteogenic cues for bone tissue engineering and suggests that the stiffness as well as the stress relaxation timescale of biomaterials could be tuned to further optimize the bone-forming capabilities of cell-laden implants.

Additionally, the new bone formed in defects with fast-relaxing implants exhibits a mature morphology indicative of the activation of a robust wound healing cascade. This morphology is comparable to the results of previous studies that delivered growth factors such as BMP-2 to defect sites, a result that implies a great relative importance of extracellular mechanical properties to bone formation (Haidar Z. et al. (2009) Biotechnol Lett 31(12):1817-1824). The presence of human derived cells at the new-bone-periphery in conditions with fast-relaxing gels, but absence of human cells in slow-relaxing conditions indicates a role for fast-relaxing gels in providing survival cues to the cells as well as a persistent role for the remaining cells in the bone healing cascade. Based on the apparent potency of both mechanical and biological factors in inducing bone formation, an approach involving mechanical optimization and growth factor delivery is a promising approach to bone healing.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

We claim:

1. A fast relaxing hydrogel comprising a plurality of alginate polymer chains and a plurality of linear spacer molecules, wherein the plurality of alginate polymer chains have an average molecular weight of about 80 kDa or less;

the plurality of alginate polymer chains are ionically cross-linked to each other using $Ca^{2+}$, wherein $Ca^{2+}$ is present in said hydrogel at a concentration of about 2 mM to about 60 mM;

wherein each of the plurality of linear spacer molecules comprises a first end and a second end, wherein the first end is covalently attached to an alginate polymer chain and the second end is not attached to an alginate polymer chain, wherein each of the plurality of linear spacer molecules does not cross-link the alginate polymer chains, and wherein the plurality of linear spacer molecules physically separate the alginate polymer chains;

wherein the plurality of alginate polymer chains and the plurality of spacer molecules are present in the hydrogel at a ratio of at least 2:1 spacer molecule: alginate polymer chain;

wherein the length of each of the plurality of linear spacer molecules ranges from about 80 Angstroms to about 1500 Angstroms; and wherein the hydrogel is characterized by a stress relaxation rate ($\tau_{1/2}$) of 800 seconds or less.

2. The hydrogel of claim 1, wherein the plurality of alginate polymer chains have an average molecular weight of about 70 kDa or less.

3. The hydrogel of claim 2, wherein the plurality of alginate polymer chains have an average molecular weight of about 35 kDa.

4. The hydrogel of claim 1, wherein the hydrogel is viscoelastic and exhibits relaxation behavior when stress is applied to the hydrogel.

5. The hydrogel of claim 1, wherein said stress relaxation rate ($v_{1/2}$) is 500 seconds or less.

6. The hydrogel of claim 5, wherein said stress relaxation rate ($v_{1/2}$) is 100 seconds or less.

7. The hydrogel of claim 1, wherein the ratio is about 2:1 spacer molecule: alginate polymer chain.

8. The hydrogel of claim 1, wherein the spacer molecule is polyethylene glycol (PEG).

9. The hydrogel of claim 8, wherein the PEG has a molecular weight of less than 50 kDa.

10. The hydrogel of claim 8, wherein the PEG has a molecular weight of between about 5 kDa and about 20 kDa.

11. The hydrogel of claim 1, further comprising a cell adhesive peptide.

12. The hydrogel of claim 11, wherein the cell adhesive peptide is attached to each of the plurality of alginate polymer chains.

13. The hydrogel of claim 12, wherein the cell adhesive peptide comprises an arginine-glycine-aspartate (RGD) amino acid sequence.

14. The hydrogel of claim 1, wherein the hydrogel comprises interconnected pores.

15. The hydrogel of claim 14, wherein the pores comprise nanopores.

16. The hydrogel of claim 1, further comprising a mammalian cell.

17. The hydrogel of claim 16, wherein the mammalian cell is a fibroblast or a mesenchymal stem cell (MSC).

18. The hydrogel of claim 1, wherein the hydrogel is characterized by an initial elastic modulus of about 11 kPa and about 30 kPa.

19. A fast relaxing hydrogel comprising a plurality of alginate polymer chains and a plurality of linear spacer molecules, wherein
the plurality of alginate polymer chains have an average molecular weight of about 80 kDa or less;
the plurality of alginate polymer chains are ionically cross-linked to each other using $Ca^{2+}$, wherein $Ca^{2+}$ is present in said hydrogel at a concentration of about 2 mM to about 60 mM;
wherein each of the plurality of linear spacer molecules comprises a first end and a second end, wherein the first end is covalently attached to an alginate polymer chain and the second end is not attached to an alginate polymer chain, wherein each of the plurality of linear spacer molecules does not cross-link the alginate polymer chains, and wherein the plurality of linear spacer molecules physically separate the alginate polymer chains;
wherein the plurality of alginate polymer chains and the plurality of spacer molecules are present in the hydrogel at a ratio of at least 2:1 spacer molecule: alginate polymer chain;
wherein the spacer molecule is polyethylene glycol (PEG) having a molecular weight of between about 5 kDa and about 49 kDa; and
wherein the hydrogel is characterized by a stress relaxation rate ($v_{1/2}$) of 800 seconds or less.

20. The hydrogel of claim 19, wherein the hydrogel is viscoelastic and exhibits relaxation behavior when stress is applied to the hydrogel.

21. The hydrogel of claim 19, wherein the plurality of alginate polymer chains and the plurality of spacer molecules are present in the hydrogel at a ratio of about 2:1 spacer molecule: alginate polymer chain.

22. The hydrogel of claim 19, further comprising a cell adhesive peptide.

23. The hydrogel of claim 19, further comprising a mammalian cell.

* * * * *

UNITED STATES PATENT AND TRADEMARK OFFICE
CERTIFICATE OF CORRECTION

| | | |
|---|---|---|
| PATENT NO. | : 11,065,362 B2 | Page 1 of 1 |
| APPLICATION NO. | : 14/738294 | |
| DATED | : July 20, 2021 | |
| INVENTOR(S) | : Luo Gu et al. | |

It is certified that error appears in the above-identified patent and that said Letters Patent is hereby corrected as shown below:

In the Specification

At Column 1, Line number 13-16, please replace:
"The invention was supported, in whole, or in part, by a National Institutes of Health (NIH) F32 grant (CA153802) and a NIH grant (ROI DE013033). The Government has certain rights in the invention."
With:
--This invention was made with government support under DE013033 and CA153802 awarded by National Institutes of Health (NIH). The government has certain rights in this invention.--

Signed and Sealed this
Fourth Day of October, 2022

Katherine Kelly Vidal
*Director of the United States Patent and Trademark Office*